(12) United States Patent
Seip et al.

(10) Patent No.: US 7,923,223 B2
(45) Date of Patent: Apr. 12, 2011

(54) Δ-9 DESATURASE AND ITS USE IN MAKING POLYUNSATURATED FATTY ACIDS

(75) Inventors: John E. Seip, Alloway, NJ (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 697 days.

(21) Appl. No.: 11/613,420

(22) Filed: Dec. 20, 2006

(65) Prior Publication Data
US 2008/0153141 A1 Jun. 26, 2008

(51) Int. Cl.
*C12P 7/64* (2006.01)
*C12N 9/00* (2006.01)
*C12N 9/02* (2006.01)
*C12N 1/20* (2006.01)
*C12N 15/00* (2006.01)
*C07H 21/04* (2006.01)

(52) U.S. Cl. ..... 435/134; 435/183; 435/189; 435/252.3; 435/320.1; 536/23.2

(58) Field of Classification Search ............... None
See application file for complete search history.

(56) References Cited

U.S. PATENT DOCUMENTS 6,448,055 B1 9/2002 Shimizu et al.
6,495,738 B1 12/2002 Folkerts et al.

FOREIGN PATENT DOCUMENTS

WO WO 2006/052870 A2 5/2006

OTHER PUBLICATIONS

U.S. Appl. No. 10/840,478, filed Dec. 16, 2004, Stephen K. Picataggio et al.
U.S. Appl. No. 10/840,579, filed Jun. 23, 2005, Stephen K. Picataggio et al.
U.S. Appl. No. 10/840,325, filed Feb. 24, 2005, Narendra S. Yadav et al.
U.S. Appl. No. 10/869,630, filed Jan. 20, 2005, Stephen K. Picataggio et al.
U.S. Appl. No. 10/882,760, filed Jul. 20, 2006, Narendra S. Yadav et al.
U.S. Appl. No. 10/985,109, filed Jun. 16, 2005, Howard Glenn Damude et al.
U.S. Appl. No. 10/985,691, filed Sep. 29, 2005, Narendra S. Yadav et al.
U.S. Appl. No. 10/987,548, filed Jun. 16, 2005, Dana M. Walter et al.
U.S. Appl. No. 11/024,545, filed May 4, 2006, Zhixiong Xue et al.
U.S. Appl. No. 11/024,544, filed May 4, 2006, Narendra S. Yadav et al.
U.S. Appl. No. 11/166,993, filed Dec. 29, 2005, Howard Glenn Damude et al.
U.S. Appl. No. 11/183,664, filed Jan. 26, 2006, Stephen K. Picataggio et al.
U.S. Appl. No. 11/185,301, filed May 4, 2006, Zhixiong Xue et al.
U.S. Appl. No. 11/190,750, filed May 4, 2006, Stephen K. Picataggio et al.
U.S. Appl. No. 11/198,975, filed Aug. 8, 2005, Quinn Qun Zhu et al.
U.S. Appl. No. 11/225,354, filed Mar. 16, 2006, Zhixiong Xue et al.
U.S. Appl. No. 11/251,466, filed May 4, 2006, Howard Glenn Damude et al.
U.S. Appl. No. 11/254,173, filed May 4, 2006, Daniel Joseph Macool et al.
U.S. Appl. No. 11/253,882, filed Apr. 19, 2007, Daniel Joseph Macool et al.
U.S. Appl. No. 11/264,784, filed May 4, 2006, Howard Glenn Damude et al.
U.S. Appl. No. 11/264,737, filed May 25, 2006, Howard Glenn Damude et al.
U.S. Appl. No. 11/265,761, filed Jun. 1, 2006, Howard Glenn Damude et al.
U.S. Appl. No. 60/795,810, filed Apr. 28, 2006, Howard Glenn Damude et al.
U.S. Appl. No. 60/793,575, filed Apr. 20, 2006, Zhixiong Xue et al.
U.S. Appl. No. 60/796,637, filed May 1, 2006, Narendra S. Yadav et al.
U.S. Appl. No. 60/801,172, filed May 17, 2006, Howard Glenn Damude et al.
U.S. Appl. No. 60/801,119, filed May 17, 2006, Howard Glenn Damude et al.
U.S. Appl. No. 60/853,563, filed Oct. 23, 2006, Howard Glenn Damude et al.
U.S. Appl. No. 60/855,177, filed Oct. 30, 2006, Zhixiong Xue et al.
U.S. Appl. No. 11/601,564, filed May 24, 2007, Howard Glenn Damude et al.
U.S. Appl. No. 11/635,258, filed Dec. 7, 2006, Howard Glenn Damude et al.
J. Dyerberg et al., Fatty Acid Composition of the Plasma Lipids in Greenland Eskimos, Amer. J. Clin. Nutr., 1975, vol. 28:958-966.
J. Dyerberg et al., Eicosapentaenoic Acid and Prevention of Thrombosis and Atherosclerosis, Lancet, 1978, vol. 2:117-119. H. Shimokawa, Beneficial Effects of Eicosapentaenoic Acid on Endothelial Vasodilator Functions in Animals and Humans, World Rev. Nutr. Diet, 2001, vol. 88:100-108.
C. Von Schacky et al., 3 Fatty Acids—From Eskimos to Clinical Cardiology—What Took Us so Long?, World Rev. Nutr. Diet, 2001, vol. 88:90-99.
S. Smith, The Animal Fatty Acid Synthase: One Gene, One Polypeptide Seven Enzymes, FASEB J., 1994, vol. 8:1248-1259.
J.E. Stukey et al., The OLE1 Gene of *Saccharomyces cerevisiae* Encodes the 9 Fatty Acid Desaturase and Can Be Functionally Replaced by the Rat Stearoyl-CoA Desaturase Gene, J. Biol. Chem., 1990, vol. 265:20144-20149.
P.A. Meesters et al., Isolation and Characterization of a 9-Fatty Acid Desaturase Gene From the Oleaginous Yeast *Cryptococcus curvatus* CBS 570, Yeast, 1996, vol. 12:723-730.
National Center for Biotechnology Information General Identifier No. AB071696, Mar. 19, 2002, S. Kajiwara, Delta 9-Fatty Acid Desaturase Gene (SK-OLEI) of *Saccharomyces kluyveri*.
S. Kajiwara, Molecular Cloning and Characterization PF the 9 Fatty Acid Desaturase Gene and Its Promoter Region From *Saccharomyces Kluyveri*, FEMS Yeast Res., 2002, vol. 2:333-339.

*Primary Examiner* — Christian L Fronda
(74) *Attorney, Agent, or Firm* — Lynne M. Christenbury

(57) ABSTRACT

The present invention relates to a Δ9 desaturase, which has the ability to convert palmitic acid [16:0] or stearic acid [18:0] into palmitoleic acid [16:1] or oleic acid [18:1], respectively. Isolated nucleic acid fragments and recombinant constructs comprising such fragments encoding Δ9 desaturase along with a method of making long chain polyunsaturated fatty acids (PUFAs) using this Δ9 desaturase in oleaginous yeast is disclosed.

19 Claims, 7 Drawing Sheets

Figure 3

Conserved Region 1

```
205 W Q E Q H W T - H H A Y T N H A E M D P D S F G A E P M L F N D - - - Y P L D H    Pt (SEQ ID NO:16)
225 W L N Q H V V G H H I Y T N V A G A D P D - L P V D F K S D V R - - - R I V Y R    PM (SEQ ID NO:17)
204 W L N Q H V V G H H I Y T N V A G A D P D - L P V D F E S D V R - - - R I V H R    Pi (SEQ ID NO:18)
207 W C H Q H V I G H H L Y T N V R N A D P D - L G Q G - E I D F R - - - V V T P Y    Dc (SEQ ID NO:19)
178 W K D R H N A - H H S A T N V Q G H D P D - I D N L P L L A W S E D D V T R A S    Eu-D8DSWT (SEQ ID NO:20)
205 W R A R H N T - H H V C T N E D G S D P D - I K T A P L L I Y V R E N P S I A K    PvD8WT (SEQ ID NO:22)

242 P A R T W L H R F Q A F F Y M P V L A G Y W L S A V F N P Q I L D - L Q Q R G A    Pt (SEQ ID NO:16)
261 Q V L L P I Y K Y Q - H L Y L P P L Y G V L G - - - L K F R V Q D V F E T F V T    PM (SEQ ID NO:17)
240 Q V L L P I Y K F Q - H I Y L P P L Y G V L G - - - L K F R I Q D V F E T F V S    Pi (SEQ ID NO:18)
242 Q A R S W Y H K Y Q - H I Y A P I L Y G V Y A - - - L K Y R I Q D - H E I F T K    Dc (SEQ ID NO:19)
216 P I S R K L I Q F Q - Q Y Y F L V I C I L L R - - - F I W C F Q S V L T V R S L    Eu-D8DSWT (SEQ ID NO:20)
243 R L N - F F Q R W Q - Q Y Y Y V P T M A I L D - - - - L Y W R L E S I A Y V A V R  PvD8WT (SEQ ID NO:22)

281 L S V G I R L D N A F I H S R R K Y A V F W R A V Y I A V N V I A P F Y T N S G    Pt (SEQ ID NO:16)
297 L T N G P L R V N P L S V G D W A E M I L S K A F W V F Y R I Y L P L A V L Q V    PM (SEQ ID NO:17)
276 L T N G P V R V N P H P V S D W V Q M I F A K A F W T F Y R I Y I P L V W L K I    Pi (SEQ ID NO:18)
277 K S N G A I R Y S P I S T I D T A I F I L G K L V F I I S R F I L P L I Y N H S    Dc (SEQ ID NO:19)
252 K D - - - - R D N Q F Y R S Q Y K K E A I G L A L H W T L K T L F H L F M P S      Eu-D8DSWT (SEQ ID NO:20)
278 - - - - - - - - - - - L P K M W M Q A A A L A A H Y A L - - L C W V F A A H L      PvD8WT (SEQ ID NO:22)
```

Conserved Region 2

```
321 - L E W S W R V F G N I M L M G V A E S L A L A V L F S L S H N F E S A D R D P    Pt (SEQ ID NO:16)
337 D P A R F W G V F - - - F L A E F S T G W Y L A F N F Q V S H V S T A C E Y P G    PM (SEQ ID NO:17)
316 T P S T F W G V F - - - F L A E F T T G W Y L A F N F Q V S H V S T E C E Y P C    Pi (SEQ ID NO:18)
317 - F S H L I C F F - - - L I S E L V L G W Y L A I S F Q V S H V V E D L Q F M A    Dc (SEQ ID NO:19)
288 I L T S L L V F F - - - - - V S E L V G G F G I A I V V F M N H Y P L E K I G D S  Eu-D8DSWT (SEQ ID NO:20)
304 N L I P L M M V A - - - - - R - - - - - G F A T G I V V F A T H Y G E D I L D R E  PvD8WT (SEQ ID NO:22)
```

Figure 4

```
        R  R  W  V  T K  K  R  N  W  W  W  P  R  T  Y  N  S  T  D  I  V  F  I  L  V  T  F  S  M  H  A  A  A  L  I  L  G  P
      GGACATCATGTTTATACAAGAAGAGAAACTGGTGGTGGCCAAGAACCTACAATTCAACAGATATTGTCTTTATCCTTGTTACCTTTTCCATGCATGCGGCTGCGCTCATTTTGGGCCCC  120
      ++++|++++|++++|++++|++++|++++|++++|++++|++++|++++|++++|++++|++++|++++|++++|++++|++++|++++|++++|++++|++++|++++|++++|++++|
      CCTGTAGTACAAATATGGTTCTTCTCTTTGACCACCACCGGTTCTTGGATGTTAAGTTGTCTATAACAGAATAGGAACAATGGAAAAGGTACGTACGCCGACGCGAGTAAAACCCGGGG
        P  C  .  T  .  V  L  F  L  F  Q  H  H  G  L  V  .  L  E  V  S  I  T  K  I  R  T  V  K  E  M  C  A  A  A  S  M  K  P  G

M  T  Y  R  P  D  C  L  A  L  F  L  G  L  Y  V  V  T  G  L  F  G  I  T  L  S  Y  H  R  Q  L  S  H  R  S  F  T  T  P  K
      ATGACATACAGGCCTGATTGTTGGCTTTGTTTTTGGGATTGTACGTGGTCACTGGACTATTTGGTATCAGGCTGTCATACCATCGTCAGCTGTCGCACAGGTCCTTCACGACACCGAAA  240
      ++++|++++|++++|++++|++++|++++|++++|++++|++++|++++|++++|++++|++++|++++|++++|++++|++++|++++|++++|++++|++++|++++|++++|++++|
      TACTGTATGTCCGGACTAACAAACCGAAACAAAAACCCTAACATGCACCAGTGACCTGATAAACCATAGTGCGACAGTATGGTAGCAGTCGACAGCGTGTCCAGGAAGTGCTGTGGCTTT
         M  V  Y  L  G  S  Q  K  A  K  N  K  P  N  Y  T  T  V  P  S  N  P  I  V  S  D  Y  W  R  .  S  D  C  L  D  K  V  V  G  F

W  L  E  Y  I  F  A  Y  C  G  V  L  A  F  Q  G  D  P  L  E  W  V  C  S  H  R  Y  H  H  Q  Y  C  E  T  D  R  D  P  H  S
      TGGTTGGAATACATCTTCGCTTATTGTGGAGTCTTGGCATTCCAGGGTGATCCTCTGGAATGGGTGTGCTCTCACAGGTATCATCACCAATATTGCGAGACAGATCGTGATCCCCACTCT  360
      ++++|++++|++++|++++|++++|++++|++++|++++|++++|++++|++++|++++|++++|++++|++++|++++|++++|++++|++++|++++|++++|++++|++++|++++|
      ACCAACCTTATGTAGAAGCGAATAACACCTCAGAACCGTAAGGTCCCACTAGGAGACCTTACCCACAGAGAGTGTCCATAGTAGTGGTTATAACGCTCTGTCTAGCACTAGGGGTGAGA
         H  N  S  Y  M  K  A  .  Q  P  T  K  A  N  W  P  S  G  R  S  H  T  H  E  .  L  Y  .  .  W  Y  Q  S  V  S  R  S  G  W  E

V  N  E  G  F  W  W  S  H  M  G  W  L  L  D  H  Q  A  T  K  T  R  T  G  D  Q  T  N  S  M  D  I  M  N  D  P  F  Y  S  F
      GTCAATGAAGGATTCTGGTGGTCTCATATGGGATGGTTGCTTGACCACCAGGCAACAAAGACACGGACTGGAGACCAGACTAACTCCATGGACATCATGAACGACCCTTTCTACAGCTTC  480
      ++++|++++|++++|++++|++++|++++|++++|++++|++++|++++|++++|++++|++++|++++|++++|++++|++++|++++|++++|++++|++++|++++|++++|++++|
      CAGTTACTTCCTAAGACCACCAGAGTATACCCTACCAACGAACTGGTGGTCCGTTGTTTCTGTGCCTGACCTCTGGTCTGATTGAGGTACTGTAGTACTTGCTGGGAAAGATGTCGAAG
         T  L  S  P  N  Q  H  D  .  I  P  H  N  S  S  W  W  A  V  F  V  R  V  P  S  W  V  L  E  M  S  M  M  F  S  G  K  .  L  K

I  K  K  T  Y  P  L  H  L  A  L  F  A  L  A  L  Y  A  W  G  G  I  P  Y  L  V  .  T  .  .  P
      ATCAAGAAGACCTATCCTTTGCATTTGGCGCTGTTTGCCCTGGCCCTCTATGCCTGGGGTGGCATTCCGTATTTGGTATAAACATGATGACC  572
      ++++|++++|++++|++++|++++|++++|++++|++++|++++|++++|++++|++++|++++|++++|++++|++++|++++|++++|++
      TAGTTCTTCTGGATAGGAAACGTAAACCGCGACAAACGGGACCGGGAGATACGGACCCCACCGTAAGGCATAAACCATATTTGTACTACTGG
         M  L  F  V  .  G  K  C  K  A  S  N  A  R  A  R  .  A  Q  P  P  M  G  Y  K  Y  Y  Y  R  N  G
```

| FIGURE LEGEND: | (SEQ ID NO:3 Translation)<br>(SEQ ID NO:3)<br>\|\|\|\|\|\|\|\|\|\|\|\|\|\|\|\|\|\|\|\|\|\|\|\|\|\|\|\|\|\|<br>(SEQ ID NO:3 Reverse Complement)<br>(SEQ ID NO:3 Reverse Complement Translation) |
|---|---|

Figure 6A

```
                10              20              30              40
  1   M G K G G D G G A Q A V S G T D A S L - - - - A E V S S V D S K S V H V V L Y G    SEQ ID NO:22 (Pavlova lutheri).pro
  1   M G R G G D S S G Q A H P A A E L A V P S D R A E V S N A D S K A L H I V L Y G    SEQ ID NO:62 (Pavlova salina).pro
  1   M K - - - - S - K R Q A L P - - - - - - - - - - - - - - - - - - - - - L T I D      SEQ ID NO:20 (Euglena gracilis).pro
  1   M S - - - - T L D R Q S I F T I K E L E S I S Q R I H D G D E E A M K F I I I D    SEQ ID NO:61 (Rhizopus stolonifer).pro
  1   M S - - - - T L D R Q S I F T I K E L E S I S Q R I H D G D E E A M K F I I I D    SEQ ID NO:49 (Rhizopus stolonifer).pro 50              60              70              80
 37   K R V - D V T K F Q K A H P G G S K V F R I F Q E R D A T E Q F E S Y H S P K A    SEQ ID NO:22 (Pavlova lutheri).pro
 41   K R V - D V T K F Q R T H P G G S K V F R I F Q D R D A T E Q F E S Y H S K R A    SEQ ID NO:62 (Pavlova salina).pro
 14   G T T Y D V S A W V N F H P G G A E I I E N Y Q G R D A T D A F M V M H S Q E A    SEQ ID NO:20 (Euglena gracilis).pro
 37   K K V Y D V T E F I E D H P G G A Q V L L T H V G K D A S D V F H A M H P E S A    SEQ ID NO:61 (Rhizopus stolonifer).pro
 37   K K V Y D V T E F I E D H P G G A Q V L L T H V G K D A S D V F H A M H P E S A    SEQ ID NO:49 (Rhizopus stolonifer).pro 90             100             110             120
 76   I K M M E G M L K K S E D A P A S V P L P S R S T M G T E F K E M I E R H K R A    SEQ ID NO:22 (Pavlova lutheri).pro
 80   I K M M E G M L K K S E D A P A D T P L P S Q S P M G K D F K A M I E R H V A A    SEQ ID NO:62 (Pavlova salina).pro
 54   F D K L K R - M P K I N P S S E L P P Q A A V N E A Q E D F R K L R E E L I A T    SEQ ID NO:20 (Euglena gracilis).pro
 77   Y E V L N N Y F V G D V Q E T V V T E K S S S A Q F A V E M R Q L R D Q L K K E    SEQ ID NO:61 (Rhizopus stolonifer).pro
 77   Y E V L N N Y F V G D V Q E T V V T E K S S S A Q F A V E M R Q L R D Q L K K E    SEQ ID NO:49 (Rhizopus stolonifer).pro 130             140             150             160
116   G L Y D P C P L D E L F K L T I V L A P I F V G A Y L V - - - - R S G V - S P L    SEQ ID NO:22 (Pavlova lutheri).pro
120   G Y Y D P C P L D E L F K L S L V L L P T F A G M Y M L - - - - K A G V G S P L    SEQ ID NO:62 (Pavlova salina).pro
 93   G M F D A S P L W Y S Y K I S T T L G L G V L G Y F L M V Q Y Q M - - - - - Y F    SEQ ID NO:20 (Euglena gracilis).pro
117   G Y F H S S K L F Y A Y K V L S T L A I C I A G L S P L Y A Y G R T S T L A V V    SEQ ID NO:61 (Rhizopus stolonifer).pro
117   G Y F H S S K L F Y A Y K V L S T L A I C I A G L S L L Y A Y G R T S T L A V V    SEQ ID NO:49 (Rhizopus stolonifer).pro 170             180             190             200
151   A G A L S M G F G F Y L D G W L A H D Y L H H A V F K G S V N T L V K A N N A M    SEQ ID NO:22 (Pavlova lutheri).pro
156   C G A L M V S F G W Y L D G W L A H D Y L H H S V F K G S V A R T V G W N N A A    SEQ ID NO:62 (Pavlova salina).pro
128   I G A V L L G M H Y Q Q M G W L S H D I C H H Q T F K N R - - - - - N W N N L V    SEQ ID NO:20 (Euglena gracilis).pro
157   A S A I T V G I F W Q Q C G W L A H D F G H H Q C F E D R - - - - - T W N D V L    SEQ ID NO:61 (Rhizopus stolonifer).pro
157   A S A I T V G I F W Q Q C G W L A H D F G H H Q C F E D R - - - - - T W N D V L    SEQ ID NO:49 (Rhizopus stolonifer).pro 210             220             230             240
191   G Y A L G - F L Q G Y D V A W W R A R H N T H H V C T N E D G S D P D I K T A P    SEQ ID NO:22 (Pavlova lutheri).pro
196   G Y F L G - F V Q G Y A V E W W R A R H N T H H V C T N E D G S D P D I K T A P    SEQ ID NO:62 (Pavlova salina).pro
163   G L V F G N L Q G F S V T W W K D R H N A H H S A T N V Q G H D P D I D N L P      SEQ ID NO:20 (Euglena gracilis).pro
192   V V F L G N F C Q G F S L S W W K N K H N T H H A S T N V H G Q D P D I D T A P    SEQ ID NO:61 (Rhizopus stolonifer).pro
192   V V F L G N F C Q G F S L S W W K N K H N T H H A S T N V H G Q D P D I D T A P    SEQ ID NO:49 (Rhizopus stolonifer).pro
```

Figure 6B

```
                    250           260           270           280
230  L L I Y - - - - - - - - - - - V R E N P S I A K R L - - - N F F Q R W Q Q Y Y Y   SEQ ID NO:22 (Pavlova lutheri).pro
235  L L I Y - - - - - - - - - - - V R N K P S I A K R L - - - N A F Q R Y Q Q Y Y Y   SEQ ID NO:62 (Pavlova salina).pro
203  L L A W S E - - - - - - - D D V T R A S P I S R K L I Q F Q - - - - - - Q Y Y F   SEQ ID NO:20 (Euglena gracilis).pro
232  V L L W D E Y A S A A Y Y A S L D Q E P T M V S R F L A E Q V L P H Q T R Y F F   SEQ ID NO:61 (Rhizopus stolonifer).pro
232  V L L W D E Y A S A A Y Y A S L D Q E P T M V S R F L A E Q V L P H Q T R Y F F   SEQ ID NO:49 (Rhizopus stolonifer).pro 290           300           310           320
256  V P T M A I L D L Y W R L E S I A Y V A V R - - L P K M W M Q A A - - - - - - -   SEQ ID NO:22 (Pavlova lutheri).pro
261  V P V M A I L D L Y W R L E S I A Y V A M R - - L P K M L P Q A L - - - - - - -   SEQ ID NO:62 (Pavlova salina).pro
230  L V I C I L L R F I W C F Q S V - - - L T V R S L - K D R D N Q F Y R S Q Y K K   SEQ ID NO:20 (Euglena gracilis).pro
272  F I L - A F A R L S W A L Q S L S Y S F K K E S I N K S R Q L N L F - - - - - -   SEQ ID NO:61 (Rhizopus stolonifer).pro
272  F I L - A F A R L S W A L Q S L S Y S F K K E S I N K S R Q L N L F - - - - - -   SEQ ID NO:49 (Rhizopus stolonifer).pro 330           340           350           360
287  - - - - - - - - - - A L A A H Y A L L C W V F A A H L N L I P L M M - - V A R G F   SEQ ID NO:22 (Pavlova lutheri).pro
292  - - - - - - - - - - A L V A H Y A I V A W V F A G N Y H L L P L V T - - V L R G F   SEQ ID NO:62 (Pavlova salina).pro
266  E A I G L A L H W T L K T L F H L F - F M P S I L T S L L V F F V S E L V G G F   SEQ ID NO:20 (Euglena gracilis).pro
305  E R V C I V G H W A L S A - F C I Y S W C S N V Y H M V L F F L V S Q A T T G Y   SEQ ID NO:61 (Rhizopus stolonifer).pro
305  E R V C I V G H W A L F A - F C I Y S W C S N V Y H M V L F F L V S Q A T T G Y   SEQ ID NO:49 (Rhizopus stolonifer).pro 370           380           390           400
316  A T G I V V F A T H Y G E D I L D R E H V E G M T L V E Q T A K T S R N I T G G   SEQ ID NO:22 (Pavlova lutheri).pro
321  G T G I T V F A T H Y G E D I L D A D Q V R H M T L V E Q T A L T S R N I S G G   SEQ ID NO:62 (Pavlova salina).pro
305  G I A I V V F M N H Y P L E K I G D S V W D G H G F S V G Q I H E T M N I R R G   SEQ ID NO:20 (Euglena gracilis).pro
344  T L A L V F A L N H N G M P V I T E E K A E S M E F F E I Q V I T G R D V T L S   SEQ ID NO:61 (Rhizopus stolonifer).pro
344  T L A L V F A L N H N G M P V I T E E K A E S M E F F E I Q V I T G R D V T L S   SEQ ID NO:49 (Rhizopus stolonifer).pro 410           420           430           440
356  W L V N V L T G F I S L Q T E H H L F P M M P T G N L M T I Q P E V R D F F K K   SEQ ID NO:22 (Pavlova lutheri).pro
361  W L V N V L T G F I S L Q T E H H L F P M M P T G N L M T I Q P E V R A F F K K   SEQ ID NO:62 (Pavlova salina).pro
345  I I T D W F F G G L N Y Q I E H H L W P T L P R H N L T A V S Y Q V E Q L C Q K   SEQ ID NO:20 (Euglena gracilis).pro
384  P L G D W F M G G L N Y Q I E H H V F P N M P R H N L P T V K P M V K S L C Q K   SEQ ID NO:61 (Rhizopus stolonifer).pro
384  P L G D W F M G G L N Y Q I E H H V F P N M P R H N L P T V K P M V K S L C Q K   SEQ ID NO:49 (Rhizopus stolonifer).pro 450           460           470
396  H G L E Y R E G N L F Q C V H Q N I K A L A F E H L L H                             SEQ ID NO:22 (Pavlova lutheri).pro
401  H G L E Y R E G N L I E C V R Q N I R A L A F E H L L                               SEQ ID NO:62 (Pavlova salina).pro
385  H N L P Y R N P L P H E G L V I L L R Y L A V F A R M A E K Q P A G K A L           SEQ ID NO:20 (Euglena gracilis).pro
424  Y D I N Y H D T G F L K G T L E V L Q T L D I T S K L S L - Q L S K K S F           SEQ ID NO:61 (Rhizopus stolonifer).pro
424  Y D I N Y H D T G F L K G T L E V L Q T L D I T S K L S L - Q L S K K S F           SEQ ID NO:49 (Rhizopus stolonifer).pro
```

Δ-9 DESATURASE AND ITS USE IN MAKING POLYUNSATURATED FATTY ACIDS

FIELD OF THE INVENTION

This invention is in the field of biotechnology. More specifically, this invention pertains to the identification of nucleic acid fragments encoding a Δ9 fatty acid desaturase enzyme and the use of this desaturase for synthesis of palmitoleic (16:1) and oleic (18:1) fatty acids, which can be subsequently converted to long chain polyunsaturated fatty acids (PUFAs).

BACKGROUND OF THE INVENTION

The importance of PUFAs is undisputed. For example, certain PUFAs are important biological components of healthy cells and are considered: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs has cardiovascular protective effects (Dyerberg, J. et al., *Amer. J. Clin. Nutr.*, 28:958-966 (1975); Dyerberg, J. et al., *Lancet*, 2(8081):117-119 (Jul. 15, 1978); Shimokawa, H., *World Rev. Nutr. Diet*, 88:100-108 (2001); von Schacky, C. and Dyerberg, J., *World Rev. Nutr. Diet*, 88:90-99 (2001)). Numerous other studies document wide-ranging health benefits conferred by administration of ω-3 and/or ω-6 PUFAs against a variety of symptoms and diseases (e.g., asthma, psoriasis, eczema, diabetes, cancer).

A variety of different hosts including plants, algae, fungi and yeast are being investigated as means for commercial PUFA production. Genetic engineering has demonstrated that the natural abilities of some hosts can be substantially altered to produce various long-chain ω-3/ω-6 PUFAs, e.g., arachidonic acid (ARA; 20:4 ω-6), eicosapentaenoic acid (EPA; 20:5 ω-3) and docosahexaenoic acid (DHA; 22:6 ω-3). Whether ω-3/ω-6 PUFA production is the result of natural abilities or recombinant technology, however, both strategies may benefit from methods that increase carbon flow into lipid metabolism.

Lipid metabolism in most organisms is catalyzed by a multi-enzyme fatty acid synthase (FAS) complex and initially occurs by the condensation of eight 2-carbon fragments (acetyl groups from acetyl-CoA) to form palmitate, a 16-carbon saturated fatty acid (Smith, S. *FASEB J.*, 8(15):1248-59 (1994)). Once free palmitate (16:0) is released from FAS, the molecule undergoes either elongation (i.e., via a $C_{16/18}$ fatty acid elongase to produce stearic acid (18:0)) or unsaturation (i.e., via a Δ9 desaturase to produce palmitoleic acid (16:1)). The primary fate of palmitate is elongation, while desaturation is only a minor reaction in most organisms. As such, significant cellular pools of stearic acid become available for conversion to oleic acid (18:1) via a Δ9 desaturase. Oleic acid is the primary metabolic precursor of all other fatty acid molecules. Based on the above, it is concluded that Δ9 desaturases affect overall carbon flux into the fatty acid biosynthetic pathway, and thereby play a determinant role in both the quantity and composition of oil so produced.

Based on the role Δ9 desaturase enzymes play to thereby effectively "push" carbon into the PUFA biosynthetic pathway, there has been considerable effort to identify and characterize these enzymes from various sources. For example, the genes encoding Δ9 desaturase have been cloned from several fungi and yeast, including: *Saccharomyces cerevisiae* (Stukey J. E. et al., *J Biol. Chem.*, 265(33):20144-20149 (1990)); the oleaginous yeast *Cryptococcus curvatus* CBS 570 (Meesters, P. A. and G. Eggink, *Yeast*, 12(8):723-730 (1996)); *Saccharomyces kluyveri* (GenBank Accession No. AB071696; Kajiwara S., *FEMS Yeast Res.*, 2(3):333-339 (2002)); *Mortierella alpina* (U.S. Pat. No. 6,448,055); and *Aspergillis nidulans* (U.S. Pat. No. 6,495,738). And, expression of some of these Δ9 desaturases in non-native host organisms has been shown to increase the level of palmitoleic acid, oleic acid and derivatives thereof (e.g., U.S. Pat. No. 6,448,055). Despite this, there is need for the identification and isolation of additional genes encoding Δ9 desaturases that will be suitable for heterologous expression in a variety of host organisms for use in the production of PUFAs.

There are no reports to date concerning the isolation of a Δ9 desaturase from an euglenoid. Although there are over 100 species described within the genus of euglenoids known as *Euglena, E. gracilis* is best studied. Several other investigators have studied the PUFA biosynthetic pathway within this organism, leading to the isolation of the organism's Δ8 desaturase and Δ4 desaturase; however, no one has identified the gene encoding Δ9 desaturase within *Euglena gracilis*.

Applicants have solved the stated problem by isolating the gene encoding Δ9 desaturase from *Euglena gracilis* and demonstrating increased conversion of 18:0 to 18:1 upon overexpression of the gene in the oleaginous yeast, *Yarrowia lipolytica*. This will enable increased PUFA content in the host oil and increased oil biosynthesis, upon co-expression with other PUFA biosynthetic pathway genes.

SUMMARY OF THE INVENTION

The present invention relates to new genetic constructs encoding polypeptides having Δ9 desaturase activity, and their use in plants, algae, bacteria, yeast, euglenoids and fungi for the production of PUFAs.

Accordingly the invention provides an isolated nucleic acid molecule comprising:

a.) an isolated nucleotide sequence encoding a ☐9 desaturase enzyme as set forth in SEQ ID NO:2;

b.) an isolated nucleotide sequence that hybridizes with (a) under the following hybridization conditions: 0.1×SSC, 0.1% SDS, 65° C. and washed with 2×SSC, 0.1% SDS followed by 0.1×SSC, 0.1% SDS; or c.) an isolated nucleotide sequence that is completely complementary to (a) or (b).

In another embodiment the invention provides an isolated nucleic acid molecule comprising a first nucleotide sequence encoding a Δ9 desaturase enzyme of at least 340 amino acids that has at least 90% identity based on BLASTP algorithms when compared to a polypeptide having the sequence as set forth in SEQ ID NO:2;

or a second nucleotide sequence comprising the complement of the first nucleotide sequence.

Similarly the invention provides polypeptides encoded by the nucleotide sequences of the invention as well as genetic chimera and host cells comprising the same.

In another embodiment the invention provides a method for the production of oleic acid comprising:
a.) providing a host cell comprising:
   i) an isolated nucleotide molecule encoding a Δ9 desaturase polypeptide of the invention; and,
   (ii) a source of stearic acid; and
b.) growing the host cell of step (a) under conditions wherein the nucleic acid molecule encoding the Δ9 desaturase polypeptide is expressed and the stearic acid is converted to oleic acid.

In an alternate embodiment the invention provides A method for the production of palmitoleic acid comprising:
a.) providing a host cell comprising:
   i) an isolated nucleotide molecule encoding a Δ9 desaturase polypeptide of the invention; and,
   (ii) a source of palmitic acid;
b.) growing the host cell of step (a) under conditions wherein the nucleic acid molecule encoding the Δ9 desaturase polypeptide is expressed and the palmitic acid is converted to palmitoleic acid.

BRIEF DESCRIPTION OF THE DRAWINGS AND SEQUENCE LISTINGS

FIG. 3 shows a portion of an alignment between and among Δ5 desaturase proteins and Δ8 desaturase proteins using a ClustalW analysis (MegAlign™ program of DNASTAR software).

FIG. 4 shows SEQ ID NO:3 (the 572 bp fragment of pT-F4-1), a translation of SEQ ID NO:3, the reverse complement of SEQ ID NO:3 and the translated reverse complement of SEQ ID NO:3. Regions shown in gray boxes correspond to the first 6 amino acids of Conserved Region 1 (SEQ ID NO:23).

Figure 5:
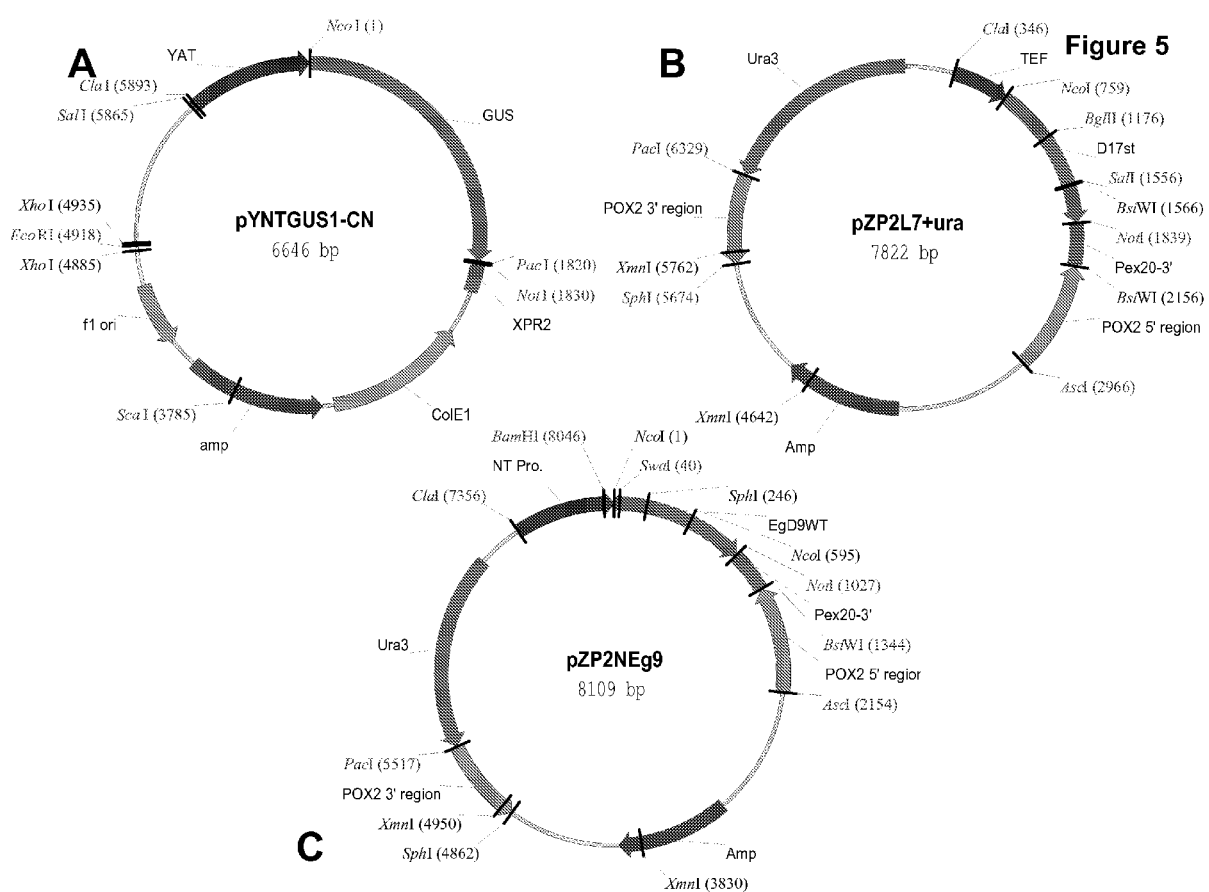

FIG. 5 provides plasmid maps for the following: (A) pNT-GUS1-CN; (B) pZP2L7+ura; and (C) pZP2NEg9.

FIGS. 6A and 6B show a Clustal V alignment (with default parameters) of a *Pavlova lutheri* Δ8 desaturase (SEQ ID NO:22), a *Pavlova salina* Δ8 desaturase (SEQ ID NO:62), a *Euglena gracilis* Δ8 desaturase (SEQ ID NO:20) and two different *Rhizopus stolonifer* Δ6 fatty acid desaturases (SEQ ID NOs:49 and 61).

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith and is filed electronically. The Sequence Listing is hereby incorporated by reference in compliance with 37 CFR 1.52(e). The Sequence listing file has the following size: 103,325 bytes and which was created Dec. 20, 2006.

SEQ ID NOs:1-12, 16-24, 33, 34, 45-47, 49-52 and 59-63 are ORFs encoding genes, proteins or plasmids, as identified in Table 1.

TABLE 1

Summary Of Gene And Protein SEQ ID Numbers

| Description and Abbreviation | Nucleic acid SEQ ID NO. | Protein SEQ ID NO. |
|---|---|---|
| *Euglena gracilis* Δ9 desaturase ("EgD9") | 1 (1023 bp) | 2 (340 AA) |
| *Euglena gracilis* EgD9-fragment of pT-F4-1 | 3 (572 bp) | 4 (186 AA) |
| *Euglena gracilis* EgD9-fragment of pT-EgD9-5'C2 | 5 (653 bp) | — |
| *Euglena gracilis* EgD9-5' sequence relative to SEQ ID NO: 3 (obtained from pT-EgD5-5'C2) | 6 (266 bp) | — |
| *Euglena gracilis* EgD9-5' coding region of SEQ ID NO: 6 | 7 (150 bp) | — |
| *Euglena gracilis* EgD9-5' untranslated region of SEQ ID NO: 6 | 8 (116 bp) | — |
| *Euglena gracilis* EgD9-fragment of pT-EgD9-3' | 9 (660 bp) | — |
| *Euglena gracilis* EgD9-3' sequence relative to SEQ ID NO: 3 (obtained from pT-EgD9-3') | 10 (543 bp) | — |
| *Euglena gracilis* EgD9-3' coding region of SEQ ID NO: 10 | 11 (300 bp) | — |
| *Euglena gracilis* EgD9-3' untranslated region of SEQ ID NO: 10 | 12 (243 bp) | — |
| *Euglena gracilis* EgD9-assembled contig | 63 (1382 bp) | — |
| *Phaeodactylum tricornutum* Δ5 desaturase (GenBank Accession No. AAL92562) | — | 16 (469 AA) |
| *Phytophthora megasperma* Δ5 desaturase (GenBank Accession No. CAD53323) | — | 17 (477 AA) |
| *Pythium irregulare* Δ5 desaturase (GenBank Accession No. AAL13311) | — | 18 (456 AA) |
| *Dictyostelium discoideum* Δ5 desaturase (GenBank Accession No. XP_640331) | — | 19 (467 AA) |
| *Euglena gracilis* Δ8 desaturase (PCT Publications No. WO 2006/012325 and No. WO 2006/012326) | — | 20 (421 AA) |
| *Pavlova lutheri* (CCMP459) Δ8 desaturase | 21 (1269 bp) | 22 (423 AA) |
| Conserved Region 1 | — | 23 (7 AA) |
| Conserved Region 2 | — | 24 (7 AA) |
| *Arabidopsis thaliana* putative Δ9 desaturase (GenBank Accession No. AAN41357) | — | 33 (371 AA) |
| *Picea glauca* Δ9 desaturase (GenBank Accession No. AAM12238) | — | 34 (382 AA) |
| Plasmid pYNTGUS1-NC | 45 (6646 bp) | — |
| Plasmid pZP2L7 + Ura | 46 (7483 bp) | — |
| Plasmid pZP2NEg9 | 47 (8109 bp) | — |
| *Rhizopus stolonifer* Δ6 fatty acid desaturase (NCBI Accession No. AAX22052) | — | 49 (459 AA) |
| *Pavlova lutheri* Δ8 desaturase-portion of cDNA insert from clone eps1c.pk002.f22 (5' end of cDNA insert) | 50 (695 bp) | — |
| *Pavlova lutheri* Δ8 desaturase-fully sequenced EST eps1c.pk002.f22:fis (full insert sequence) | 51 (1106 bp) | — |
| *Pavlova lutheri* Δ8 desaturase-translation of nucleotides 1-864 of fully sequenced EST eps1c.pk002.f22:fis (full insert sequence; SEQ ID NO: 51) | — | 52 (287 AA) |
| *Pavlova lutheri* Δ8 desaturase-full 5' end sequence from genome walking | 59 (1294 bp) | — |
| *Pavlova lutheri* Δ8 desaturase-assembled sequence | 60 (1927 bp) | — |
| *Rhizopus stolonifer* Δ6 fatty acid desaturase (NCBI Accession No. ABB96724) | — | 61 (459 AA) |
| *Pavlova salina* Δ8 desaturase | — | 62 (427 AA) |

SEQ ID NOs:13-15 corresponds to primers AP, SMART™ IV oligonucleotide and CDSIII 5' primer, used for cDNA synthesis from *Euglena gracilis* mRNA.

SEQ ID NOs:25-28 correspond to degenerate oligonucleotide primers 5-1A, 5-1B, 5-1C and 5-1D, respectively, that encode Conserved Region 1.

SEQ ID NOs:29-32 correspond to degenerate oligonucleotide primers 5-4AR, 5-4BR, 5-4CR and 5-4DR, respectively, that encode Conserved Region 2.

SEQ ID NOs:35-37 correspond to primers Eg9-5'1, Eg9-5'2 and DNR CDS 5, respectively, used for 5' RACE.

SEQ ID NOs:38-40 correspond to primers Eg9-3'1, AUAP and Eg9-3'2, respectively, used for 3' RACE.

SEQ ID NOs:41-44 correspond to primers YL837, YL838, YL839 and YL840, respectively, used for amplification of the full length cDNA of EgD9.

SEQ ID NO:48 corresponds to primer T7, used for sequencing the *Pavlova lutheri* (CCMP459) cDNA library.

SEQ ID NOs:53 and 54 correspond to primers SeqE and SeqW, respectively, used for sequencing *Pavlova lutheri* (CCMP459) clones.

SEQ ID NOs:55 and 56 correspond to the Universal GenomeWalker™ primer AP1 and primer GSP PvDES, respectively, used for amplification of genomic *Pavlova lutheri* (CCMP459) DNA.

SEQ ID NOs:57 and 58 correspond to primers M13-28Rev and PavDES seq, respectively, used for sequencing *Pavlova lutheri* (CCMP459) genomic inserts.

DETAILED DESCRIPTION OF THE INVENTION

All patents, patent applications, and publications cited herein are incorporated by reference in their entirety. This specifically includes the following commonly owned and co-pending applications: U.S. patent application Ser. No. 10/840,478, No. 10/840,579 and No. 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. No. 10/985,109 and No. 10/985,691 (filed Nov. 10, 2004), U.S. patent application Ser. No. 10/987,548 (filed Nov. 12, 2004), U.S. patent application Ser. No. 11/024,545 and No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/251,466 (filed Oct. 14, 2005), U.S. patent application Ser. No. 11/254,173 and No. 11/253,882 (filed Oct. 19, 2005), U.S. patent application Ser. No. 11/264,784 and No. 11/264,737 (filed Nov. 1, 2005), U.S. patent application Ser. No. 11/265,761 (filed Nov. 2, 2005), U.S. Patent Application No. 60/795,810 (filed Apr. 28, 2006), U.S. Patent Application No. 60/793,575 (filed Apr. 20, 2006), U.S. Patent Application No. 60/796,637 (filed May 2, 2006), U.S. Patent Application No. 60/801,172 (filed May 17, 2006), U.S. Patent Application No. 60/801,119 (filed May 17, 2006), U.S. Patent Application No. 60/853,563 (filed Oct. 23, 2006), U.S. Patent Application No. 60/855,177 (filed Oct. 30, 2006), U.S. patent application Ser. No. 11/601,564 (filed Nov. 16, 2006) and U.S. patent application Ser. No. 11/635,258 (filed Dec. 7, 2006).

The present invention provides a *Euglena gracilis* Δ9 desaturase enzyme and gene encoding the same that may be used for the manipulation of biochemical pathways for the production of healthful PUFAs.

PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into e.g., cooking oils, fats or margarines formulated so that in normal use the recipient would receive the desired amount for dietary supplementation. PUFAs may also be used as anti-inflammatory or cholesterol lowering agents as components of pharmaceutical or veterinary compositions.

DEFINITIONS

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and each compounds' chemical name.

TABLE 2

Nomenclature of Polyunsaturated Fatty Acids And Precursors

| Common Name | Abbreviation | Chemical Name | Shorthand Notation |
| --- | --- | --- | --- |
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |

TABLE 2-continued

Nomenclature of Polyunsaturated Fatty Acids And Precursors

| Common Name | Abbreviation | Chemical Name | Shorthand Notation |
|---|---|---|---|
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell. "Microbial oils" or "single cell oils" are those oils naturally produced by microorganisms during their lifespan.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidylethanolamine (PE) fraction and triacylglycerol (TAG or oil) fraction. However, the terms "lipid" and "oil" will be used interchangeably throughout the specification.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publication No. WO 2006/052870). Briefly, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulum membrane. More specifically, "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

Figure 1:
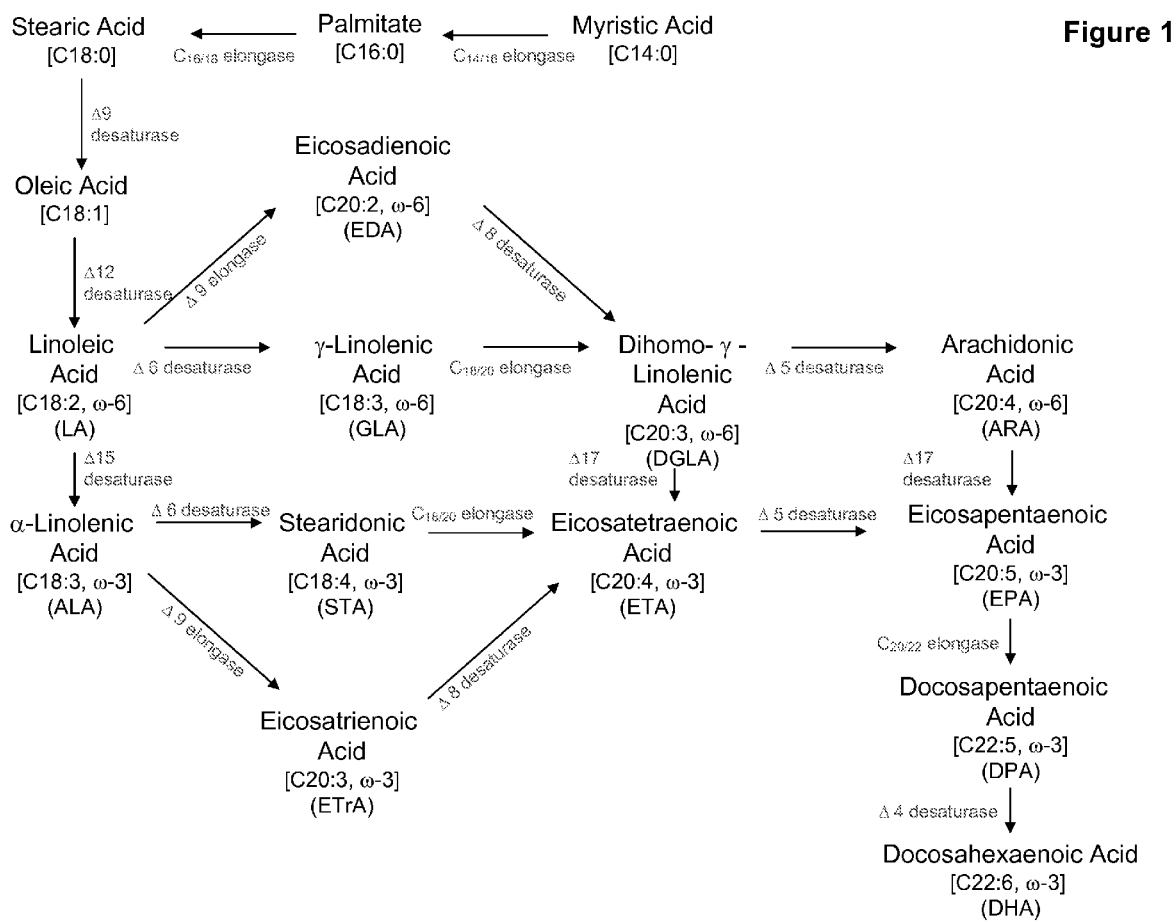
FIG. 1 illustrates the ω-3/ω-6 fatty acid biosynthetic pathway.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the PUFA biosynthetic pathway enzyme genes are required, as a number of fatty acid products will only require the expression of a subset of the genes of this pathway.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ9 desaturases that catalyze the conversion of palmitate to palmitoleic acid (16:1) and/or stearate to oleic acid (18:1). Other desaturases include, for example: 1.) Δ8 desaturases that will catalyze the conversion of EDA to DGLA and/or ETrA to ETA; 2.) Δ5 desaturases that catalyze the conversion of DGLA to ARA and/or ETA to EPA; 3.) Δ6 desaturases that catalyze the conversion of LA to GLA and/or ALA to STA; 4.) Δ4 desaturases that catalyze the conversion of DPA to DHA; 5.) Δ12 desaturases that catalyze the conversion of oleic acid to LA; 6.) Δ15 desaturases that catalyze the conversion of LA to ALA and/or GLA to STA; and 7.) Δ17 desaturases that desaturate a fatty acid between the $17^{th}$ and $18^{th}$ carbon atom numbered from the carboxyl-terminal end of the molecule and which, for example, catalyze the conversion of ARA to EPA (and optionally DGLA to ETA). In the art, Δ15 and Δ17 desaturases are also occasionally referred to as "omega-3 desaturases", "w-3 desaturases" and/or "ω-3 desaturases", based on their ability to convert ω-6 fatty acids into their ω-3 counterparts (e.g., conversion of LA into ALA, GLA into STA, DGLA into ETA and/or ARA into EPA, respectively).

Some desaturases have activities on two or more substrates (e.g., the substrates of the *Saprolegnia diclina* Δ17 desaturase include ARA and DGLA and those of the *Caenorhabditis elegans* ω-3 desaturase include LA and GLA). In some embodiments, it is most desirable to empirically determine the specificity of a fatty acid desaturase by transforming a suitable host with the gene for the fatty acid desaturase and determining its effect on the fatty acid profile of the host.

For the purposes herein, the term "EgD9" refers to a Δ9 desaturase enzyme (SEQ ID NO:2) isolated from *Euglena gracilis* encoded by SEQ ID NO:1.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, as described in PCT Publication No. WO 2004/101757. Examples of reactions catalyzed by elongase systems are the conversion of GLA to DGLA, STA to ETA and EPA to DPA. In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase (also known as a Δ6 elongase as the terms can be used interchangeably) will utilize a $C_{18}$ substrate (e.g., GLA, STA) and a $C_{20/22}$ elongase will utilize a $C_{20}$ substrate (e.g., EPA). In like manner, a Δ9 elongase is able to catalyze the conversion of LA and ALA to EDA and ETrA, respectively. It is important to note that some elongases have broad specificity and thus a single enzyme may be capable of catalyzing several elongase reactions (e.g., thereby acting as both a $C_{16/18}$ elongase and a $C_{18/20}$ elongase). In preferred embodiments, it is desirable to empirically determine the specificity of a fatty acid elongase by transforming a suitable host with the gene for the fatty acid elongase and determining its effect on the fatty acid profile of the host.

The term "oleaginous" refers to those organisms that tend to store their energy source in the form of lipid (Weete, In: Fungal Lipid Biochemistry, $2^{nd}$ Ed., Plenum, 1980). The term "oleaginous yeast" refers to those microorganisms classified as yeasts that can make oil. Generally, the cellular oil or TAG content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Euglena, Eutreptiella* and *Tetruetreptia*.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The term "plant organ" refers to plant tissue or a group of tissues that constitute a morphologically and functionally distinct part of a plant. The term "genome" refers to the following: (1) the entire complement of genetic material (genes and non-coding sequences) that is present in each cell of an organism, or virus or organelle; and/or (2) a complete set of chromosomes inherited as a (haploid) unit from one parent.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

"Progeny" comprises any subsequent generation of a plant.

The term "genome" refers to the following: (1) the entire complement of genetic material (genes and non-coding sequences) is present in each cell of an organism, or virus or organelle; (2) a complete set of chromosomes inherited as a (haploid) unit from one parent.

As used herein, an "isolated nucleic acid fragment" or "isolated nucleic acid molecule" will be used interchangeably and refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular euglenoid proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The terms "homology" and "homologous" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences encompassed by this invention are also defined by their ability to hybridize, under moderately stringent conditions (e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequences" and "transcription terminator" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; PCT Publication No. WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragments of the invention. Expression may also refer to translation of mRNA into a polypeptide.

"Mature" protein refers to a post-translationally processed polypeptide, i.e., one from which any pre- or propeptides present in the primary translation product have been removed. "Precursor" protein refers to the primary product of translation of mRNA, i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the Clustal method of alignment.

More specifically, the "Clustal W method of alignment" corresponds to the alignment method labeled Clustal W (described by Thompson et al., *Nucleic Acids Res.* 22:4673-4680

(1994)) and found in the MegAlign v5.07 program of the LASERGENE bioinformatics computing suite (DNASTAR Inc.). Default parameters for multiple alignments and calculation of percent identity of protein sequences are GAP PENALTY=10, GAP LENGTH PENALTY=0.2, DELAY DIVERGENCE SEQS (%)=30, DNA TRANSITION WEIGHT=0.50, protein weight matrix=Gonnet series and DNA weight matrix=IUB, unless otherwise specified. Default parameters for pairwise alignments and calculation of percent identity of protein sequences are GAP PENALTY=10, GAP LENGTH PENALTY=0.1, protein weight matrix=Gonnet 250 and DNA weight matrix=IUB, unless otherwise specified.

"BLASTP method of alignment" is an algorithm provided by the National Center for Biotechnology Information (NCBI) to compare protein sequences using default parameters.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Indeed, any integer amino acid identity from 70% to 100% may be useful in describing the present invention, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

An Overview: Microbial Biosynthesis of Fatty Acids and Triacylglycerols

Lipid metabolism is a basic metabolic process that almost all animals, plants and microorganisms possess; and thus, almost all of these organisms possess the ability to synthesize palmitate (16:0), stearic acid (18:0) and oleic acid (18:1) (since these fatty acids are essential for phospholipid biosynthesis). Uniquely, however, lipid accumulation in oleaginous microorganisms (in general) is triggered in response to the overall carbon to nitrogen ratio present in the growth medium. Although the process leading to the de novo synthesis of free palmitate (16:0) in oleaginous microorganisms is described in detail in PCT Publication No. WO 2004/101757, the formation of palmitate, stearic acid and oleic acid from myristic acid (14:0) is summarized in FIG. 1. Briefly, free palmitate is produced from myristic acid via an elongation reaction (i.e., catalyzed by a $C_{14/16}$ fatty acid elongase); subsequently, palmitate can be elongated by a $C_{16/18}$ fatty acid elongase to produce stearic acid or unsaturated by a Δ9 desaturase to produce palmitoleic acid (16:1)). Since the primary fate of palmitate is elongation, however, there is a significant pool of stearic acid in the organism that is available for subsequent desaturation by a Δ9 desaturase to result in oleic acid synthesis, the metabolic precursor of all PUFAs. As such, it is concluded that Δ9 desaturases affect overall carbon flux into the fatty acid biosynthetic pathway since these enzymes directly affect the amount of oleic acid produced in the organism.

The metabolic process wherein oleic acid is converted to ω-3/ω-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ6 desaturase/Δ6 elongase pathway", ω-6 fatty acids are formed as follows: (1) LA is converted to GLA by a Δ6 desaturase; (2) GLA is converted to DGLA by a $C_{18/20}$ elongase; and (3) DGLA is converted to ARA by a Δ5 desaturase. Alternatively, the "Δ6 desaturase/Δ6 elongase pathway" can be utilized for formation of ω-3 fatty acids as follows: (1) LA is converted to ALA, the first of the ω-3 fatty acids, by a Δ15 desaturase; (2) ALA is converted to STA by a Δ6 desaturase; (3) STA is converted to ETA by a $C_{18/20}$ elongase; (4) ETA is converted to EPA by a Δ5 desaturase; (5) EPA is converted to DPA by a $C_{20/22}$ elongase; and (6) DPA is converted to DHA by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ9 elongase and Δ8 desaturase. More specifically, LA and ALA may be converted to EDA and ETrA, respectively, by a Δ9 elongase; then, a Δ8 desaturase converts EDA to DGLA and/or ETrA to ETA.

It is contemplated that the particular functionalities required to be expressed in a specific host organism for production of ω-3/ω-6 fatty acids will depend on the host cell (and its native PUFA profile and/or desaturase/elongase profile), the availability of substrate, and the desired end product(s). One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, yeast, euglenoids, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, consideration of each enzyme's conversion efficiency must be considered in light of the final desired lipid profile of the product, when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

TAGs (the primary storage unit for fatty acids) are formed by a series of reactions that involve: 1.) the esterification of one molecule of acyl-CoA to glycerol-3-phosphate via an acyltransferase to produce lysophosphatidic acid; 2.) the esterification of a second molecule of acyl-CoA via an acyltransferase to yield 1,2-diacylglycerol phosphate (commonly identified as phosphatidic acid); 3.) removal of a phosphate by phosphatidic acid phosphatase to yield 1,2-diacylglycerol (DAG); and 4.) the addition of a third fatty acid by the action of an acyltransferase to form TAG. A wide spectrum of fatty acids can be incorporated into TAGs, including saturated and unsaturated fatty acids and short-chain and long-chain fatty acids.

Sequence Identification of a Novel *Euglena gracilis* Δ9 Desaturase

In the present invention, a nucleotide sequence has been isolated from *Euglena gracilis* encoding a Δ9 desaturase, designated herein as "EgD9".

Comparison of the EgD9 nucleotide base and deduced amino acid sequences to public databases reveals that the most similar known sequences are about 58% identical to the amino acid sequence of EgD9 reported herein over a length of 340 amino acids using BLASTP algorithms. More preferred amino acid fragments are at least about 70%-85% identical to the sequences herein, where those sequences that are at least about 85%-90% identical are particularly suitable and those sequences that are at least about 90%-95% identical are most preferred. Similarly, preferred EgD9 encoding nucleic acid sequences corresponding to the instant ORF are those encoding active proteins and which are at least about 70%-85% identical to the nucleic acid sequences of EgD9 reported herein, where those sequences that are at least about 85%-90% identical are particularly suitable and those sequences that are at least about 90%-95% identical are most preferred.

In alternate embodiments, the instant EgD9 desaturase sequence can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., desaturase activity can be synthesized in whole or in part using the codons preferred in the host species.

In one preferred embodiment of the invention herein, EgD9 could be codon-optimized for expression in *Yarrowia lipolytica*. This would be possible by using the *Y. lipolytica* codon usage profile (see PCT Publication No. WO 04/101757) and modifying the nucleotide sequence around the 'ATG' initiation codon such that it corresponded to the *Y. lipolytica* consensus sequence around the 'ATG' initiation codon. It is expected that the codon-optimized gene will be more efficient desaturating stearic acid to oleic acid than the wildtype gene, when expressed in *Y. lipolytica*.

One skilled in the art would be able to use the teachings herein to create various other codon-optimized Δ9 desaturase proteins suitable for optimal expression in alternate hosts (i.e., other than *Yarrowia lipolytica*) based on the wildtype EgD9 sequence provided herein. Accordingly, the instant invention relates to any codon-optimized Δ9 desaturase protein that is derived from the wildtype EgD9 (i.e., encoded by SEQ ID NO:2).

Identification and Isolation of Homologs

Any of the instant desaturase sequences (i.e., EgD9) or portions thereof may be used to search for Δ9 desaturase homologs in the same or other plants, algae, bacteria, yeast, euglenoid or fungi species using sequence analysis software. In general, such computer software matches similar sequences by assigning degrees of homology to various substitutions, deletions, and other modifications.

Alternatively, any of the instant desaturase sequences or portions thereof may also be employed as hybridization reagents for the identification of Δ9 homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ9 desaturase nucleic acid fragments described herein (or any homologs identified thereof) may be used to isolate genes encoding homologous proteins from the same or other plants, algae, bacteria, yeast, euglenoid or fungi species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA,* 82:1074 (1985); or strand displacement amplification (SDA), Walker, et al., *Proc. Natl. Acad. Sci. USA,* 89:392 (1992)]; and 3.) methods of library construction and screening by complementation.

For example, genes encoding similar proteins or polypeptides to the Δ9 desaturases described herein could be isolated directly by using all or a portion of the instant nucleic acid fragments as DNA hybridization probes to screen libraries from any desired yeast or fungus using methodology well known to those skilled in the art (wherein those yeast or fungus producing oleic acid [or derivatives thereof] would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach,* K. E. Davis Ed., (1986) pp 33-50, IRL: Herndon, V A; and Rychlik, W., In *Methods in Molecular Biology,* White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA,* 86:5673 (1989); Loh et al., *Science,* 243:217 (1989)).

In other embodiments, any of the Δ9 desaturase nucleic acid fragments described herein (or any homologs identified thereof) may be used for creation of new and improved fatty acid desaturases. As is well known in the art, in vitro mutagenesis and selection, chemical mutagenesis, "gene shuffling" methods or other means can be employed to obtain mutations of naturally occurring desaturase genes. Alternatively, improved fatty acids may be synthesized by domain swapping, wherein a functional domain from any of the Δ9 desaturase nucleic acid fragments described herein are exchanged with a functional domain in an alternate desaturase gene to thereby result in a novel protein.

Methods for Production of Various ω-3 and/or ω-6 Fatty Acids

It is expected that introduction of chimeric genes encoding the Δ9 desaturases described herein (i.e., EgD9 or other mutant enzymes, codon-optimized enzymes or homologs thereof), under the control of the appropriate promoters will result in increased production of oleic acid and palmitoleic acid in the transformed host organism, respectively. As such, the present invention encompasses a method for the direct production of oleic acid and/or palmitoleic acid comprising exposing a fatty acid substrate (i.e., stearic acid and/or palmitic acid, respectively) to the desaturase enzymes described herein (e.g., EgD9), such that the substrate is converted to the desired fatty acid product (i.e., oleic acid and/or palmitoleic acid, respectively).

More specifically, it is an object of the present invention to provide a method for the production of oleic acid in a host cell (e.g., oleaginous yeast), wherein the host cell comprises:
(i) an isolated nucleotide molecule encoding a Δ9 desaturase polypeptide having at least 90% identity when compared to a polypeptide having the amino acid sequence as set forth in SEQ ID NO:2, based on BLASTP algorithms; and,
(ii) a source of stearic acid;
wherein the host cell is grown under conditions such that the Δ9 desaturase is expressed and the stearic acid is converted to oleic acid, and wherein the oleic acid is optionally recovered.

The person of skill in the art will recognize that the broad substrate range of the Δ9 desaturase will also allow for the use of the enzyme for the conversion of palmitic acid to palmitoleic acid. Accordingly the invention provides a method for the production of palmitoleic acid, wherein the host cell comprises:
(i) an isolated nucleotide molecule encoding a Δ9 desaturase polypeptide having at least 90% identity when compared to a polypeptide having the amino acid sequence as set forth in SEQ ID NO:2, based on BLASTP algorithms; and,
(ii) a source of palmitic acid;
wherein the host cell is grown under conditions such that the Δ9 desaturase is expressed and the palmitic acid is converted to palmitoleic acid, and wherein the palmitoleic acid is optionally recovered.

It is contemplated that substrate feeding may be required for either of the methods described above (i.e., production of oleic acid or production of palmitoleic acid).

Alternatively, each Δ9 desaturase gene and its corresponding enzyme product described herein can be used indirectly for the production of various ω-6 and ω-3 PUFAs, including e.g., LA, ALA, GLA, EDA, ETrA, STA, DGLA, ETA, ARA, EPA, DPA and/or DHA (FIG. 1; see PCT Publications No. WO 2004/101757 and No. WO 2006/052870). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ9 desaturases described herein (e.g., EgD9 or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ5 desaturases, Δ15 desaturases, Δ17 desaturases, Δ12 desaturases, $C_{14/16}$ elongases, $C_{16/18}$ elongases, Δ9 elongases, Δ8 desaturases, Δ4 desaturases, $C_{20/22}$ elongases) to result in higher levels of production of longer-chain ω-3/ω-6 fatty acids (e.g., ARA, EPA, DPA and DHA). The particular genes included within a particular expression cassette will depend on the host cell (and its PUFA profile and/or desaturase/elongase profile), the availability of substrate and the desired end product(s).

Thus, in the case of oleaginous yeast, for example, since naturally produced PUFAs in oleaginous yeast are limited to 18:2 fatty acids (i.e., LA), and less commonly, 18:3 fatty acids (i.e., ALA), in some preferred embodiments of the present invention the oleaginous yeast will be genetically engineered to express multiple enzymes, in addition to the Δ9 desaturase described herein. Specifically, in one embodiment this invention concerns an oleaginous yeast comprising:
a) a first recombinant DNA construct comprising an isolated polynucleotide encoding a Δ9 desaturase polypeptide, operably linked to at least one regulatory sequence, wherein said Δ9 desaturase polypeptide has at least 58% identity when compared to a polypeptide having the amino acid sequence as set forth in SEQ ID NO:2, based on BLASTP algorithms and,
b) at least one additional recombinant DNA construct comprising an isolated polynucleotide, operably linked to at least one regulatory sequence, encoding a polypeptide selected from the group consisting of: a Δ6 desaturase, a $C_{18/20}$ elongase, a Δ5 desaturase, a Δ15 desaturase, a Δ17 desaturase, a Δ12 desaturase, a $C_{14/16}$ elongase, a $C_{16/18}$ elongase, a Δ9 elongase, a Δ8 desaturase, a Δ4 desaturase and a $C_{20/22}$ elongase.

Similarly, in one embodiment this invention concerns an oilseed plant comprising:
a) a first recombinant DNA construct comprising an isolated polynucleotide encoding a Δ9 desaturase polypeptide, operably linked to at least one regulatory sequence; and,
b) at least one additional recombinant DNA construct comprising an isolated polynucleotide, operably linked to at least one regulatory sequence, encoding a polypeptide selected from the group consisting of a Δ4 desaturase, a Δ5 desaturase, a Δ6 desaturase, a Δ8 desaturase, a Δ9 desaturase, a Δ9 elongase, a Δ12 desaturase, a Δ15 desaturase, a Δ17 desaturase, a $C_{14/16}$ elongase, a $C_{16/18}$ elongase, a $C_{18/20}$ elongase and a $C_{20/22}$ elongase.

Such additional desaturases are discussed, for example, in U.S. Pat. Nos. 6,075,183, 5,968,809, 6,136,574, 5,972,664, 6,051,754, 6,410,288 and PCT Publication Nos. WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain PUFAs in a plant cell comprising:
a) transforming a cell with the recombinant construct of the invention; and,
b) selecting those transformed cells that make long-chain PUFAs.

In still another aspect, this invention concerns a method for producing at least one PUFA in a soybean cell comprising:
a) transforming a soybean cell with a first recombinant DNA construct comprising:
(i) an isolated polynucleotide encoding a Δ9 desaturase polypeptide, operably linked to at least one regulatory sequence; and,
(ii) at least one additional recombinant DNA construct comprising an isolated polynucleotide, operably linked to at least one regulatory sequence, encoding a polypeptide selected from the group consisting of a Δ4 desaturase, a Δ5 desaturase, a Δ6 desaturase, a Δ8 desaturase, a Δ9 desaturase, a Δ9 elongase, a Δ12 desaturase, a Δ15 desaturase, a Δ17 desaturase, a $C_{14/16}$ elongase, a $C_{16/18}$ elongase, a $C_{18/20}$ elongase and a $C_{20/22}$ elongase;
b) regenerating a soybean plant from the transformed cell of step (a); and, c) selecting those seeds obtained from the plants of step (b) having an altered level of PUFAs when compared to the level in seeds obtained from a nontransformed soybean plant.

Examples of PUFAs having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

Microbial Expression Systems, Cassettes and Vectors

The Δ9 desaturase genes and gene products of the instant sequences described herein (i.e., EgD9 or other mutant enzymes, codon-optimized enzymes or homologs thereof) may be expressed in heterologous host cells. Expression in recombinant hosts may be useful for the production of various PUFA pathway intermediates, or for the modulation of PUFA pathways already existing in the host for the synthesis of new products heretofore not possible using the host.

Expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate host cells via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of the instant Δ9 desaturase ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publications No. WO 2004/101757 and No. WO 2006/052870 for preferred transcriptional initiation regulatory regions for use in Yarrowia lipolytica). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Termination control regions may also be derived from various genes native to the preferred hosts. Optionally, a termination site may be unnecessary; however, it is most preferred if included.

Although not intended to be limiting, termination regions useful in the disclosure herein include: ~100 bp of the 3' region of the Yarrowia lipolytica extracellular protease (XPR; GenBank Accession No. M17741); the acyl-coA oxidase (Aco3: GenBank Accession No. AJ001301 and No. CAΔ04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation and correct folding of the protein in the host organism; 5.) the intrinsic stability of the mRNA and protein of the cloned gene within the host cell; and 6.) the codon usage within the cloned gene, such that its frequency approaches the frequency of preferred codon usage of the host cell. Each of these types of modifications are encompassed in the present invention, as means to further optimize expression of the Δ9 desaturases described herein.

Plant Expression Systems, Cassettes and Vectors

In one embodiment, this invention concerns a recombinant construct comprising any one of the Δ9 desaturase polynucleotides of the invention operably linked to at least one regulatory sequence suitable for expression in a plant. A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the Δ9 desaturase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, the Kunitz trypsin inhibitor 3 promoter, the annexin promoter, the glycinin Gy1 promoter, the beta subunit of beta conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211 (2):267-76 (1998)); (5) a soybean heat shock protein promoter (Schoffl et al., *Mol Gen Genet.* 217(2-3): 246-53 (1989)); and, (6) a maize H3 histone gene promoter (Atanassova et al., *Plant Mol. Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific Δ9 desaturase coding sequence, the promoter is then operably linked in a sense orientation using conventional means well known to those skilled in the art.

Standard recombinant DNA and molecular cloning techniques used herein are well known in the art and are described more fully in Sambrook, J. et al., In Molecular Cloning: A Laboratory Manual; 2nd ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

Transformation of Microbial Host Cells

Once the DNA encoding a polypeptide suitable for expression in an appropriate host cell has been obtained (e.g., a chimeric gene comprising a promoter, ORF and terminator), it is placed in a plasmid vector capable of autonomous replication in the host cell, or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell.

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by various selection techniques, as described in PCT Publications No. WO 2004/101757, No. WO 2005/003310 and No. WO 2006/052870.

Following transformation, substrates suitable for the instant Δ9 desaturases (and, optionally other PUFA enzymes that are co-expressed within the host cell) may be produced by the host either naturally or transgenically, or they may be provided exogenously.

Transformation of Plant Host Cells

Once a recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

Thus, of interest is a method for producing a transformed plant comprising transforming a plant cell with the Δ9 desaturase polynucleotides of the instant invention and regenerating a plant from the transformed plant cell. In alternate preferred embodiments, the present invention provides a variety of plant hosts for transformation with the Δ9 desaturases described herein. Plants so transformed can be monocotyledonous plants or dicotyledonous plants, and preferably they belong to a class of plants identified as oleaginous (e.g., oilseed plants).

Means for overexpression of fatty acid desaturases (e.g., construction of expression cassettes, transformation, selection, etc.) are described in US 2005/0132441. Seeds obtained from such plants are also within the scope of this invention as well as oil obtained from such seeds.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, *F. Microbiol. Sci.* 4:24-28 (1987)). Transformation of soybeans using direct delivery of DNA has been published using PEG fusion (PCT Publication No. WO 92/17598), electroporation (Chowrira, G. M. et al., *Mol. Biotechnol.* 3:17-23 (1995); Christou, P. et al., *Proc. Natl. Acad. Sci.* U.S.A. 84:3962-3966 (1987)), microinjection and particle bombardement (McCabe, D. E. et. al., *Bio/Technology* 6:923 (1988); Christou et al., *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

The recombinant constructs of the invention may be introduced into one plant cell; or, alternatively, each construct may be introduced into separate plant cells. Expression in a plant cell may be accomplished in a transient or stable fashion as is described above.

The desired long-chain PUFAs can be expressed in seed. Also within the scope of this invention are seeds or plant parts obtained from such transformed plants.

Metabolic Engineering of ω-3 and/or ω-6 Fatty Acid Biosynthesis

Knowledge of the sequences of the present Δ9 desaturases will be useful for manipulating ω-3 and/or ω-6 fatty acid biosynthesis in various host cells. This may require metabolic engineering directly within the PUFA biosynthetic pathway or additional coordinated manipulation of various other metabolic pathways. These various other metabolic pathways may include, e.g., those that contribute carbon to the PUFA biosynthetic pathway, those that compete with the ω-3 and/or ω-6 fatty acid biosynthetic pathways for energy or carbon, and/or native PUFA biosynthetic pathway enzymes that interfere with production of a particular PUFA end-product. Methods useful for up-regulating desirable biochemical pathways and down-regulating undesirable biochemical pathways are well known to those skilled in the art (e.g., see PCT Publication No. WO 2004/101757). And, detailed discussion of manipulations within the PUFA biosynthetic pathway as a means to increase ARA, EPA or DHA (and associated techniques thereof) are presented in PCT Publications No. WO 2006/055322, No. WO 2006/052870 and No. WO 2006/052871, respectively, as are desirable manipulations in the TAG biosynthetic pathway and the TAG degradation pathway (and associated techniques thereof).

Preferred Hosts for Recombinant Expression of Δ9 Desaturases

Host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. The genes described in the instant invention have been isolated for expression in an oleaginous yeast (and in particular *Yarrowia lipolytica*); however, it is contemplated that because transcription, translation and the protein biosynthetic apparatus are highly conserved, any plant, algae, bacteria, yeast, euglenoid and/or fungus will be a suitable host for expression of the present nucleic acid fragments.

Preferred hosts are oleaginous organisms, such as oleaginous yeast. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #76982, ATCC #20362, ATCC #8862, ATCC #18944 and/or LGAM S(7)1 (Papanikolaou S., and Aggelis G., *Bioresour. Technol.*, 82(1):43-9 (2002)).

Specific teachings applicable for engineering GLA, ARA, EPA and DHA production in *Y. lipolytica* are provided in U.S. patent application Ser. No. 11/198,975 (PCT Publication No. WO 2006/033723), No. 11/264,784 (PCT Publication No. WO 2006/055322), No. 11/265,761 (PCT Publication No. WO 2006/052870) and No. 11/264,737 (PCT Publication No. WO 2006/052871), respectively. Detailed means for the synthesis and transformation of expression vectors comprising Δ9 desaturases in oleaginous yeast (i.e., *Yarrowia lipolytica*) are provided in PCT Publications No. WO 2004/101757 and No. WO 2006/052870. The preferred method of expressing genes in this yeast is by integration of linear DNA into the genome of the host; and, integration into multiple locations within the genome can be particularly useful when high level expression of genes are desired [e.g., in the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (GenBank Accession No. Z50020) and/or the Lip2 gene locus (GenBank Accession No. AJ012632)].

Preferred selection methods for use in *Yarrowia lipolytica* are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura⁻ mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of Ura⁻ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura– phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3– strain (again identified using 5-FOA selection), when the introduced Ura3 gene is knocked out. Thus, the Ura3 gene (in combination with 5-FOA selection) can be used as a selection marker in multiple rounds of transformation.

Other preferred microbial hosts include oleaginous bacteria, algae, euglenoids and other fungi; and, within this broad group of microbial hosts, of particular interest are microorganisms that synthesize ω-3/ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with the any of the present Δ9 desaturase genes under the control of inducible or regulated promoters could yield a transformant organism capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms are disclosed in U.S. Pat. No. 7,001,772.

In alternate embodiments, it is particularly useful to express the present Δ9 desaturase genes in plant hosts, such as oilseed plants. Examples of oilseed plants include, but are not limited to: soybean (*Glycine* and *Soja* sp.), corn (*Zea mays*), rapeseed (*Brassica* sp.), sunflower (*Helianthus* sp.), primrose, canola, maize, cotton, flax (*Linum* sp.), and safflower (*Carthamus* sp.).

No matter what particular host is selected for expression of the Δ9 desaturases described herein, it is preferable if multiple transformants are screened in order to obtain a strain displaying the desired expression level and pattern. Such screening may be accomplished by Southern analysis of DNA blots (Southern, *J. Mol. Biol.* 98:503 (1975)), Northern analysis of mRNA expression (Kroczek, *J. Chromatogr. Biomed. Appl.*, 618 (1-2):133-145 (1993)), Western and/or Elisa analyses of protein expression, phenotypic analysis or GC analysis of the PUFA products.

Fermentation Processes for Omega Fatty Acid Production

The transformed host cell is grown under conditions that optimize expression of chimeric desaturase and/or elongase genes and produce the greatest and the most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. *Yarrowia lipolytica* are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources are taught in PCT Publication No. WO 2004/101757. Although it is contemplated that the source of carbon utilized in the present invention may encompass a wide variety of carbon-containing sources, preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in *Yarrowia lipolytica*. This approach is described in PCT Publication No. WO 2004/101757, as are various suitable fermentation process designs (i.e., batch, fed-batch and continuous) and considerations during growth.

Isolation and Hydrogenation of Seed Oils

Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed, as described in WO2006/012326.

Soybean oil is liquid at room temperature because it is relatively low in saturated fatty acids when compared with oils such as coconut, palm, palm kernel and cocoa butter. Many processed fats (including spreads, confectionery fats, hard butters, margarines, baking shortenings, etc.) require varying degrees of solidity at room temperature and can only be produced from soybean oil through alteration of its physical properties. This is most commonly achieved through catalytic hydrogenation (see WO2006/012326).

Oils of the Present Invention for Use in Foodstuffs, Health Food Products, Pharmaceuticals and Animal Feeds The market place currently supports a large variety of food and feed products, incorporating ω-3 and/or ω-6 fatty acids (particularly ARA, EPA and DHA). It is contemplated that the yeast oils of the invention comprising long-chain PUFAs will function in food and feed products to impart the health benefits of current formulations. More specifically, oils of the invention containing ω-3 and/or ω-6 fatty acids will be suitable for use in a variety of food and feed products including, but not limited to food analogs, meat products, cereal products, baked foods, snack foods and dairy products (see U.S. Publication No. 2006/0115881, incorporated herein by reference, for details).

Additionally the present oils may be used in formulations to impart health benefit in medical foods including medical nutritionals, dietary supplements and infant formula, as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by:
1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Comparisons of genetic sequences were accomplished using DNASTAR software (DNA Star, Inc.).

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strain ATCC #20362 was purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (Appl. *Microbiol. Biotechnol.*, 48(2):232-235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G., and Nishida I. *Arch Biochem Biophys.*, 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

*Euglena gracilis* Growth Conditions, Lipid Profile and mRNA Isolation

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (Catalog #U126-01, Difco Laboratories, Detroit, Mich.), 2 g of Bacto® tryptone (Catalog #0123-17-3, Difco Laboratories) and 2 g of Bacto® yeast extract (Catalog #0127-17-9, Difco Laboratories) in 970 mL of water. After filter sterilizing, 30 mL of soil-water supernatant (Catalog #15-3790, Carolina Biological Supply Co., Burlington, N.C.) was aseptically added to give the final Eg medium. *Euglena gracilis* cultures were grown at 23° C. with a 16 h light, 8 h dark cycle for 2 weeks with no agitation.

Figure 2:
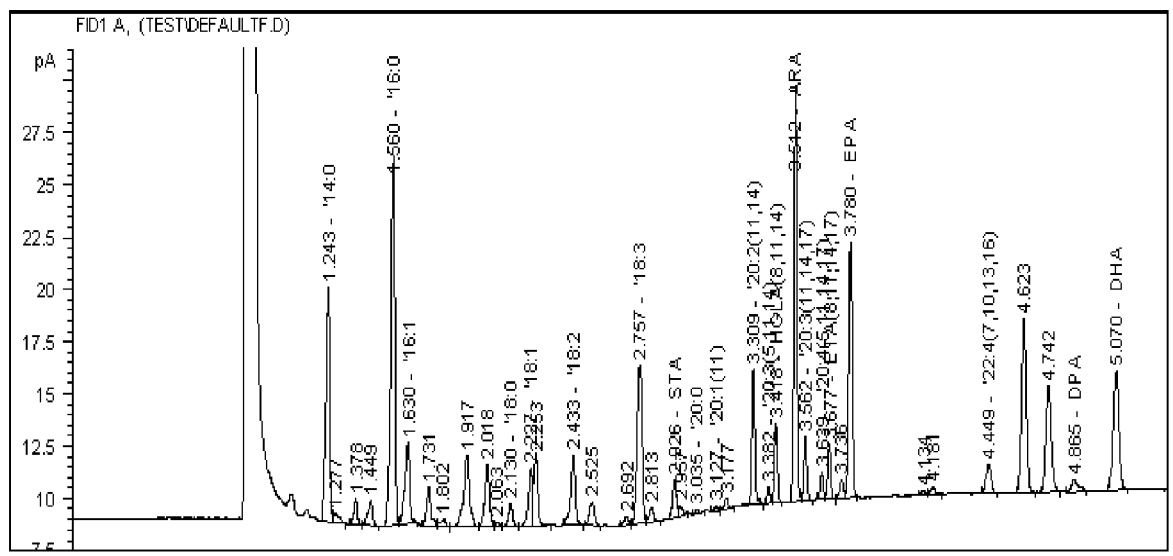
FIG. 2 shows a chromatogram of the lipid profile of an *Euglena gracilis* cell extract as described in Example 1.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 µL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 µl injected from hexane layer) were separated and quantified using a Hewlett-Packard 6890 Gas Chromatograph fitted with an Omegawax 320 fused silica capillary column (Catalog #24152, Supelco Inc., Bellefonte, Pa.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog #U-99-A, Nu-Chek Prep, Inc., Elysian, Minn.) and the resulting chromatogram is shown in FIG. 2.

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 µg of mRNA was obtained.

Example 2

*Euglena gracilis* cDNA Synthesis cDNA was synthesized directly from the *Euglena gracilis* mRNA as follows. Specifically, the mRNA was primered with adapter primer AP (SEQ ID NO:13) from Invitrogen's 3'-RACE kit (Carlsbad, Calif.), in the presence of the SMART™ IV oligonucleotide (SEQ ID NO:14) from the BD-Clontech Creator™ SMART™ cDNA library kit (Mississauga, ON, Canada). The reverse transcription was done with Superscript II reverse transcriptase from the Invitrogen 3'-RACE kit according to the protocol of the Creator™ SMART™ cDNA library kit.

The $1^{st}$ strand cDNA synthesis mixture was used as template for PCR amplification, using AP (SEQ ID NO:13) as the 3' primer and CDSIII 5' primer (SEQ ID NO:15) as the 5' primer (supplied with the BD-Clontech Creator™ SMART™ cDNA library kit). Amplification was carried out with Clontech Advantage cDNA polymerase mix at 94° C. for 30 sec, followed by 20 cycles of 94° C. for 10 sec and 68° C. for 6 min. A final extension at 68° C. for 7 min was performed.

Example 3

Isolation of a Portion of the Coding Region of the *Euglena gracilis* Δ9 Desaturase Gene The present Example describes the identification of a portion of the *Euglena gracilis* gene encoding Δ9 desaturase (designated herein as "EgD9" (SEQ ID NOs:1 and 2)), by use of primers derived from conserved regions of other known desaturase sequences. More specifically, the amplification target in the below experimental work was a Δ5 desaturase; however, since all desaturases share some homology based on their functionality as desaturases, products encoding other desaturases can be amplified by PCR using degenerated oligonucleotides as primers. Thus, a portion of the coding region of the *Euglena gracilis* Δ9 desaturase gene was fortuitously amplified when the targeted gene was Δ5 desaturase.

Degenerate Primer Design

Various considerations were made when evaluating which desaturases might enable design of degenerate primers suitable to isolate the *Euglena gracilis* Δ5 and other Δ8 and Δ9 desaturases. Specifically, as is well known in the art, only Δ5, Δ6 and Δ8 desaturase sequences comprise a conserved 'HPGG' motif at their N-terminus (wherein the 'HPGG' domain is part of the well-known cytochrome B5 domain). In contrast, most Δ9 desaturases possess a 'HPGG' motif of the cytochrome B5 domain at their C-terminus, although plant Δ9 desaturases have no 'HPGG' domain. Both Δ17 and Δ12 desaturases lack the cytochrome B5 domain. It was assumed that a Δ9 elongase/Δ8 desaturase pathway operated in *Euglena gracilis*. Thus, among the desaturases sharing the N-terminal conserved 'HPGG' motif (i.e., Δ5, Δ6 and Δ8 desaturases), only Δ5 and Δ8 desaturases were expected within the organism. It was unknown whether the *Euglena gracilis* Δ9 desaturase would contain a C-terminal 'HPGG' domain. The Applicants selected those Δ5 desaturase sequences that possessed lower homology to "traditional" Δ5 desaturase genes and that also shared high homology to one another.

Based on the above, the four Δ5 desaturases and two Δ8 desaturases shown below in Table 3 were aligned, using the method of Clustal W (slow, accurate, Gonnet option; Thompson et al., *Nucleic Acids Res.*, 22:4673-4680 (1994)) of the MegAlign™ program of DNASTAR software (Madison, Wis.).

TABLE 3

Δ5 And Δ8 Desaturases Aligned To Identify Regions Of Conserved Amino Acids

| Desaturase | Organism | Abbreviation Within FIG. 3 | Reference | SEQ ID NO: |
|---|---|---|---|---|
| Δ5 | *Phaeodactylum tricornutum* | Pt | GenBank Accession No. AAL92562 | 16 |
| Δ5 | *Phytophthora megasperma* | PM | GenBank Accession No. CAD53323 | 17 |
| Δ5 | *Phythium irregulare* | Pi | GenBank Accession No. AAL13311 | 18 |
| Δ5 | *Dictyostelium discoideum* | Dc | GenBank Accession No. XP_640331 | 19 |
| Δ8 | *Euglena gracilis* | Eu-D8 DSWT | PCT Publications No. WO 2006/012325 and No. WO 2006/012326 | 20 |
| Δ8 | *Pavlova lutheri* | PvD8WT | Example 8 (infra) | 22 |

FIG. 3 shows a portion of the resulting alignment, containing several stretches of conserved amino acid sequence among the 6 different organisms. Based on this alignment, two sets of degenerate oligonucleotides were designed to amplify a portion of the coding region of the Δ5 desaturase gene from *Euglena gracilis*, corresponding to the regions of FIG. 3 that are labeled as "Conserved Region 1" and "Conserved Region 2". Specifically, the conserved amino acid sequence GHH(I/V)YTN (SEQ ID NO:23) was designed to correspond to Conserved Region 1, while the conserved amino acid sequence NFQ(V/A)(S/N)HV (SEQ ID NO:24) was designed to correspond to Conserved Region 2. In order to reduce the degeneracy of the oligonucleotides, 4 sets of oligonucleotides (i.e., 5-1A, 5-1B, 5-1C and 5-1D) were designed to encode Conserved Region 1; and 4 sets of oligonucleotides (i.e., 5-4AR, 5-4BR, 5-4CR and 5-4DR) were designed to encode Conserved Region 2.

TABLE 4

Degenerate Oligonucleotides Used To Amplify The Δ5 Desaturase Gene From *Euglena gracilis*

| Oligonucleotide Name | Sequence | SEQ ID NO |
|---|---|---|
| 5-1A | GGHCAYCAYRTBTAYACAAA | SEQ ID NO: 25 |
| 5-1B | GGHCAYCAYRTBTAYACCAA | SEQ ID NO: 26 |
| 5-1C | GGHCAYCAYRTBTAYACGAA | SEQ ID NO: 27 |
| 5-1D | GGHCAYCAYRTBTAYACTAA | SEQ ID NO: 28 |
| 5-4AR | ACRTGRYTNACYTGRAAGTT | SEQ ID NO: 29 |
| 5-4BR | ACRTGRYTNACYTGRAAATT | SEQ ID NO: 30 |
| 5-4CR | ACRTGNGANACYTGRAAGTT | SEQ ID NO: 31 |
| 5-4DR | ACRTGNGANACYTGRAAATT | SEQ ID NO: 32 |

[Note:
The nucleic acid degeneracy code used for SEQ ID NOs: 25 to 32 was as follows: R = A/G; Y = C/T; W = A/T; B = G/T/C; V = G/A/C; and H = A/C/T.]

Based on the full-length sequences of the Δ5 sequences of Table 3, it was hypothesized that the *Euglena gracilis* Δ5 gene fragment amplified as described above would be about 600 bp in length (lacking about 210 amino acids at its N-terminal and 70 amino acids at its C-terminal).

A total of sixteen different PCR amplifications were conducted, as all combinations of the primers were tested (i.e., primer 5-1A was used with each of 5-4AR, 5-4BR, 5-4CR and 5-4DR, individually; similarly, primer 5-1B was used with each of 5-4AR, 5-4BR, 5-4CR and 5-4DR; etc.). The PCR amplifications were carried out in a 50 μl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer, 10 ng cDNA of *E. gracis* and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.). One fragment of the approximate expected size was then further purified following gel electrophoresis in 1% (w/v) agarose and then cloned into the pGEM-T-easy vector (Promega, Madison, Wis.). The ligated DNA was used to transform cells of *E. coli* DH10B and transformants were selected on LB (1% bacto-tryptone, 0.5% bacto-yeast extract and 1% NaCl) agar containing ampicillin (100 μg/mL). Analysis of the plasmid DNA from a group of 10 transformants confirmed the presence of the insert with the expected size (plasmids were designated as "pT-F4-1", "pT-F4-2", "pT-F4-3", etc. to "pT-F4-10").

Sequence analyses showed that pT-F4-1 contained a 572 bp fragment (SEQ ID NO:3). Translation of SEQ ID NO:3 yielded a protein fragment of 186 amino acids (SEQ ID NO:4), which included the first 6 amino acids of Conserved Region 1 (SEQ ID NO:23). Surprisingly, however, SEQ ID NO:4 did not contain Conserved Region 2 (SEQ ID NO:24) at the C-terminal end; instead, the translated reverse complement strand of the pT-F4-1 fragment contained a second region comprising the first 6 amino acids of Conserved Region 1 (see boxed sequences in FIG. 4). This fragment was amplified by using 5-1B oligonucleotides (SEQ ID NO:26) for both forward and reverse primers.

Identity of the *Euglena* sequence set forth as SEQ ID NO:3 was determined by conducting BLAST (Basic Local Alignment Search Tool; Altschul, S. F., et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The sequence was compared for similarity to all publicly available protein sequences contained in the "nr" database, using the BLASTX algorithm (Gish, W. and States, D. J. *Nature Genetics,* 3:266-272 (1993)) provided by the NCBI. The results of the BLASTX comparison summarizing the sequence to which SEQ ID NO:3 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Thus, the translated amino acid sequence of SEQ ID NO:3 (i.e., SEQ ID NO:4) had 49% identity and 66% similarity with the amino acid sequence of the putative Δ9 desaturase of *Arabidopsis thaliana* (GenBank Accession AAN41357; SEQ ID NO:33), with an Expectation value of 4E-47; additionally, the translated amino acid sequence of SEQ ID NO:3 had 54% identity and 52% similarity with the Δ9 fatty acid desaturase of *Picea glauca* (GenBank Accession No. AAM12238; SEQ ID NO:34), with an Expectation value of 2E-46.

Example 4

Isolation of the 5'Coding Region of the *Euglena gracilis* Δ9 Desaturase Gene

To isolate the N-terminal portion of the putative Δ9 desaturase identified in Example 3, a modified 5' RACE technique based on RACE protocols from two different companies (i.e., Invitrogen and BD-Clontech) was utilized. Briefly, the double-stranded cDNA of *Euglena gracilis* (Example 2) was used as the template in a 5' RACE experiment, comprising two separate rounds of PCR amplification. In the first round of PCR amplification, the oligonucleotide primers consisted of a gene specific oligonucleotide (i.e., Eg9-5'1; SEQ ID NO:35) and the generic oligonucleotide CDSIII 5' primer (SEQ ID NO:15) from the BD-Clontech Creator™ SMART™ cDNA library kit. The PCR amplifications were carried out in a 50 μl total volume, comprising: 25 μl of LA Taq™ pre-mix (TaKaRa Bio Inc., Otsu, Shiga, 520-2193, Japan), 10 pmole of each primer and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min. The second round of PCR amplification used 1 μl of the product from the first round PCR reaction as template. Primers consisted of a gene specific oligonucleotide (i.e., Eg9-5'2; SEQ ID NO:36) and the generic oligonucleotide DNR CDS 5' (SEQ ID NO:37), supplied with the Creator™ SMART™ cDNA library kit. Amplification was conducted as described above.

The products of the second round PCR reaction were electrophoresed in 1% (w/v) agarose. Products between 400 bp and 800 bp were then purified from the gel and cloned into the pGEM-T-easy vector (Promega, Madison, Wis.). The ligated DNA was used to transform *E. coli* DH10β and transformants were selected on LB agar containing ampicillin (100 μg/mL). Analysis of the plasmid DNA from one transformant comprising the 5' region of the putative Δ9 desaturase gene confirmed the presence of the expected plasmid, designated pT-EgD9-5'C2. Sequence analyses showed that pT-EgD5-5'C2 contained a fragment of 653 bp (SEQ ID NO:5), which over-lapped with 387 bp from the 5' end of the 572 bp fragment of pT-F4-1 (Example 3, SEQ ID NO:3) and additionally provided 266 bp of 5' upstream sequence (SEQ ID NO:6). This 266 bp upstream sequence included 150 bp (SEQ ID NO:7) encoding the N-terminal portion of the putative Δ9 desaturase gene (including the translation initiation codon) and an additional 116 bp (SEQ ID NO:8) of untranslated 5' sequence. The sequence of pT-EgD5-5'C2 also corrected the sequence corresponding to Conserved Region 1, resulting from use of a degenerate oligonucleotide for initial PCR amplification of the 572 bp fragment in pT-F4-1 (Example 3).

Example 5

Isolation of the 3'Coding Region of the *Euglena gracilis* Δ9 Desaturase Gene

To isolate the C-terminal portion of the putative Δ9 desaturase identified in Example 3, a 3' RACE technique was utilized. The methodology was as described above in Example 4; however, the primers used in both the first and second rounds of PCR amplification were as shown below in Table 5.

TABLE 5

| Oligonucleotide Primers Used For 3' RACE | | |
|---|---|---|
| PCR Amplification | Gene Specific Oligonucleotide | Generic Oligonucleotide |
| 1st Round | Eg9-3'1 (SEQ ID NO: 38) | AUAP (SEQ ID NO: 39) |
| 2nd Round | Eg9-3'2 (SEQ ID NO: 40) | AUAP (SEQ ID NO: 39) |

* Primer AUAP was supplied in Invitrogen's 3'-RACE kit (Carlsbad, CA).

Following isolation and purification of products (i.e., 400-800 bp), the fragments were cloned into the pGEM-T-easy vector (Promega) and transformed into *E. coli* DH10β, as in Example 4. Analysis of the plasmid DNA from one transformant comprising the 3' region of the Δ9 desaturase gene confirmed the presence of the expected plasmid, designated pT-EgD9-3'. Sequence analyses showed that pT-EgD9-3' contained a fragment of 660 bp (SEQ ID NO:9), which over-lapped with 117 bp from the 3' end of the 572 bp fragment of pT-F4-1 (Example 3, SEQ ID NO:3) and provided 543 bp of additional 3' downstream sequence (SEQ ID NO:10). This 543 bp downstream sequence included 300 bp (SEQ ID NO:11) encoding the C-terminal coding region of the putative Δ9 desaturase gene (including the translation stop codon), and an additional 243 bp of untranslated 3' sequence (SEQ ID NO:12). The sequence of pT-EgD9-3' also corrected the 3' end of the 572 bp fragment in pT-F4-1 (Example 3), resulting from the use of degenerate oligonucleotide 5-1B for initial PCR amplification.

After one round of 5' RACE (Example 4) and one round of 3' RACE (supra), the DNA sequence of the entire putative *Euglena gracilis* Δ9 coding region was determined. Specifically, assembly of the 5' fragment from pT-EgD9-5'C2 (SEQ ID NO:5), the original partial cDNA fragment (SEQ ID NO:3) and the 3' fragment from pT-EgD9-3' (SEQ ID NO:9) resulted in the complete sequence of the Δ9 desaturase from *Euglena gracilis*, plus 116 bp of 5' untranslated region and 243 bp of 3' untranslated region (SEQ ID NO:63; 1382 bp). The coding region (designated herein as "EgD9") was 1023 bp in length (SEQ ID NO:1) and encoded a polypeptide of 340 amino acids (SEQ ID NO:2).

The sequence was compared for similarity to all publicly available protein sequences contained in the "nr" database, using the BLASTP algorithm (Altschul, S., et al., *Nucleic Acids Res.*, 25:3389-3402 (1997); Schaffer, A., et al., *Nucleic Acids Res.*, 29:2994-3005 (2001)) provided by the NCBI. The results of BLASTP searches using the full length EgD9 protein (SEQ ID NO:2) as the query sequence showed that it shared 55% identity and 71% similarity with the amino acid sequence of the putative Δ9 desaturase of *Arabidopsis thaliana* (GenBank Accession AAN41357; SEQ ID NO:33), with an Expectation value of 4E-94. Additionally, SEQ ID NO:2 shared 58% identity and 70% similarity with the Δ9 fatty acid desaturase of *Picea glauca* (GenBank Accession No. AAM12238; SEQ ID NO:34), with an Expectation value of 2E-92.

Interestingly, evaluation of the EgD9 C-terminus revealed no conserved 'HPGG' motif of the cytochrome B5 domain (see Example 3), in a manner similar to that of plant Δ9 desaturases.

Example 6

Generation of Construct pZP2NEg9, Comprising the *Euglena gracilis* Δ9 Desaturase (EgD9)

The present Example describes the generation of pZP2NEg9 (FIG. 5C; SEQ ID NO:47), comprising a chimeric YAT1::EgD9::Pex20-3' terminator gene. This construct was designed to integrate the chimeric gene into the genome of *Yarrowia lipolytica* and thereby enable the function of the *Euglena gracilis* Δ9 desaturase to be studied (infra, Example 7).

Based on the full length cDNA of EgD9 (SEQ ID NO:1), oligonucleotides YL837 and YL838 (SEQ ID NOs:41 and 42, respectively) were used as primers to amplify the first portion of EgD9. Primer YL837 contained a NcoI site and primer YL838 contained a SphI site. Then, primers YL839 and YL840 (SEQ ID NOs:43 and 44, respectively) were used as primers to amplify the second portion of EgD9. Primer YL839 contained a SphI site, while primer YL840 contained a NotI site. The PCR reactions, using primer pairs YL837/YL838 or YL839/YL840, with *Euglena gracilis* cDNA (Example 2) as template, were individually carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min. The individual PCR products were purified using a Qiagen PCR purification kit. The PCR product from the reaction amplified with primers YL837/YL838 was digested with NcoI and SphI, while the PCR product from the reaction amplified with primers YL839/YL840 was digested with SphI and NotI.

The NcoI/SphI and the SphI/NotI digested DNA fragments were purified following gel electrophoresis in 1% (w/v) agarose, and then directionally ligated with a ClaI/NcoI fragment containing the *Yarrowia lipolytica* YAT1 promoter from pNT-GUS1-CN (FIG. 5A; SEQ ID NO:45) and ClaI/NotI digested pZP2L7+Ura (FIG. 5B; SEQ ID NO:46). As shown in FIG. 5B, plasmid pZP2L7+Ura is a *Y. lipolytica* integration plasmid comprising a chimeric TEF::synthetic Δ17 desaturase (codon-optimized for *Y. lipolytica* and derived from *Saproglenia diclina* [U.S. Pat. No. 7,125,672])::Pex20-3' gene and a Ura3 gene, for use as a selectable marker.

The product of the ligation described above was pZP2NEg9 (FIG. 5C; SEQ ID NO:47), which thereby contained the following components:

TABLE 6

Components Of Plasmid pZP2NEg9 (SEQ ID NO: 47)

| RE Sites And Nucleotides Within SEQ ID NO: 47 | Description Of Fragment And Chimeric Gene Components |
|---|---|
| ClaI/BsiWI (7356-1344) | YAT1::EgD9::Pex20, comprising: YAT Pro.: *Yarrowia lipolytica* YAT1 promoter (Patent |

TABLE 6-continued

Components Of Plasmid pZP2NEg9 (SEQ ID NO: 47)

| RE Sites And Nucleotides Within SEQ ID NO: 47 | Description Of Fragment And Chimeric Gene Components |
|---|---|
| | Publication US 2006/0094102-A1) (identified as "NT Pro" in FIG. 5C) |
| | EgD9: *Euglena gracilis* Δ9 desaturase (SEQ ID NO: 1 described herein) |
| | Pex20: Pex20 terminator sequence of *Yarrowia* Pex20 gene (GenBank Accession No. AF054613) |
| PmeI with EcoRV/PacI (7007-5517) | *Yarrowia* Ura 3 gene (GenBank Accession No. AJ306421) |
| 3142-4002 | Ampicillin-resistance gene (AmpR) for selection in *E. coli* |
| AscI/BsiWI (2154-1344) | 5' region of *Yarrowia* Aco2 gene (GenBank Accession No. AJ001300) |
| PacI/SphI (5517/4862) | 3' region of *Yarrowia* Aco2 gene (GenBank Accession No. AJ001300) |

Example 7

Functional Analysis of the *Euglena gracilis* Δ9 Desaturase (EgD9) in *Yarrowia lipolytica* Y2224 Strain The present Example describes functional analysis of EgD9 in *Yarrowia lipolytica* strain Y2224. Thus, following creation of strain Y2224 (a FOA resistant mutant from an autonomous mutation of the Ura3 gene of wildtype *Yarrowia* strain ATCC #20362), plasmid pZP2NEg9 (Example 6; SEQ ID NO:47) was transformed into the cells and lipid profiles within non-transformant and transformant (comprising EgD9) organisms of *Yarrowia lipolytica* strain Y2224 were compared.

Generation of Strain Y2224

Strain Y2224 was isolated in the following manner: *Yarrowia lipolytica* ATCC #20362 cells from a YPD agar plate (1% yeast extract, 2% bactopeptone, 2% glucose, 2% agar) were streaked onto a minimal media plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto minimal media plates containing 200 mg/mL 5-FOA and minimal media plates lacking uracil and uridine to confirm uracil Ura3 auxotrophy.

Functional Analysis of EgD9

Plasmid pZP2NEg9 (comprising the chimeric YAT1::EgD9::Pex20-3' terminator gene (Example 6)) was digested with XmnI and AscI, and then transformed into strain Y2224 as described in the General Methods. The transformants were selected on MM plates. After 2 days grown at 30° C., a total of 24 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification and subsequently analyzed with a Hewlett-Packard 6890 GC.

GC analyses showed that the C16:0 and C18:0 contents were significantly reduced, and the C16:1, C18:1 plus C18:2 contents were significantly increased in 2 of the 24 transformants (i.e., clones #10 and #23).

To confirm the function of EgD9 in these two transformants, triplicates of clones #10 and #23 and the Y2224 host strains were cultured as described above. The cells were collected by centrifugation, lipids were extracted, and fatty acid methyl esters were prepared and analyzed (supra). Fatty acids are identified as 16:0 (palmitate), 16:1 (palmitoleic acid), 18:0, 18:1 (oleic acid) and 18:2 (LA); and the composition of each is presented as a % of the total fatty acids (Table 7).

TABLE 7

Comparison Of Fatty Acid Composition In *Yarrowia* Strain Y2224 Transformed with pZP2NEg9

| Strain | Total Fatty Acids | | | | |
|---|---|---|---|---|---|
| | 16:0 | 16:1 | 18:0 | 18:1 | 18:2 |
| Control-1 | 16.2 | 7.2 | 5.7 | 51.5 | 17.1 |
| Control-2 | 16.0 | 7.3 | 5.7 | 52.7 | 15.9 |
| Control-3 | 16.0 | 7.3 | 5.7 | 52.2 | 16.3 |
| Average | 16.0 | 7.3 | 5.7 | 52.1 | 16.5 |
| pZP2NEg9 #10-1 | 14.1 | 7.6 | 5.3 | 50.0 | 20.1 |
| pZP2NEg9 #10-2 | 14.1 | 7.6 | 5.5 | 49.5 | 20.4 |
| pZP2NEg9 #10-3 | 14.2 | 7.5 | 5.6 | 49.7 | 20.0 |
| Average | 14.1 | 7.6 | 5.4 | 49.7 | 20.2 |
| pZP2NEg9 #23-1 | 12.1 | 9.0 | 3.2 | 60.6 | 12.9 |
| PZP2NEg9 #23-2 | 12.0 | 9.0 | 3.3 | 60.1 | 13.3 |
| pZP2NEg9 #23-3 | 12.7 | 8.7 | 3.3 | 60.0 | 12.9 |
| Average | 12.3 | 8.9 | 3.2 | 60.2 | 13.0 |

GC analyses (Table 7) showed that the content of C16:0 was reduced 11.7% and 23.5%, and the C18:0 was reduced 5.1% and 43.54% in transformants #10 and #23, compared with the host strain Y2224, respectively. The content of C16:1 was increased 4.4% and 22.8%, and the C18:1 plus C18:2 was increased 1.9% and 6.8% in transformants #10 and #23, compared with the host strain Y2224, respectively. These data demonstrated that EgD9 functioned as a Δ9 desaturase in *Yarrowia lipolytica*.

Example 8

Isolation of a *Pavlova lutheri* (CCMP459) Δ8 Desaturase

The present Example, disclosed in U.S. Patent Application No. 60/795,810, describes the isolation of the *Pavlova lutheri* (CCMP459) Δ8 desaturase utilized in Example 3 and in FIG. 3. The isolation required: synthesis of *Pavlova lutheri* (CCMP459) cDNA, library construction and sequencing; identification of Δ8 desaturase homologs; and, cloning of a full-length Δ8 desaturase from genomic DNA.

*Pavlova lutheri* (CCMP459) cDNA Synthesis, Library Construction and Sequencing

A cDNA library of *Pavlova lutheri* (CCMP459) was synthesized as described in PCT Publication No. WO 2004/071467 (published Aug. 26, 2004). Briefly, frozen pellets of *Pavlova lutheri* CCMP459 were obtained from Provasoli-Guillard National Center for Culture of Marine Phytoplankton (CCMP, West Boothbay Harbor, Me.). These pellets were crushed in liquid nitrogen and total RNA was extracted from *Pavlova lutheri* CCMP459 by using the Qiagen RNeasy® Maxi Kit (Qiagen, Valencia, Calif.), per the manufacturer's instructions. From this total RNA, mRNA was isolated using oligo dT cellulose resin, which was then used for the construction of a cDNA library using the pSport1 vector (Invitrogen, Carlsbad, Calif.). The cDNA thus produced was directionally cloned (5' SalI/3' NotI) into pSport1 vector. The *Pavlova lutheri* CCMP459 library contained approximately $6.1 \times 10^5$ clones per mL, each with an average insert size of approximately 1200 bp. The *Pavlova lutheri* library was named "eps1c".

For sequencing, clones first were recovered from archived glycerol cultures grown/frozen in 384-well freezing media plates, and inoculated with an automatic QPix® colony picker (Genetix) in 96-well deep-well plates containing LB+100 mg/mL ampicillin. After growing 20 hrs at 37° C., cells were pelleted by centrifugation and stored at −20° C. Plasmids then were isolated on an Eppendorf 5Prime robot, using a modified 96-well format alkaline lysis miniprep method (Eppendorf PerfectPrep®). Briefly, a filter and vacuum manifold was used to facilitate removal of cellular debris after acetate precipitation. Plasmid DNA was then bound on a second filter plate directly from the filtrate, washed, dried and eluted.

Plasmids were end-sequenced in 384-well plates, using vector-primed T7 primer (SEQ ID NO:48) and the ABI Big-Dye version 3 Prism sequencing kit. For the sequencing reaction, 100-200 ng of template and 6.4 pmoL of primer were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3700 automated sequencers.

Identification of Δ8 Desaturase Enzyme Homologs From *Pavlova lutheri* cDNA Library eps1c cDNA clones encoding *Pavlova lutheri* Δ8 desaturase homologs (hereby designated as Δ8 desaturases) were identified by conducting BLAST searches for similarity to sequences contained in the BLAST "nr" database (as described in Example 3). The P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequence from clone eps1c.pk002.f22 revealed similarity of the protein encoded by the cDNA to the Δ6 desaturase from *Rhizopus stolonifer* (SEQ ID NO:49) (NCBI Accession No. AAX22052 (GI 60499699), locus AAX22052, CDS AY795076; Lu et al., unpublished). The sequence of a portion of the cDNA insert from clone eps1c.pk002.f22 is shown in SEQ ID NO:50 (5' end of cDNA insert). Subsequently, the full insert sequence (eps1c.pk002.f22:fis) was obtained and is shown in SEQ ID NO:51. Sequence for the deduced amino acid sequence (from nucleotide 1 of SEQ ID NO:51 to the first stop codon at nucleotide 864 of SEQ ID NO:51) is shown in SEQ ID NO:52. Full insert sequencing was carried out using a modified transposition protocol. Clones identified for full insert sequencing were recovered from archived glycerol stocks as single colonies, and plasmid DNA was isolated via alkaline lysis. Plasmid templates were transposed via the Template Generation System (TGS II) transposition kit (Finnzymes Oy, Espoo, Finland), following the manufacturer's protocol. The transposed DNA was transformed into EH10B electro-competent cells (Edge BioSystems, Gaithersburg, Md.) via electroporation. Multiple transformants were randomly selected from each transposition reaction, plasmid DNA was prepared, and templates were sequenced as above (ABI BigDye v3.1) outward from the transposition event site, utilizing unique primers SeqE (SEQ ID NO:53) and SeqW (SEQ ID NO:54).

Sequence data was collected (ABI Prism Collections software) and assembled using the Phrap sequence assembly program (P. Green, University of Washington, Seattle).

Assemblies were viewed by the Consed sequence editor (D. Gordon, University of Washington, Seattle) for final editing.

The amino acid sequence set forth in SEQ ID NO:52 was evaluated by BLASTP, yielding a pLog value of 19.52 (E value of 3e-20) versus the Δ6 desaturase from *Mortierella alpina* (NCBI Accession No. BAC82361 (GI 34221934), locus BAC82361, CDS AB070557; Sakuradani and Shimizu, *Biosci. Biotechnol. Biochem.*, 67:704-711 (2003)). Based on the results from the BLASTP comparison to the *Mortierella alpina* and other fatty acid desaturases, the *Pavlova lutheri* Δ8 desaturase was not full length and was lacking sequence at the 5' end.

Cloning a Full-Length Δ8 Desaturase from *Pavlova lutheri* Genomic DNA

Genomic DNA was isolated from *Pavlova lutheri* (CCMP459) using the Qiagen DNeasy® Plant Maxi Prep Kit according to the manufacturer's protocol. Using 1 maxi column per 1 gm of frozen cell pellet, a total of 122 µg of genomic DNA was isolated from 4 gm of *Pavlova lutheri* culture. The final concentration of genomic DNA was 22.8 ng/µL. GenomeWalker libraries were synthesized using the Universal GenomeWalker™ kit (BD Biosciences Clonetech, Palo Alto, Calif.) following the manufacturer's protocol (Prot #PT3042-1, version PRO3300). Briefly, four restriction digests were set up as per the protocol using 300 ng of genomic DNA per reaction. After phenol clean up, pellets were dissolved in 4 µL of water and adapters were ligated as per the protocol.

For the primary PCR, the Advantage®-GC Genomic PCR kit (BD Biosciences Clonetech) was used following the manufacturer's protocol (Prot #PT3090-1, version #PR1X433). For each restriction digest, 1 µL of library was combined with 22.8 µL of PCR grade water, 10 µL of 5×GC Genomic PCR Reaction Buffer, 2.2 µL of 25 mM $Mg(CH_3CO_2)_2$, 10 µL of GC-Melt (5 M), 1 µL of 50×dNTP mix (10 mM each), 1 µL of Advantage-GC Genomic Pol. Mix (50×), 1 µL of Universal GenomeWalker™ primer AP1 (10 µM, SEQ ID NO:55) and 1 µL of GSP PvDES (10 µM, SEQ ID NO:56). After denaturation at 95° C., the following reaction conditions were repeated 35 times: 94° C. for 30 sec, 68° C. for 6 min. After these reaction conditions, an additional extension at 68° C. was carried out for 6 min followed by cooling to 15° C. until removed.

The primary PCR reaction for each library was analyzed by agarose gel electrophoresis and DNA bands with molecular weights around 6 kB, 3.5 kB, 2.5 kB and 1.2 kB were observed. DNA bands for each library were purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol and inserts were sequenced using the T7 (SEQ ID NO:48) and M13-28Rev (SEQ ID NO:57) primers as described above. Additional sequence was then obtained using a gene-specific sequencing primer PavDES seq (SEQ ID NO:58) that was derived from the newly acquired sequence data. The full 5' end sequence obtained by genome walking is shown in SEQ ID NO:59. The sequence of the overlapping regions of the genomic sequence (SEQ ID NO:59) and the fully sequenced EST eps1c.pk002.f22:fis (SEQ ID NO:51) were aligned using Sequencher™ (Version 4.2, Gene Codes Corporation, Ann Arbor, Mich.) using the Large Gap assembly algorithm. Interestingly, the comparison showed that the EST that was originally sequenced (SEQ ID NO:51) was lacking 459 bp when compared to the genomic sequence (SEQ ID NO:59). This missing sequence in the EST appeared to be a deletion rather than an intron as no clear intron splice sites were identified in the genomic DNA at the 5' end of the gene. The genomic sequence for the 5' end (SEQ ID NO:59) was combined with the 3' end of the EST sequence (SEQ ID NO:51) to yield SEQ ID NO:60. Using EditSeq™ 6.1 sequence analysis software (DNASTAR Inc., Madison, Wis.), an ORF was identified (SEQ ID NO:21). The amino acid sequence coded for by SEQ ID NO:21 is shown in SEQ ID NO:22.

The amino acid sequence set forth in SEQ ID NO:22 was evaluated by BLASTP, yielding a pLog value of 35.10 (E value of 8e-36) versus the Δ6 desaturase from *Rhizopus stolonifer* (SEQ ID NO:61) (NCBI Accession No. ABB96724 (GI 83027409), locus ABB96724, CDS DQ291156; Zhang et al., unpublished). Furthermore, the *Pavlova lutheri* Δ8 desaturase is 78.0% identical to the *Pavlova salina* Δ8 desaturase sequence (SEQ ID NO:62) disclosed in PCT Publication No. WO 2005/103253 (published Apr. 22, 2005) using the Jotun Hein method. Sequence percent identity calculations performed by the Jotun Hein method (Hein, J. J., *Meth. Enz.*, 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). The *Pavlova lutheri* Δ8 desaturase is 76.4% identical to the *Pavlova salina* Δ8 desaturase sequence using the Clustal V method. Sequence percent identity calculations performed by the Clustal V method (Higgins, D. G. and Sharp, P. M., *Comput. Appl. Biosci.*, 5:151-153 (1989); Higgins et al., *Comput. Appl. Biosci.*, 8:189-191 (1992)) were done using the MegAlign™ v6.1 program of the LASERGENE bioinformatics computing suite (supra) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the fragment of SEQ ID NO:21 encodes an entire *Pavlova lutheri* Δ8 desaturase.

FIGS. 6A and 6B show a Clustal V alignment (with default parameters) of SEQ ID NO:22 (the amino acid sequence of the *Pavlova lutheri* Δ8 desaturase), SEQ ID NO:62 (the amino acid sequence of *Pavlova salina* Δ8 desaturase sequence, supra), SEQ ID NO:20 (the amino acid sequence of *Euglena gracilis* Δ8 desaturase sequence disclosed as SEQ ID NO:2 in PCT Publication No. WO 2006/012325; published Feb. 2, 2006), SEQ ID NO:61 (the amino acid sequence for the *Rhizopus stolonifer* Δ6 fatty acid desaturase (NCBI Accession No. ABB96724, supra) and SEQ ID NO:49 (the amino acid sequence for the *Rhizopus stolonifer* Δ6 fatty acid desaturase (NCBI Accession No. AAX22052, supra). The results of the Clustal V alignment show that SEQ ID NO:22 is 76.4%, 22.6%, 22.2% and 22.2% identical to SEQ ID NO:62, SEQ ID NO:20, SEQ ID NO:61 and SEQ ID NO:49, respectively.

What is claimed is:

1. An isolated nucleic acid molecule comprising:
   a.) an isolated nucleotide sequence encoding a Δ9 desaturase enzyme as set forth in SEQ ID NO:2;
   b.) an isolated nucleotide sequence encoding a Δ9 desaturase enzyme that hybridizes with (a) under the following hybridization conditions: 0.1×SSC, 0.1% SDS, 65° C. and washed with 2×SSC, 0.1% SDS followed by 0.1× SSC, 0.1% SDS; or
   c.) an isolated nucleotide sequence that is completely complementary to (a) or (b).

2. The isolated nucleic acid molecule of claim 1 as set forth in SEQ ID NO:1.

3. An isolated nucleic acid molecule comprising a first nucleotide sequence encoding a Δ9 desaturase enzyme of at least 340 amino acids that has at least 90% identity based on BLASTP algorithms when compared to a polypeptide having the sequence as set forth in SEQ ID NO:2;
   or a second nucleotide sequence comprising the complement of the first nucleotide sequence.

4. A chimeric gene comprising the isolated nucleic acid molecule of claim 1 operably linked to at least one regulatory sequence.

5. A transformed host cell comprising the isolated nucleic acid molecule of claim 1.

6. The transformed host cell of claim 5, selected from the group consisting of plants, algae, bacteria, euglenoids, fungi and yeast.

7. The transformed host cell of claim 6, wherein the yeast is an oleaginous yeast.

8. The transformed host cell of claim 7, wherein the oleaginous yeast cell is selected from the group consisting of: *Yarrowia, Candida, Rhodotorula, Rhodosporidium, Cryptococcus, Trichosporon* and *Lipomyces*.

9. A transformed *Yarrowia* sp, comprising the isolated nucleic acid molecule of claim 1.

10. The transformed *Yarrowia* sp, of claim 9 selected from the group consisting of *Yarrowia lipolytica* ATCC #20362, *Yarrowia lipolytica* ATCC #8862, *Yarrowia lipolytica* ATCC #18944, *Yarrowia lipolytica* ATCC #76982 and *Yarrowia lipolytica* LGAM S(7)1.

11. A method for the production of oleic acid comprising:
   a.) providing a host cell comprising:
      i) an isolated nucleotide molecule encoding a Δ9 desaturase polypeptide according to claim 1; and,
      (ii) a source of stearic acid; and
   b.) growing the host cell of step (a) under conditions wherein the nucleic acid molecule encoding the Δ9 desaturase polypeptide is expressed and the stearic acid is converted to oleic acid.

12. A method for the production of palmitoleic acid comprising:
   a.) providing a host cell comprising:
      i) an isolated nucleotide molecule encoding a Δ9 desaturase polypeptide according to claim 1; and,
      (ii) a source of palmitic acid;
   b.) growing the host cell of step (a) under conditions wherein the nucleic acid molecule encoding the Δ9 desaturase polypeptide is expressed and the palmitic acid is converted to palmitoleic acid.

13. A method according to either of claim 11 or 12 wherein the isolated nucleic acid molecule encodes a Δ9 desaturase polypeptide having the amino acid sequence as set forth in SEQ ID NO:2.

14. A method according to either of claim 11 or 12 wherein:
   a.) the isolated nucleic acid molecule has the nucleic acid sequence as set forth in SEQ ID NO:1; and,
   b.) the host cell is *Yarrowia lipolytica*.

15. A method according to either of claim 11 or 12, wherein the host cell is selected from the group consisting of: plants, algae, bacteria, yeast, euglenoids and fungi.

16. A method according to claim 15 wherein the host cell is a fungus selected from the group consisting of: *Thraustochytrium* sp., *Schizochytrium* sp, and *Mortierella* sp.

17. A method according to claim 15 wherein the yeast is an oleaginous yeast.

18. A method according to claim 17 wherein the oleaginous yeast is selected from the group consisting of: *Yarrowia, Candida, Rhodotorula, Rhodosporidium, Cryptococcus, Trichosporon* and *Lipomyces*.

19. A method according to claim 18 wherein the *Yarrowia* is selected from the group consisting of: *Yarrowia lipolytica* ATCC #20362, *Yarrowia lipolytica* ATCC #8862, *Yarrowia lipolytica* ATCC #18944, *Yarrowia lipolytica* ATCC #76982 and *Yarrowia lipolytica* LGAM S(7)1.

* * * * *

SEQUENCE LISTING

<160> NUMBER OF SEQ ID NOS: 63

<210> SEQ ID NO 1
<211> LENGTH: 1023
<212> TYPE: DNA
<213> ORGANISM: Euglena gracilis

```
<220> FEATURE:
<221> NAME/KEY: misc_feature
<223> OTHER INFORMATION: delta-9 desaturase

<400> SEQUENCE: 1
atggcagctg ttgcagagaa agacttggac accgatttaa atgtttcaac cgcgaaagaa    60
gagttgcgcc ttccacctta tgccggaaag gaacccttcc gacctgatgt cttccaacca   120
cgaagtgaag tcagggaaat ctttggcaca ggcatcaagt acatcaagaa gagaaactgg   180
tggtggccaa gaacctacaa ttcaacagat attgtcttta tccttgttac cttttccatg   240
catgcggctg cgctcatttt gggccccatg acatacaggc ctgattgttt ggctttgttt   300
ttgggattgt acgtggtcac tggactattt ggtatcacgc tgtcatacca tcgtcagctg   360
tcgcacaggt ccttcacgac accgaaatgg ttggaataca tcttcgctta ttgtggagtc   420
ttggcattcc agggtgatcc tctggaatgg gtgtgctctc acaggtatca tcaccaatat   480
tgcgagacag atcgtgatcc ccactctgtc aatgaaggat tctggtggtc tcatatggga   540
tggttgcttg accaccaggc aacaaagaca cggactggag accagactaa ctccatggac   600
atcatgaacg accctttcta cagcttcatc aggaagacct atcctttgca tttggcgctg   660
tttgccctgg ccctctatgc ctggggtggc attccgtatt tggtgtgggg cgtggcagtc   720
cgagtgtgct gggtctggca catcacctgg tttgtgaact ctgctgttca cacttggggc   780
aacaaggtgt acaagaccaa ccctccagat gagtctcgca caactggtg ggtcggcctc    840 cttgcatggg gtgagggatg gcacaacaac caccacgcat tccagtactc tgctcgccac   900
ggcttggaat ggtggcaagt tgacatgacg tggggtgtga ttcgggttct gcagttcttg   960
gggctggcca ccaatgtcaa gctgccttct gaggaaagga aggctgccat gcgccttgcc  1020
taa                                                                1023

<210> SEQ ID NO 2
<211> LENGTH: 340
<212> TYPE: PRT
<213> ORGANISM: Euglena gracilis
<220> FEATURE:
<221> NAME/KEY: MISC_FEATURE
<223> OTHER INFORMATION: delta-9 desaturase

<400> SEQUENCE: 2

Met Ala Ala Val Ala Glu Lys Asp Leu Asp Thr Asp Leu Asn Val Ser
1               5                   10                  15

Thr Ala Lys Glu Glu Leu Arg Leu Pro Pro Tyr Ala Gly Lys Glu Pro
                20                  25                  30

Phe Arg Pro Asp Val Phe Gln Pro Arg Ser Glu Val Arg Glu Ile Phe
            35                  40                  45

Gly Thr Gly Ile Lys Tyr Ile Lys Lys Arg Asn Trp Trp Trp Pro Arg
        50                  55                  60

Thr Tyr Asn Ser Thr Asp Ile Val Phe Ile Leu Val Thr Phe Ser Met
65                  70                  75                  80

His Ala Ala Ala Leu Ile Leu Gly Pro Met Thr Tyr Arg Pro Asp Cys
                85                  90                  95

Leu Ala Leu Phe Leu Gly Leu Tyr Val Val Thr Gly Leu Phe Gly Ile
            100                 105                 110

Thr Leu Ser Tyr His Arg Gln Leu Ser His Arg Ser Phe Thr Thr Pro
        115                 120                 125

Lys Trp Leu Glu Tyr Ile Phe Ala Tyr Cys Gly Val Leu Ala Phe Gln
    130                 135                 140
```

```
Gly Asp Pro Leu Glu Trp Val Cys Ser His Arg Tyr His His Gln Tyr
145                 150                 155                 160

Cys Glu Thr Asp Arg Asp Pro His Ser Val Asn Glu Gly Phe Trp Trp
            165                 170                 175

Ser His Met Gly Trp Leu Leu Asp His Gln Ala Thr Lys Thr Arg Thr
            180                 185                 190

Gly Asp Gln Thr Asn Ser Met Asp Ile Met Asn Asp Pro Phe Tyr Ser
            195                 200                 205

Phe Ile Arg Lys Thr Tyr Pro Leu His Leu Ala Leu Phe Ala Leu Ala
210                 215                 220

Leu Tyr Ala Trp Gly Gly Ile Pro Tyr Leu Val Trp Gly Val Ala Val
225                 230                 235                 240

Arg Val Cys Trp Val Trp His Ile Thr Trp Phe Val Asn Ser Ala Val
            245                 250                 255

His Thr Trp Gly Asn Lys Val Tyr Lys Thr Asn Pro Pro Asp Glu Ser
            260                 265                 270

Arg Asn Asn Trp Trp Val Gly Leu Leu Ala Trp Gly Glu Gly Trp His
            275                 280                 285

Asn Asn His His Ala Phe Gln Tyr Ser Ala Arg His Gly Leu Glu Trp
290                 295                 300

Trp Gln Val Asp Met Thr Trp Gly Val Ile Arg Val Leu Gln Phe Leu
305                 310                 315                 320

Gly Leu Ala Thr Asn Val Lys Leu Pro Ser Glu Glu Arg Lys Ala Ala
            325                 330                 335

Met Arg Leu Ala
            340

<210> SEQ ID NO 3
<211> LENGTH: 572
<212> TYPE: DNA
<213> ORGANISM: Artificial Sequence
<220> FEATURE:
<223> OTHER INFORMATION: 572 bp fragment of pT-F4-1

<400> SEQUENCE: 3
ggacatcatg tttataccaa gaagagaaac tggtggtggc caagaaccta caattcaaca      60
gatattgtct ttatccttgt tacctttttcc atgcatgcgg ctgcgctcat tttgggcccc    120
atgacataca ggcctgattg tttggctttg ttttttgggat tgtacgtggt cactggacta    180
tttggtatca cgctgtcata ccatcgtcag ctgtcgcaca ggtccttcac gacaccgaaa    240
tggttggaat acatcttcgc ttattgtgga gtcttggcat tccagggtga tcctctggaa    300
tgggtgtgct ctcacaggta tcatcaccaa tattgcgaga cagatcgtga tccccactct    360
gtcaatgaag gattctggtg gtctcatatg ggatggttgc ttgaccacca ggcaacaaag    420
acacggactg gagaccagac taactccatg gacatcatga acgacccttt ctacagcttc    480
atcaagaaga cctatccttt gcatttggcg ctgtttgccc tggccctcta tgcctggggt    540
ggcattccgt atttggtata aacatgatga cc                                  572

<210> SEQ ID NO 4
<211> LENGTH: 186
<212> TYPE: PRT
<213> ORGANISM: Artificial Sequence
<220> FEATURE:
<223> OTHER INFORMATION: Translation of bases 1-558 of 572 bp fragment
      of pT-F4-1

<400> SEQUENCE: 4
```

```
Gly His His Val Tyr Thr Lys Lys Arg Asn Trp Trp Pro Arg Thr
1               5                   10                  15

Tyr Asn Ser Thr Asp Ile Val Phe Ile Leu Val Thr Phe Ser Met His
            20                  25                  30

Ala Ala Ala Leu Ile Leu Gly Pro Met Thr Tyr Arg Pro Asp Cys Leu
        35                  40                  45

Ala Leu Phe Leu Gly Leu Tyr Val Val Thr Gly Leu Phe Gly Ile Thr
    50                  55                  60

Leu Ser Tyr His Arg Gln Leu Ser His Arg Ser Phe Thr Thr Pro Lys
65              70                  75                  80

Trp Leu Glu Tyr Ile Phe Ala Tyr Cys Gly Val Leu Ala Phe Gln Gly
            85                  90                  95

Asp Pro Leu Glu Trp Val Cys Ser His Arg Tyr His His Gln Tyr Cys
        100                 105                 110

Glu Thr Asp Arg Asp Pro His Ser Val Asn Glu Gly Phe Trp Trp Ser
    115                 120                 125

His Met Gly Trp Leu Leu Asp His Gln Ala Thr Lys Thr Arg Thr Gly
            130                 135                 140

Asp Gln Thr Asn Ser Met Asp Ile Met Asn Asp Pro Phe Tyr Ser Phe
145                 150                 155                 160

Ile Lys Lys Thr Tyr Pro Leu His Leu Ala Leu Phe Ala Leu Ala Leu
                165                 170                 175

Tyr Ala Trp Gly Gly Ile Pro Tyr Leu Val
                180                 185
```

<210> SEQ ID NO 5
<211> LENGTH: 653
<212> TYPE: DNA
<213> ORGANISM: Artificial Sequence
<220> FEATURE:
<223> OTHER INFORMATION: 653 bp fragment of pT-EgD9-5'C2

<400> SEQUENCE: 5

```
ggcggtcaga gcggcggcgg gcaggggggg ggcaacacgg aaggaatgag gggcgaggag    60
gtctgcagag gggggtttgc cgggtcacag ggcggtcgga accaaagcct tggtccatgg   120
cagctgttgc agagaaagac ttggacaccg atttaaatgt ttcaaccgcg aaagaagagt   180
tgcgccttcc accttatgcc ggaaaggaac ccttccgacc tgatgtcttc caaccacgaa   240
gtgaagtcag ggaaatcttt ggcacaggca tcaagtacat caagaagaga actggtggt    300
ggccaagaac ctacaattca acagatattg tctttatcct tgttaccttt tccatgcatg   360
cagctgcgct cattttgggc cccatgacat acaggcctga ttgtttggct ttgttttttgg  420
gattgtacgt gatcactgga ctatttggta tcacgctgtc ataccatcgt cagctgtcgc   480
acaggtcctt cacgacaccg aaatggttgg aatacatctt cgcttattgt ggagtcttgg   540
cattccaggg tgatcctctg aatgggtgt gctctcacag gtatcatcac caatattgcg    600
agacagatcg tgatccccac tctgtcaatg aaggattctg gtggtctcat atg           653
```

<210> SEQ ID NO 6
<211> LENGTH: 266
<212> TYPE: DNA
<213> ORGANISM: Artificial Sequence
<220> FEATURE:
<223> OTHER INFORMATION: 260 bp 5' region of pT-EgD5-5'C2

<400> SEQUENCE: 6

```
ggcggtcaga gcggcggcgg gcaggggggg ggcaacacgg aaggaatgag gggcgaggag    60
```

```
gtctgcagag gggggtttgc cgggtcacag ggcggtcgga accaaagcct tggtccatgg      120
cagctgttgc agagaaagac ttggacaccg atttaaatgt tcaaccgcg aaagaagagt       180 tgcgccttcc accttatgcc ggaaaggaac ccttccgacc tgatgtcttc caaccacgaa      240
gtgaagtcag ggaaatcttt ggcaca                                            266

<210> SEQ ID NO 7
<211> LENGTH: 150
<212> TYPE: DNA
<213> ORGANISM: Artificial Sequence
<220> FEATURE:
<223> OTHER INFORMATION: 150 bp 5' coding region of pT-EgD5-5'C2

<400> SEQUENCE: 7
atggcagctg ttgcagagaa agacttggac accgatttaa atgtttcaac cgcgaaagaa        60
gagttgcgcc ttccaccta tgccggaaag gaacccttcc gacctgatgt cttccaacca       120
cgaagtgaag tcagggaaat ctttggcaca                                        150

<210> SEQ ID NO 8
<211> LENGTH: 116
<212> TYPE: DNA
<213> ORGANISM: Artificial Sequence
<220> FEATURE:
<223> OTHER INFORMATION: 116 bp 5' untranslated region of pT-EgD5-5'C2

<400> SEQUENCE: 8
ggcggtcaga gcggcggcgg gcaggggggg ggcaacacgg aaggaatgag gggcgaggag        60
gtctgcagag gggggtttgc cgggtcacag ggcggtcgga accaaagcct tggtcc          116

<210> SEQ ID NO 9
<211> LENGTH: 660
<212> TYPE: DNA
<213> ORGANISM: Artificial Sequence
<220> FEATURE:
<223> OTHER INFORMATION: 660 bp fragment of pT-EgD9-3'

<400> SEQUENCE: 9
gaacgaccct tctacagctt catcaggaag acctatcctt tgcatttggc gctgtttgcc        60
ctggccctct atgcctgggg tggcattccg tatttggtgt ggggcgtggc agtccgagtg      120
tgctgggtct ggcacatcac ctggtttgtg aactctgctg ttcacacttg ggcaacaag       180 gtgtacaaga ccaacccctc cagatgagtct cgcaacaact ggtgggtcgg cctccttgca    240
tggggtgagg gatggcacaa caaccaccac gcattccagt actctgctcg ccacggcttg      300
gagtggtggc aagttgacat gacgtggggc gtgattcggg ttctgcagtt cttggggctg      360
gccaccaatg tcaagctgcc ttctgaggaa aggaaggctg ccatgcgcct tgcctaaaac      420
gcagcggagg agccttgctg tgtttgaaag caatgccact gccggtgtat tgtacaggaa      480
cgcttctaat tttcggattt cttttgcttt attgtgccag tcttccacag taccatttct      540
tatgcatcat tattaccctc tgatgggtac agtgccaaag acgtcgcact tgttatagcc      600
atcgattgct atgggtgcag ttgacaccgt ccgcaggttt gccgccagtt gtcatttgca     660

<210> SEQ ID NO 10
<211> LENGTH: 543
<212> TYPE: DNA
<213> ORGANISM: Artificial Sequence
<220> FEATURE:
<223> OTHER INFORMATION: 543 bp 3' region of pT-EgD9-3'

<400> SEQUENCE: 10
```

```
gtgtgctggg tctggcacat cacctggttt gtgaactctg ctgttcacac ttggggcaac      60
aaggtgtaca agaccaaccc tccagatgag tctcgcaaca actggtgggt cggcctcctt     120
gcatggggtg agggatggca caacaaccac cacgcattcc agtactctgc tcgccacggc     180
ttggagtggt ggcaagttga catgacgtgg ggcgtgattc gggttctgca gttcttgggg     240
ctggccacca atgtcaagct gccttctgag gaaaggaagg ctgccatgcg ccttgcctaa     300
aacgcagcgg aggagccttg ctgtgtttga aagcaatgcc actgccggtg tattgtacag     360
gaacgcttct aattttcgga tttcttttgc tttattgtgc cagtcttcca cagtaccatt     420
tcttatgcat cattattacc ctctgatggg tacagtgcca aagacgtcgc acttgttata     480
gccatcgatt gctatgggtg cagttgacac cgtccgcagg tttgccgcca gttgtcattt     540
gca                                                                   543

<210> SEQ ID NO 11
<211> LENGTH: 300
<212> TYPE: DNA
<213> ORGANISM: Artificial Sequence
<220> FEATURE:
<223> OTHER INFORMATION: 300 bp 3' coding region of pT-EgD9-3'

<400> SEQUENCE: 11
gtgtgctggg tctggcacat cacctggttt gtgaactctg ctgttcacac ttggggcaac      60
aaggtgtaca agaccaaccc tccagatgag tctcgcaaca actggtgggt cggcctcctt     120
gcatggggtg agggatggca caacaaccac cacgcattcc agtactctgc tcgccacggc     180
ttggagtggt ggcaagttga catgacgtgg ggcgtgattc gggttctgca gttcttgggg     240
ctggccacca atgtcaagct gccttctgag gaaaggaagg ctgccatgcg ccttgcctaa     300

<210> SEQ ID NO 12
<211> LENGTH: 243
<212> TYPE: DNA
<213> ORGANISM: Artificial Sequence
<220> FEATURE:
<223> OTHER INFORMATION: 243 bp 3' untranslated region of pT-EgD9-3'

<400> SEQUENCE: 12
aacgcagcgg aggagccttg ctgtgtttga aagcaatgcc actgccggtg tattgtacag      60
gaacgcttct aattttcgga tttcttttgc tttattgtgc cagtcttcca cagtaccatt     120
tcttatgcat cattattacc ctctgatggg tacagtgcca aagacgtcgc acttgttata     180
gccatcgatt gctatgggtg cagttgacac cgtccgcagg tttgccgcca gttgtcattt     240
gca                                                                   243

<210> SEQ ID NO 13
<211> LENGTH: 37
<212> TYPE: DNA
<213> ORGANISM: Artificial Sequence
<220> FEATURE:
<223> OTHER INFORMATION: Primer AP

<400> SEQUENCE: 13
ggccacgcgt cgactagtac tttttttttt tttttttt                              37

<210> SEQ ID NO 14
<211> LENGTH: 39
<212> TYPE: DNA
<213> ORGANISM: Artificial Sequence
<220> FEATURE:
<223> OTHER INFORMATION: Smart IV oligonucleotide primer
```

```
<400> SEQUENCE: 14
aagcagtggt atcaacgcag agtggccatt acggccggg                            39

<210> SEQ ID NO 15
<211> LENGTH: 23
<212> TYPE: DNA
<213> ORGANISM: Artificial Sequence
<220> FEATURE:
<223> OTHER INFORMATION: CDSIII 5' primer

<400> SEQUENCE: 15
aagcagtggt atcaacgcag agt                                             23

<210> SEQ ID NO 16
<211> LENGTH: 469
<212> TYPE: PRT
<213> ORGANISM: Phaeodactylum tricornutum (GenBank Accession No.
       AAL92562)
<220> FEATURE:
<221> NAME/KEY: MISC_FEATURE
<223> OTHER INFORMATION: delta-5 desaturase

<400> SEQUENCE: 16
```

Met Ala Pro Asp Ala Asp Lys Leu Arg Gln Arg Gln Thr Thr Ala Val
1               5                   10                  15

Ala Lys His Asn Ala Ala Thr Ile Ser Thr Gln Glu Arg Leu Cys Ser
            20                  25                  30

Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp

-continued

```
                275                 280                 285
Asn Ala Phe Ile His Ser Arg Arg Lys Tyr Ala Val Phe Trp Arg Ala
    290                 295                 300
Val Tyr Ile Ala Val Asn Val Ile Ala Pro Phe Tyr Thr Asn Ser Gly
305                 310                 315                 320
Leu Glu Trp Ser Trp Arg Val Phe Gly Asn Ile Met Leu Met Gly Val
                325                 330                 335
Ala Glu Ser Leu Ala Leu Ala Val Leu Phe Ser Leu Ser His Asn Phe
            340                 345                 350
Glu Ser Ala Asp Arg Asp Pro Thr Ala Pro Leu Lys Lys Thr Gly Glu
        355                 360                 365
Pro Val Asp Trp Phe Lys Thr Gln Val Glu Thr Ser Cys Thr Tyr Gly
370                 375                 380
Gly Phe Leu Ser Gly Cys Phe Thr Gly Gly Leu Asn Phe Gln Val Glu
385                 390                 395                 400
His His Leu Phe Pro Arg Met Ser Ser Ala Trp Tyr Pro Tyr Ile Ala
                405                 410                 415
Pro Lys Val Arg Glu Ile Cys Ala Lys His Gly Val His Tyr Ala Tyr
            420                 425                 430
Tyr Pro Trp Ile His Gln Asn Phe Leu Ser Thr Val Arg Tyr Met His
        435                 440                 445
Ala Ala Gly Thr Gly Ala Asn Trp Arg Gln Met Ala Arg Glu Asn Pro
    450                 455                 460
Leu Thr Gly Arg Ala
465

<210> SEQ ID NO 17
<211> LENGTH: 477
<212> TYPE: PRT
<213> ORGANISM: Phytophthora megasperma (GenBank Accession No. CAD53323)
<220> FEATURE:
<221> NAME/KEY: MISC_FEATURE
<223> OTHER INFORMATION: delta-5 desaturase

<400> SEQUENCE: 17

Met Ala Pro Ile Glu Thr Val Lys Asp Ala Asn Glu Gly Leu His Gln
1               5                   10                  15
Arg Lys Gly Ala Ala Ala Ser Lys Asp Thr Thr Thr Phe Thr Trp
            20                  25                  30
Gln Asp Val Ala Lys His Asn Thr Ala Lys Ser Ala Trp Val Thr Ile
        35                  40                  45
Arg Gly Val Val Tyr Asp Val Thr Glu Trp Ala Asp Arg His Pro Gly
    50                  55                  60
Gly Arg Glu Leu Val Leu Leu His Ser Gly Arg Glu Cys Thr Asp Thr
65                  70                  75                  80
Phe Asp Ser Tyr His Pro Phe Ser Asp Arg Ala Asp Lys Ile Leu Ala
                85                  90                  95
Lys Tyr Ala Ile Gly Lys Leu Val Gly Gly Ser Glu Phe Pro Thr Tyr
            100                 105                 110
Lys Pro Asp Thr Gly Phe Tyr Lys Glu Cys Cys Asp Arg Val Asn Gln
        115                 120                 125
Tyr Phe Lys Asp Asn Lys Leu Asp Pro Arg Ser Pro Tyr Ser Gly Leu
    130                 135                 140
Trp Arg Met Ile Leu Val Ala Ile Val Gly Ala Val Ala Tyr Met Gly
145                 150                 155                 160
Met Asn Gln Leu Leu Pro Gly Asn Ile Tyr Ala His Tyr Ala Trp Gly
```

```
                        165                 170                 175
Ala Leu Phe Gly Val Cys Gln Ala Leu Pro Leu Leu His Val Met His
            180                 185                 190

Asp Ala Ser His Ala Ala Ile Thr Ser Ser Pro Thr Gly Trp Arg Leu
            195                 200                 205

Ile Gly Arg Leu Ala Met Asp Trp Val Ala Gly Ala Asn Met Val Ser
            210                 215                 220

Trp Leu Asn Gln His Val Gly His His Ile Tyr Thr Asn Val Ala
225                 230                 235                 240

Gly Ala Asp Pro Asp Leu Pro Val Asp Phe Lys Ser Asp Val Arg Arg
                    245                 250                 255

Ile Val Tyr Arg Gln Val Leu Leu Pro Ile Tyr Lys Tyr Gln His Leu
            260                 265                 270

Tyr Leu Pro Pro Leu Tyr Gly Val Leu Gly Leu Lys Phe Arg Val Gln
            275                 280                 285

Asp Val Phe Glu Thr Phe Val Thr Leu Thr Asn Gly Pro Leu Arg Val
            290                 295                 300

Asn Pro Leu Ser Val Gly Asp Trp Ala Glu Met Ile Leu Ser Lys Ala
305                 310                 315                 320

Phe Trp Val Phe Tyr Arg Ile Tyr Leu Pro Leu Ala Val Leu Gln Val
                    325                 330                 335

Asp Pro Ala Arg Phe Trp Gly Val Phe Leu Ala Glu Phe Ser Thr
            340                 345                 350

Gly Trp Tyr Leu Ala Phe Asn Phe Gln Val Ser His Val Ser Thr Ala
            355                 360                 365

Cys Glu Tyr Pro Gly Gly Asp Glu Glu Val Thr Ser Ile Asp Asp Glu
370                 375                 380

Trp Ala Ile Ser Gln Val Lys Ser Ser Val Asp Tyr Gly His Gly Ser
385                 390                 395                 400

Phe Ile Thr Thr Phe Leu Thr Gly Ala Leu Asn Tyr Gln Val Thr His
                    405                 410                 415

His Leu Phe Pro Gly Val Ser Gln Tyr His Tyr Pro Ala Ile Ala Pro
            420                 425                 430

Leu Ile Leu Asp Val Cys His Lys Tyr Lys Val Lys Tyr Asn Val Leu
            435                 440                 445

Pro Asp Phe Thr Ala Ala Met Ala Gly His Phe Asp His Leu Val Ile
            450                 455                 460

Met Gly Lys Met Gly Lys Arg Val Thr Ile His Met Gly
465                 470                 475

<210> SEQ ID NO 18
<211> LENGTH: 456
<212> TYPE: PRT
<213> ORGANISM: Pythium irregulare (GenBank Accession No. AAL13311)
<220> FEATURE:
<221> NAME/KEY: MISC_FEATURE
<223> OTHER INFORMATION: delta-5 desaturase

<400> SEQUENCE: 18

Met Gly Thr Asp Gln Gly Lys Thr Phe Thr Trp Gln Glu Val Ala Lys
1               5                   10                  15

His Asn Thr Ala Lys Ser Ala Trp Val Ile Ile Arg Gly Glu Val Tyr
                20                  25                  30

Asp Val Thr Glu Trp Ala Asp Lys His Pro Gly Gly Ser Glu Leu Ile
            35                  40                  45

Val Leu His Ser Gly Arg Glu Cys Thr Asp Thr Phe Tyr Ser Tyr His
```

```
                50                  55                  60
Pro Phe Ser Asn Arg Ala Asp Lys Ile Leu Ala Lys Tyr Lys Ile Gly
65                  70                  75                  80

Lys Leu Val Gly Gly Tyr Glu Phe Pro Val Phe Lys Pro Asp Ser Gly
                85                  90                  95

Phe Tyr Lys Glu Cys Ser Glu Arg Val Ala Glu Tyr Phe Lys Thr Asn
                100                 105                 110

Asn Leu Asp Pro Lys Ala Ala Phe Ala Gly Leu Trp Arg Met Val Phe
            115                 120                 125

Val Phe Ala Val Ala Ala Leu Ala Tyr Met Gly Met Asn Glu Leu Ile
        130                 135                 140

Pro Gly Asn Val Tyr Ala Gln Tyr Ala Trp Gly Val Phe Gly Val
145                 150                 155                 160

Phe Gln Ala Leu Pro Leu Leu His Val Met His Asp Ser Ser His Ala
                165                 170                 175

Ala Cys Ser Ser Ser Pro Ala Met Trp Gln Ile Ile Gly Arg Gly Val
                180                 185                 190

Met Asp Trp Phe Ala Gly Ala Ser Met Val Ser Trp Leu Asn Gln His
            195                 200                 205

Val Val Gly His His Ile Tyr Thr Asn Val Ala Gly Ala Asp Pro Asp
        210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr
                260                 265                 270

Phe Val Ser Leu Thr Asn Gly Pro Val Arg Val Asn Pro His Pro Val
            275                 280                 285

Ser Asp Trp Val Gln Met Ile Phe Ala Lys Ala Phe Trp Thr Phe Tyr
        290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
                340                 345                 350

Gly Asp Ala Pro Ser Ala Glu Val Gly Asp Glu Trp Ala Ile Ser Gln
            355                 360                 365

Val Lys Ser Ser Val Asp Tyr Ala His Gly Ser Pro Leu Ala Ala Phe
        370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Ile Asp Val
                405                 410                 415

Cys Lys Lys Tyr Asn Ile Lys Tyr Thr Val Leu Pro Thr Phe Thr Glu
                420                 425                 430

Ala Leu Leu Ala His Phe Lys His Leu Lys Asn Met Gly Glu Leu Gly
            435                 440                 445

Lys Pro Val Glu Ile His Met Gly
        450                 455

<210> SEQ ID NO 19
<211> LENGTH: 467
```

-continued

```
<212> TYPE: PRT
<213> ORGANISM: Dictyostelium discoideum (GenBank Accession No.
      XP_640331)
<220> FEATURE:
<221> NAME/KEY: MISC_FEATURE
<223> OTHER INFORMATION: delta-5 desaturase

<400> SEQUENCE: 19

Met Met Glu Thr Asn Asn Glu Asn Lys Glu Lys Leu Lys Leu Tyr Thr
1               5                   10                  15

Trp Asp Glu Val Ser Lys His Asn Gln Lys Asn Asp Leu Trp Ile Ile
            20                  25                  30

Val Asp Gly Lys Val Tyr Asn Ile Thr Lys Trp Val Pro Leu His Pro
        35                  40                  45

Gly Gly Glu Asp Ile Leu Leu Leu Ser Ala Gly Arg Asp Ala Thr Asn
    50                  55                  60

Leu Phe Glu Ser Tyr His Pro Met Thr Asp Lys His Tyr Ser Leu Ile
65                  70                  75                  80

Lys Gln Tyr Glu Ile Gly Tyr Ile Ser Ser Tyr Glu His Pro Lys Tyr
                85                  90                  95

Val Glu Lys Ser Glu Phe Tyr Ser Thr Leu Lys Gln Arg Val Arg Lys
            100                 105                 110

His Phe Gln Thr Ser Ser Gln Asp Pro Lys Val Ser Val Gly Val Phe
        115                 120                 125

Thr Arg Met Val Leu Ile Tyr Leu Phe Leu Val Thr Tyr Tyr Leu
    130                 135                 140

Ser Gln Phe Ser Thr Asp Arg Phe Trp Leu Asn Cys Ile Phe Ala Val
145                 150                 155                 160

Leu Tyr Gly Val Ala Asn Ser Leu Phe Gly Leu His Thr Met His Asp
                165                 170                 175

Ala Cys His Thr Ala Ile Thr His Asn Pro Met Thr Trp Lys Ile Leu
            180                 185                 190

Gly Ala Thr Phe Asp Leu Phe Ala Gly Ala Ser Phe Tyr Ala Trp Cys
        195                 200                 205

His Gln His Val Ile Gly His His Leu Tyr Thr Asn Val Arg Asn Ala
    210                 215                 220

Asp Pro Asp Leu Gly Gln Gly Glu Ile Asp Phe Arg Val Val Thr Pro
225                 230                 235                 240

Tyr Gln Ala Arg Ser Trp Tyr His Lys Tyr Gln His Ile Tyr Ala Pro
                245                 250                 255

Ile Leu Tyr Gly Val Tyr Ala Leu Lys Tyr Arg Ile Gln Asp His Glu
            260                 265                 270

Ile Phe Thr Lys Lys Ser Asn Gly Ala Ile Arg Tyr Ser Pro Ile Ser
        275                 280                 285

Thr Ile Asp Thr Ala Ile Phe Ile Leu Gly Lys Leu Val Phe Ile Ile
    290                 295                 300

Ser Arg Phe Ile Leu Pro Leu Ile Tyr Asn His Ser Phe Ser His Leu
305                 310                 315                 320

Ile Cys Phe Phe Leu Ile Ser Glu Leu Val Leu Gly Trp Tyr Leu Ala
                325                 330                 335

Ile Ser Phe Gln Val Ser His Val Val Glu Asp Leu Gln Phe Met Ala
            340                 345                 350

Thr Pro Glu Ile Phe Asp Gly Ala Asp His Pro Leu Pro Thr Thr Phe
        355                 360                 365

Asn Gln Asp Trp Ala Ile Leu Gln Val Lys Thr Thr Gln Asp Tyr Ala
    370                 375                 380
```

```
Gln Asp Ser Val Leu Ser Thr Phe Phe Ser Gly Gly Leu Asn Leu Gln
385                 390                 395                 400

Val Ile His His Cys Phe Pro Thr Ile Ala Gln Asp Tyr Tyr Pro Gln
            405                 410                 415

Ile Val Pro Ile Leu Lys Glu Val Cys Lys Glu Tyr Asn Val Thr Tyr
        420                 425                 430

His Tyr Lys Pro Thr Phe Thr Glu Ala Ile Lys Ser His Ile Asn Tyr
    435                 440                 445

Leu Tyr Lys Met Gly Asn Asp Pro Asp Tyr Val Arg Lys Pro Val Asn
450                 455                 460

Lys Asn Asp
465

<210> SEQ ID NO 20
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012325
<311> PATENT FILING DATE: 2005-06-24
<312> PUBLICATION DATE: 2006-02-02
<313> RELEVANT RESIDUES: (1)..(421)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO2006012326
<311> PATENT FILING DATE: 2005-06-24
<312> PUBLICATION DATE: 2006-02-02
<313> RELEVANT RESIDUES: (1)..(421)

<400> SEQUENCE: 20

Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190
```

```
Gly His Asp Pro Asp Ile Asp Asn Leu Pro Leu Leu Ala Trp Ser Glu
        195                 200                 205
Asp Asp Val Thr Arg Ala Ser Pro Ile Ser Arg Lys Leu Ile Gln Phe
    210                 215                 220
Gln Gln Tyr Tyr Phe Leu Val Ile Cys Ile Leu Leu Arg Phe Ile Trp
225                 230                 235                 240
Cys Phe Gln Ser Val Leu Thr Val Arg Ser Leu Lys Asp Arg Asp Asn
            245                 250                 255
Gln Phe Tyr Arg Ser Gln Tyr Lys Lys Glu Ala Ile Gly Leu Ala Leu
                260                 265                 270
His Trp Thr Leu Lys Thr Leu Phe His Leu Phe Met Pro Ser Ile
            275                 280                 285
Leu Thr Ser Leu Leu Val Phe Phe Val Ser Glu Leu Val Gly Gly Phe
    290                 295                 300
Gly Ile Ala Ile Val Val Phe Met Asn His Tyr Pro Leu Glu Lys Ile
305                 310                 315                 320
Gly Asp Ser Val Trp Asp Gly His Gly Phe Ser Val Gly Gln Ile His
                325                 330                 335
Glu Thr Met Asn Ile Arg Arg Gly Ile Ile Thr Asp Trp Phe Phe Gly
            340                 345                 350
Gly Leu Asn Tyr Gln Ile Glu His His Leu Trp Pro Thr Leu Pro Arg
        355                 360                 365
His Asn Leu Thr Ala Val Ser Tyr Gln Val Glu Gln Leu Cys Gln Lys
    370                 375                 380
His Asn Leu Pro Tyr Arg Asn Pro Leu Pro His Glu Gly Leu Val Ile
385                 390                 395                 400
Leu Leu Arg Tyr Leu Ala Val Phe Ala Arg Met Ala Glu Lys Gln Pro
                405                 410                 415
Ala Gly Lys Ala Leu
            420

<210> SEQ ID NO 21
<211> LENGTH: 1269
<212> TYPE: DNA
<213> ORGANISM: Pavlova lutheri
<220> FEATURE:
<221> NAME/KEY: misc_feature
<223> OTHER INFORMATION: delta-8 desaturase

<400> SEQUENCE: 21
atgggcaagg gtggagacgg cggcgcgcag gcggtgagcg ggaccgacgc gtctctcgct      60
gaggtgagct ccgtcgatag caagagcgtg cacgtcgtgc tctacggcaa gcgcgtggat     120
gtcacaaagt tccagaaggc acacccgggc gggagcaagg tgttccgcat cttccaggag     180
cgcgacgcga cggagcagtt cgagtcttac cactcgccca aggccatcaa gatgatggag     240
ggcatgctca agaagtcgga ggatgcgccc gcttccgtgc ccctgccctc gcggtccacc     300
atgggcacgg agttcaagga gatgattgag cgccacaaga gggctggtct ctacgaccct     360
tgcccgttgg acgagctgtt caagctcacc atcgtcctcg cgccatctct cgtgggcgcc     420
tatctcgtgc ggagcggcgt ctcgcccctc gcgggcgcgc tctccatggg ctttggcttc     480
tacctcgacg gctggcttgc tcacgactac ctgcatcacg cagtcttcaa gggctcggtc     540
aacacgctcg tcaaggcgaa caacgccatg ggatacgccc tcggcttcct ccagggctac     600
gacgtggcct ggtggcgcgc gcgccataac acgcaccacg tgtgcaccaa cgaggatggt     660
tcggacccgg acatcaagac ggcgcccctg ctcatctacg tgcgagagaa cccgtccatt     720
```

```
gccaagcggc tcaacttctt ccagcgctgg cagcagtact actatgtgcc gaccatggcc      780
atcctcgacc tctactggcg cctggagtcc atcgcgtacg tggctgtgcg cctgcctaag      840
atgtggatgc aggccgccgc tcttgccgct cactacgcgc tcctgtgctg ggtcttcgca      900
gcgcatctca acctcatccc tctcatgatg gttgcacgcg gcttcgcgac gggcatcgtt      960
gtctttgcaa cccactatgg tgaggacatc ctcgaccgcg agcacgtcga gggcatgacg     1020
ctcgtcgagc agaccgccaa gacctcccgt aacatcacgg gcggctggct agtgaacgtg     1080
ctcacgggct tcatctcccct gcagaccgag catcacctct ccccatgat gcccaccggc     1140 aacctaatga ctatccagcc cgaggtacgc gacttcttca gaagcatgg cctcgagtac      1200 cgcgagggca acctcttcca gtgcgtgcac cagaacatca aggctctcgc cttcgagcac     1260
ctcctccac                                                             1269
```

<210> SEQ ID NO 22
<211> LENGTH: 423
<212> TYPE: PRT
<213> ORGANISM: Pavlova lutheri

<400> SEQUENCE: 22

```
Met Gly Lys Gly Gly Asp Gly Gly Ala Gln Ala Val Ser Gly Thr Asp
1               5                   10                  15

Ala Ser Leu Ala Glu Val Ser Ser Val Asp Ser Lys Ser Val His Val
            20                  25                  30

Val Leu Tyr Gly Lys Arg Val Asp Val Thr Lys Phe Gln Lys Ala His
        35                  40                  45

Pro Gly Gly Ser Lys Val Phe Arg Ile Phe Gln Glu Arg Asp Ala Thr
    50                  55                  60

Glu Gln Phe Glu Ser Tyr His Ser Pro Lys Ala Ile Lys Met Met Glu
65                  70                  75                  80

Gly Met Leu Lys Lys Ser Glu Asp Ala Pro Ala Ser Val Pro Leu Pro
                85                  90                  95

Ser Arg Ser Thr Met Gly Thr Glu Phe Lys Glu Met Ile Glu Arg His
            100                 105                 110

Lys Arg Ala Gly Leu Tyr Asp Pro Cys Pro Leu Asp Glu Leu Phe Lys
        115                 120                 125

Leu Thr Ile Val Leu Ala Pro Ile Phe Val Gly Ala Tyr Leu Val Arg
    130                 135                 140

Ser Gly Val Ser Pro Leu Ala Gly Ala Leu Ser Met Gly Phe Gly Phe
145                 150                 155                 160

Tyr Leu Asp Gly Trp Leu Ala His Asp Tyr Leu His His Ala Val Phe
                165                 170                 175

Lys Gly Ser Val Asn Thr Leu Val Lys Ala Asn Asn Ala Met Gly Tyr
            180                 185                 190

Ala Leu Gly Phe Leu Gln Gly Tyr Asp Val Ala Trp Trp Arg Ala Arg
        195                 200                 205

His Asn Thr His His Val Cys Thr Asn Glu Asp Gly Ser Asp Pro Asp
    210                 215                 220

Ile Lys Thr Ala Pro Leu Leu Ile Tyr Val Arg Glu Asn Pro Ser Ile
225                 230                 235                 240

Ala Lys Arg Leu Asn Phe Phe Gln Arg Trp Gln Gln Tyr Tyr Tyr Val
                245                 250                 255

Pro Thr Met Ala Ile Leu Asp Leu Tyr Trp Arg Leu Glu Ser Ile Ala
            260                 265                 270

Tyr Val Ala Val Arg Leu Pro Lys Met Trp Met Gln Ala Ala Ala Leu
```

```
                    275                 280                 285
Ala Ala His Tyr Ala Leu Leu Cys Trp Val Phe Ala Ala His Leu Asn
            290                 295                 300

Leu Ile Pro Leu Met Met Val Ala Arg Gly Phe Ala Thr Gly Ile Val
305                 310                 315                 320

Val Phe Ala Thr His Tyr Gly Glu Asp Ile Leu Asp Arg Glu His Val
                325                 330                 335

Glu Gly Met Thr Leu Val Glu Gln Thr Ala Lys Thr Ser Arg Asn Ile
            340                 345                 350

Thr Gly Gly Trp Leu Val Asn Val Leu Thr Gly Phe Ile Ser Leu Gln
        355                 360                 365

Thr Glu His His Leu Phe Pro Met Met Pro Thr Gly Asn Leu Met Thr
    370                 375                 380

Ile Gln Pro Glu Val Arg Asp Phe Phe Lys Lys His Gly Leu Glu Tyr
385                 390                 395                 400

Arg Glu Gly Asn Leu Phe Gln Cys Val His Gln Asn Ile Lys Ala Leu
                405                 410                 415

Ala Phe Glu His Leu Leu His
            420

<210> SEQ ID NO 23
<211> LENGTH: 7
<212> TYPE: PRT
<213> ORGANISM: Artificial Sequence
<220> FEATURE:
<223> OTHER INFORMATION: Conserved region #1 within delta-5 and delta-8
      desaturases
<220> FEATURE:
<221> NAME/KEY: MISC_FEATURE
<222> LOCATION: (4)..(4)
<223> OTHER INFORMATION: X = Ile or Val

<400> SEQUENCE: 23

Gly His His Xaa Tyr Thr Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Conserved region #2 within delta-5 and delta-8
      desaturases
<220> FEATURE:
<221> NAME/KEY: MISC_FEATURE
<222> LOCATION: (4)..(4)
<223> OTHER INFORMATION: X = Val or Ala
<220> FEATURE:
<221> NAME/KEY: MISC_FEATURE
<222> LOCATION: (5)..(5)
<223> OTHER INFORMATION: X = Ser or Asn

<400> SEQUENCE: 24

Asn Phe Gln Xaa Xaa His Val
1               5

<210> SEQ ID NO 25
<211> LENGTH: 20
<212> TYPE: DNA
<213> ORGANISM: Artificial Sequence
<220> FEATURE:
<223> OTHER INFORMATION: Primer 5-1A

<400> SEQUENCE: 25
gghcaycayr tbtayacaaa                                               20
```

<210> SEQ ID NO 26
<211> LENGTH: 20
<212> TYPE: DNA
<213> ORGANISM: Artificial Sequence
<220> FEATURE:
<223> OTHER INFORMATION: Primer 5-1B

<400> SEQUENCE: 26
gghcaycayr tbtayaccaa                                                     20

<210> SEQ ID NO 27
<211> LENGTH: 20
<212> TYPE: DNA
<213> ORGANISM: Artificial Sequence
<220> FEATURE:
<223> OTHER INFORMATION: Primer 5-1C

<400> SEQUENCE: 27
gghcaycayr tbtayacgaa                                                     20

<210> SEQ ID NO 28
<211> LENGTH: 20
<212> TYPE: DNA
<213> ORGANISM: Artificial Sequence
<220> FEATURE:
<223> OTHER INFORMATION: Primer 5-1D

<400> SEQUENCE: 28
gghcaycayr tbtayactaa                                                     20

<210> SEQ ID NO 29
<211> LENGTH: 20
<212> TYPE: DNA
<213> ORGANISM: Artificial Sequence
<220> FEATURE:
<223> OTHER INFORMATION: Primer 5-4AR
<220> FEATURE:
<221> NAME/KEY: misc_feature
<222> LOCATION: (9)..(9)
<223> OTHER INFORMATION: n is a, c, g, or t

<400> SEQUENCE: 29
acrtgrytna cytgraagtt                                                     20

<210> SEQ ID NO 30
<211> LENGTH: 20
<212> TYPE: DNA
<213> ORGANISM: Artificial Sequence
<220> FEATURE:
<223> OTHER INFORMATION: Primer 5-4BR
<220> FEATURE:
<221> NAME/KEY: misc_feature
<222> LOCATION: (9)..(9)
<223> OTHER INFORMATION: n is a, c, g, or t

<400> SEQUENCE: 30
acrtgrytna cytgraaatt                                                     20

<210> SEQ ID NO 31
<211> LENGTH: 20
<212> TYPE: DNA
<213> ORGANISM: Artificial Sequence
<220> FEATURE:
<223> OTHER INFORMATION: Primer 5-4CR
<220> FEATURE:
<221> NAME/KEY: misc_feature
<222> LOCATION: (6)..(6)
<223> OTHER INFORMATION: n is a, c, g, or t

```
<220> FEATURE:
<221> NAME/KEY: misc_feature
<222> LOCATION: (9)..(9)
<223> OTHER INFORMATION: n is a, c, g, or t

<400> SEQUENCE: 31
acrtgngana cytgraagtt                                                      20

<210> SEQ ID NO 32
<211> LENGTH: 20
<212> TYPE: DNA
<213> ORGANISM: Artificial Sequence
<220> FEATURE:
<223> OTHER INFORMATION: Primer 5-4DR
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 32
acrtgngana cytgraaatt                                                      20

<210> SEQ ID NO 33
<211> LENGTH: 371
<212> TYPE: PRT
<213> ORGANISM: Arabidopsis (GenBank Accession No. AAN41357)
<220> FEATURE:
<221> NAME/KEY: MISC_FEATURE
<223> OTHER INFORMATION: putative delta-9 desaturase

<400> SEQUENCE: 33
```

Met Ala Ser Leu Leu Thr Lys Pro Lys Pro Val Phe Leu Cys Ser Pro
1               5                   10                  15

Ser Leu Ser Pro Arg Thr Leu Asn Thr Ala Thr Pro Ser Leu Asn Phe
            20                  25                  30

Thr Arg Ile Ser Phe Thr His His Gln Lys Leu Ala Pro Phe Lys Pro
        35                  40                  45

Pro Ser Leu Val Val Ala Phe Ser Glu Lys Gly Leu Lys Arg Asp Val
    50                  55                  60

Thr Thr Ala Ala Ala Ala Thr Glu Gly Asp Tyr Arg Arg Ile Met Leu
65                  70                  75                  80

Ser Asp Val Leu Val Lys Lys Lys Glu Lys Val Val Trp Trp Glu Arg
                85                  90                  95

Glu Trp Lys Ala Met Asp Phe Gly Ala Val Ala Val Val Leu Ser Met
            100                 105                 110

His Leu Leu Ser Leu Leu Ala Pro Phe Gln Phe Asn Trp Arg Ala Val
        115                 120                 125

Ser Val Ala Phe Gly Leu Tyr Ile Val Thr Gly Leu Leu Gly Ile Thr
    130                 135                 140

Leu Ser Phe His Arg Asn Leu Ser His Lys Ala Phe Lys Leu Pro Lys
145                 150                 155                 160

Trp Leu Glu Tyr Leu Phe Ala Tyr Cys Gly Ala Gln Ala Leu Gln Gly
                165                 170                 175

Asn Pro Ile Asp Trp Val Ser Thr His Arg Tyr His His Gln Phe Cys
            180                 185                 190

Asp Ser Asp Arg Asp Pro His Ser Pro Leu Asp Gly Phe Trp Phe Ser
        195                 200                 205

His Met Asn Trp Met Phe Asp Thr Asn Thr Ile Thr Gln Arg Cys Gly

```
              210                 215                 220
Glu Pro Asn Asn Val Gly Asp Leu Glu Lys Gln Pro Phe Tyr Arg Phe
225                 230                 235                 240

Leu Arg Thr Thr Tyr Ile Leu His Pro Leu Ala Leu Ala Val Ala Leu
                245                 250                 255

Tyr Ala Met Gly Gly Phe Pro Phe Ile Val Trp Gly Met Gly Val Arg
                260                 265                 270

Ile Val Trp Val Tyr His Ile Thr Trp Leu Val Asn Ser Ala Cys His
                275                 280                 285

Val Trp Gly Lys Gln Ala Trp Asn Thr Gly Asp Leu Ser Lys Asn Asn
                290                 295                 300

Trp Trp Val Ala Ala Leu Ala Phe Gly Glu Gly Trp His Asn Asn His
305                 310                 315                 320

His Ala Phe Glu Phe Ser Ala Arg His Gly Leu Glu Trp Trp Gln Leu
                325                 330                 335

Asp Met Thr Trp Tyr Val Val Lys Phe Leu Gln Ala Ile Gly Leu Ala
                340                 345                 350

Thr Asp Val Lys Leu Pro Ser Glu Ala Gln Lys Gln Arg Met Ala Phe
                355                 360                 365

Thr Ser Asp
    370

<210> SEQ ID NO 34
<211> LENGTH: 382
<212> TYPE: PRT
<213> ORGANISM: Picea glauca (GenBank Accession No. AAM12238)
<220> FEATURE:
<221> NAME/KEY: MISC_FEATURE
<223> OTHER INFORMATION: delta-9 desaturase

<400> SEQUENCE: 34

Met Ser Ala Leu Val Leu Ser Leu Ala Phe Ser Thr Pro Ala Arg Gly
1               5                   10                  15

Gly Gly Glu Ser Arg Phe Ala Glu Gly Lys Ala Leu Arg Arg Arg Leu
                20                  25                  30

Asn Ala Ser Ser Cys Asn Ala Ser Ser Lys Asn Ala Gln Leu Met Cys
            35                  40                  45

Glu Arg Arg Ile Leu Ser Trp Cys Tyr Gly Ile Arg Arg Arg Asn Ser
50                  55                  60

Ala Gly Leu Trp Gly Lys Ala Thr Arg Val Gln Val Ser Ala Val Ala
65                  70                  75                  80

Glu Glu Glu Gly Gly Arg Ile Leu Leu Ser Asp Val Val Lys Lys
                85                  90                  95

Lys Arg Lys Pro Phe Leu Leu Glu Leu Arg Glu Trp Ser Leu Gly Asp
                100                 105                 110

Ile Gly Ala Ala Gly Thr Val Phe Gly Met His Ala Leu Cys Leu Leu
            115                 120                 125

Ala Pro Phe Thr Phe Thr Trp Lys Ala Phe Gly Val Phe Ala Val Leu
        130                 135                 140

Tyr Val Val Thr Gly Leu Leu Gly Ile Thr Leu Ser Tyr His Arg Asn
145                 150                 155                 160

Leu Ser His Arg Ser Phe Arg Leu Pro Lys Trp Leu Glu Tyr Leu Phe
                165                 170                 175

Ala Tyr Cys Gly Val Gln Ala Val Gln Gly Asp Pro Leu Asp Trp Val
            180                 185                 190

Ser Thr His Arg Tyr His His Glu Tyr Cys Asp Ser Val Lys Asp Pro
```

```
                  195                 200                 205
His Ser Pro Asn Glu Gly Phe Trp Tyr Ser His Met Ser Trp Met Phe
    210                 215                 220
Asp Glu Lys Thr Met Phe Asp Arg Val Gly Thr Arg Asn Asn Val Ser
225                 230                 235                 240
Asp Leu Glu Met Gln Pro Phe Tyr Arg Phe Ile Arg Asp Thr Tyr Ile
                245                 250                 255
Ile His Pro Ile Ala Met Gly Leu Leu Tyr Ala Leu Gly Gly Pro
            260                 265                 270
Pro Phe Val Ile Trp Gly Met Ala Val Arg Ile Val Trp Val Tyr His
        275                 280                 285
Ile Thr Trp Leu Val Asn Ser Ala Ala His Val Trp Gly Tyr Gln Ala
    290                 295                 300
Trp Asn Thr Gly Asp Leu Ser Arg Asn Asn Trp Val Ala Ala Leu
305                 310                 315                 320
Ala Phe Gly Glu Gly Trp His Asn Asn His Ala Phe Gln Tyr Ser
                325                 330                 335
Ala Arg His Gly Leu Glu Trp Trp Gln Phe Asp Pro Thr Trp Tyr Val
            340                 345                 350
Ile Lys Ile Leu Glu Ala Leu Gly Leu Ala Lys Asp Val Arg Ala Pro
        355                 360                 365
Leu Glu Gln His Lys Thr Arg Met Ser Ser Lys Pro Gly Leu
    370                 375                 380
```

```
<210> SEQ ID NO 35
<211> LENGTH: 30
<212> TYPE: DNA
<213> ORGANISM: Artificial Sequence
<220> FEATURE:
<223> OTHER INFORMATION: Primer Eg9-5'1

<400> SEQUENCE: 35
catatgagac caccagaatc cttcattgac                                     30

<210> SEQ ID NO 36
<211> LENGTH: 28
<212> TYPE: DNA
<213> ORGANISM: Artificial Sequence
<220> FEATURE:
<223> OTHER INFORMATION: Primer Eg9-5'2

<400> SEQUENCE: 36
gatgatacct gtgagagcac acccattc                                       28

<210> SEQ ID NO 37
<211> LENGTH: 22
<212> TYPE: DNA
<213> ORGANISM: Artificial Sequence
<220> FEATURE:
<223> OTHER INFORMATION: Primer DNR CDS 5'

<400> SEQUENCE: 37
caacgcagag tggccattac gg                                             22

<210> SEQ ID NO 38
<211> LENGTH: 29
<212> TYPE: DNA
<213> ORGANISM: Artificial Sequence
<220> FEATURE:
<223> OTHER INFORMATION: Primer Eg9-3'1

<400> SEQUENCE: 38
```

```
tgggatggtt gcttgaccac caggcaaca                                    29
```

<210> SEQ ID NO 39
<211> LENGTH: 20
<212> TYPE: DNA
<213> ORGANISM: Artificial Sequence
<220> FEATURE:
<223> OTHER INFORMATION: Primer AUAP

<400> SEQUENCE: 39

```
ggccacgcgt cgactagtac                                              20
```

<210> SEQ ID NO 40
<211> LENGTH: 28
<212> TYPE: DNA
<213> ORGANISM: Artificial Sequence
<220> FEATURE:
<223> OTHER INFORMATION: Primer Eg9-3'2

<400> SEQUENCE: 40

```
catcatgaac gacccttct acagcttc                                      28
```

<210> SEQ ID NO 41
<211> LENGTH: 28
<212> TYPE: DNA
<213> ORGANISM: Artificial Sequence
<220> FEATURE:
<223> OTHER INFORMATION: Primer YL837

<400> SEQUENCE: 41

```
gtccatggca gctgttgcag agaaagac                                     28
```

<210> SEQ ID NO 42
<211> LENGTH: 26
<212> TYPE: DNA
<213> ORGANISM: Artificial Sequence
<220> FEATURE:
<223> OTHER INFORMATION: Primer YL838

<400> SEQUENCE: 42

```
tgagcgcagc cgcatgcatg gaaaag                                       26
```

<210> SEQ ID NO 43
<211> LENGTH: 26
<212> TYPE: DNA
<213> ORGANISM: Artificial Sequence
<220> FEATURE:
<223> OTHER INFORMATION: Primer YL839

<400> SEQUENCE: 43

```
cttttccatg catgcggctg cgctca                                       26
```

<210> SEQ ID NO 44
<211> LENGTH: 38
<212> TYPE: DNA
<213> ORGANISM: Artificial Sequence
<220> FEATURE:
<223> OTHER INFORMATION: Primer YL840

<400> SEQUENCE: 44

```
tttgcggccg cttaggcaag gcgcatggca gccttcct                          38
```

<210> SEQ ID NO 45
<211> LENGTH: 6646
<212> TYPE: DNA
<213> ORGANISM: Artificial Sequence
<220> FEATURE:
<223> OTHER INFORMATION: Plasmid pYNTGUS1-NC

<400> SEQUENCE: 45

```
catggatggt acgtcctgta gaaacccaa cccgtgaaat caaaaaactc gacggcctgt      60
gggcattcag tctggatcgc gaaaactgtg gaattgatca gcgttggtgg gaaagcgcgt    120
tacaagaaag ccgggcaatt gctgtgccag gcagttttaa cgatcagttc gccgatgcag    180
atattcgtaa ttatgcgggc aacgtctggt atcagcgcga agtctttata ccgaaaggtt    240
gggcaggcca gcgtatcgtg ctgcgtttcg atgcggtcac tcattacggc aaagtgtggg    300
tcaataatca ggaagtgatg gagcatcagg gcggctatac gccatttgaa gccgatgtca    360
cgccgtatgt tattgccggg aaaagtgtac gtatcaccgt ttgtgtgaac aacgaactga    420
actggcagac tatcccgccg ggaatggtga ttaccgacga aaacggcaag aaaaagcagt    480
cttacttcca tgatttcttt aactatgccg gatccatcg cagcgtaatg ctctacacca    540
cgccgaacac ctgggtggac gatatcaccg tggtgacgca tgtcgcgcaa gactgtaacc    600
acgcgtctgt tgactggcag gtggtggcca atggtgatgt cagcgttgaa ctgcgtgatg    660
cggatcaaca ggtggttgca actggacaag gcactagcgg gactttgcaa gtggtgaatc    720
cgcacctctg gcaaccgggt gaaggttatc tctatgaact gtgcgtcaca gccaaaagcc    780
agacagagtg tgatatctac ccgcttcgcg tcggcatccg gtcagtggca gtgaagggcg    840
aacagttcct gattaaccac aaaccgttct actttactgg ctttggtcgt catgaagatg    900
cggacttacg tggcaaagga ttcgataacg tgctgatggt gcacgaccac gcattaatgg    960
actggattgg ggccaactcc taccgtacct cgcattaccc ttacgctgaa gagatgctcg   1020
actgggcaga tgaacatggc atcgtggtga ttgatgaaac tgctgctgtc ggctttaacc   1080
tctctttagg cattggtttc gaagcgggca acaagccgaa agaactgtac agcgaagagg   1140
cagtcaacgg ggaaactcag caagcgcact acaggcgat taaagagctg atagcgcgtg   1200
acaaaaacca cccaagcgtg gtgatgtgga gtattgccaa cgaaccggat acccgtccgc   1260
aagtgcacgg gaatatttcg ccactggcgg aagcaacgcg taaactcgac ccgacgcgtc   1320
cgatcacctg cgtcaatgta atgttctgcg acgctcacac cgataccatc agcgatctct   1380
ttgatgtgct gtgcctgaac cgttattacg gatggtatgt ccaaagcggc gatttggaaa   1440
cggcagagaa ggtactggaa aaagaacttc tggcctggca ggagaaactg catcagccga   1500
ttatcatcac cgaatacggc gtggatacgt tagccgggct gcactcaatg tacaccgaca   1560
tgtggagtga agagtatcag tgtgcatggc tggatatgta tcaccgcgtc tttgatcgcg   1620
tcagcgccgt cgtcggtgaa caggtatgga atttcgccga ttttgcgacc tcgcaaggca   1680
tattgcgcgt tggcggtaac aagaaaggga tcttcactcg cgaccgcaaa ccgaagtcgg   1740
cggcttttct gctgcaaaaa cgctggactg catgaacttc ggtgaaaaa ccgcagcagg   1800
gaggcaaaca atgattaatt aactagagcg gccgccaccg cggcccgaga ttccggcctc   1860
ttcggccgcc aagcgacccg ggtggacgtc tagaggtacc tagcaattaa cagatagttt   1920
gccggtgata attctcttaa cctcccacac tcctttgaca taacgattta tgtaacgaaa   1980
ctgaaatttg accagatatt gtgtccgcgg tggagctcca gcttttgttc cctttagtga   2040
gggttaattt cgagcttggc gtaatcatgg tcatagctgt ttcctgtgtg aaattgttat   2100
ccgctcacaa ttccacacaa catacgagcc ggaagcataa agtgtaaagc ctggggtgcc   2160
taatgagtga gctaactcac attaattgcg ttgcgctcac tgcccgcttt ccagtcggga   2220
aacctgtcgt gccagctgca ttaatgaatc ggccaacgcg cggggagagg cggtttgcgt   2280
```

```
attgggcgct cttccgcttc ctcgctcact gactcgctgc gctcggtcgt tcggctgcgg   2340
cgagcggtat cagctcactc aaaggcggta atacggttat ccacagaatc aggggataac   2400
gcaggaaaga acatgtgagc aaaaggccag caaaaggcca ggaaccgtaa aaaggccgcg   2460
ttgctggcgt ttttccatag gctccgcccc cctgacgagc atcacaaaaa tcgacgctca   2520
agtcagaggt ggcgaaaccc gacaggacta taaagatacc aggcgtttcc ccctggaagc   2580
tccctcgtgc gctctcctgt tccgaccctg ccgcttaccg gatacctgtc cgcctttctc   2640
ccttcgggaa gcgtggcgct ttctcatagc tcacgctgta ggtatctcag ttcggtgtag   2700
gtcgttcgct ccaagctggg ctgtgtgcac gaaccccccg ttcagcccga ccgctgcgcc   2760
ttatccggta actatcgtct tgagtccaac ccggtaagac acgacttatc gccactggca   2820
gcagccactg gtaacaggat tagcagagcg aggtatgtag gcggtgctac agagttcttg   2880
aagtggtggc ctaactacgg ctacactaga aggacagtat ttggtatctg cgctctgctg   2940
aagccagtta ccttcggaaa aagagttggt agctcttgat ccggcaaaca aaccaccgct   3000
ggtagcggtg gtttttttgt ttgcaagcag cagattacgc gcagaaaaaa aggatctcaa   3060
gaagatcctt tgatcttttc tacggggtct gacgctcagt ggaacgaaaa ctcacgttaa   3120
gggattttgg tcatgagatt atcaaaaagg atcttcacct agatcctttt aaattaaaaa   3180
tgaagtttta aatcaatcta agtatatat gagtaaactt ggtctgacag ttaccaatgc   3240
ttaatcagtg aggcacctat ctcagcgatc tgtctatttc gttcatccat agttgcctga   3300
ctccccgtcg tgtagataac tacgatacgg gagggcttac catctggccc cagtgctgca   3360
atgataccgc gagacccacg ctcaccggct ccagatttat cagcaataaa ccagccagcc   3420
ggaagggccg agcgcagaag tggtcctgca actttatccg cctccatcca gtctattaat   3480
tgttgccggg aagctagagt aagtagttcg ccagttaata gtttgcgcaa cgttgttgcc   3540
attgctacag gcatcgtggt gtcacgctcg tcgtttggta tggcttcatt cagctccggt   3600
tcccaacgat caaggcgagt tacatgatcc cccatgttgt gcaaaaaagc ggttagctcc   3660
ttcggtcctc cgatcgttgt cagaagtaag ttggccgcag tgttatcact catggttatg   3720
gcagcactgc ataattctct tactgtcatg ccatccgtaa gatgcttttc tgtgactggt   3780
gagtactcaa ccaagtcatt ctgagaatag tgtatgcggc gaccgagttg ctcttgcccg   3840
gcgtcaatac gggataatac cgcgccacat agcagaactt taaaagtgct catcattgga   3900
aaacgttctt cggggcgaaa actctcaagg atcttaccgc tgttgagatc cagttcgatg   3960
taacccactc gtgcacccaa ctgatcttca gcatctttta ctttcaccag cgtttctggg   4020
tgagcaaaaa caggaaggca aaatgccgca aaaaagggaa taaggcgac acggaaatgt   4080 tgaatactca tactcttcct ttttcaatat tattgaagca tttatcaggg ttattgtctc   4140
atgagcggat acatatttga atgtatttag aaaaataaac aaataggggt tccgcgcaca   4200
tttccccgaa aagtgccacc tgacgcgccc tgtagcggcg cattaagcgc ggcgggtgtg   4260
gtggttacgc gcagcgtgac cgctacactt gccagcgccc tagcgcccgc tcctttcgct   4320
ttcttccctt cctttctcgc cacgttcgcc ggctttcccc gtcaagctct aaatcggggg   4380
ctccctttag ggttccgatt tagtgcttta cggcacctcg accccaaaaa acttgattag   4440
ggtgatggtt cacgtagtgg gccatcgccc tgatagacgg ttttcgccc tttgacgttg   4500 gagtccacgt tctttaatag tggactcttg ttccaaactg gaacaacact caaccctatc   4560
tcggtctatt cttttgattt ataagggatt ttgccgattt cggcctattg gttaaaaaat   4620
gagctgattt aacaaaaatt taacgcgaat tttaacaaaa tattaacgct tacaatttcc   4680
```

```
attcgccatt caggctgcgc aactgttggg aagggcgatc ggtgcgggcc tcttcgctat   4740
tacgccagct ggcgaaaggg ggatgtgctg caaggcgatt aagttgggta acgccagggt   4800
tttcccagtc acgacgttgt aaaacgacgg ccagtgaatt gtaatacgac tcactatagg   4860
gcgaattggg taccgggccc cccctcgagg tcgatggtgt cgataagctt gatatcgaat   4920
tcgtccttga ggactcgagt gacagtcttt cgccaaagtc gagaggaggc cagcacgttg   4980
gccttgtcaa gagaccacac gggaagaggg gggttgtgct gaagggccag gaaggcggcc   5040
attcgggcaa ttcgctcaac ctcaggaacg gagtaggtct cggtgtcgga agcgacgcca   5100
gatccgtcat cctcctttcg ctctccaaag tagatacctc cgacgagctc tcggacaatg   5160
atgaagtcgg tgccctcaac gtttcggatg ggggagagat cggcgagctt gggcgacagc   5220
agctggcagg gtcgcaggtt ggcgtacagg ttcaggtcct ttcgcagctt gaggagaccc   5280
tgctcgggtc gcacgtcggt tcgtccgtcg ggagtggtcc atacggtgtt ggcagcgcct   5340
ccgacagcac cgagcataat agagtcagcc tttcggcaga gtcgagagt agcgtcggtg   5400 atgggctcgc cctccttctc aatggcagct cctccaatga gtcggtcctc aaacacaaac   5460
tcggtgccga aggcctcagc aacagacttg agcaccttga cggcctcggc aatcacctcg   5520 ggccacaga agtcgccgcc gagaagaaca atcttcttgg agtcagtctt ggtcttctta   5580
gtttcgggtt ccattgtgga tgtgtgtggt tgtatgtgtg atgtggtgtg tggagtgaaa   5640
atctgtggct ggcaaacgct cttgtatata tacgcacttt tgcccgtgct atgtggaaga   5700
ctaaacctcc gaagattgtg actcaggtag tgcggtatcg gctagggacc caaaccttgt   5760
cgatgccgat agcgctatcg aacgtacccc agccggccgg gagtatgtcg gaggggacat   5820
acgagatcgt caagggtttg tggccaactg gtaaataaat gatgtcgaca taagtttgca   5880
aaaagatcgt atcgatagtt ggagcaaggg agaaatgtag agtgtgaaag actcactatg   5940
gtccgggctt atctcgacca atagccaaag tctggagttt ctgagagaaa aaggcaagat   6000
acgtatgtaa caaagcgacg catggtacaa taataccgga ggcatgtatc atagagagtt   6060
agtggttcga tgatggcact ggtgcctggt atgactttat acggctgact acatatttgt   6120
cctcagacat acaattacag tcaagcactt acccttggac atctgtaggt acccccggc    6180 caagacgatc tcagcgtgtc gtatgtcgga ttggcgtagc tccctcgctc gtcaattggc   6240
tcccatctac tttcttctgc ttggctacac ccagcatgtc tgctatggct cgttttcgtg   6300
ccttatctat cctcccagta ttaccaactc taaatgacat gatgtgattg ggtctacact   6360
ttcatatcag agataaggag tagcacagtt gcataaaaag cccaactcta atcagcttct   6420
tcctttcttg taattagtac aaaggtgatt agcgaaatct ggaagcttag ttggccctaa   6480
aaaaatcaaa aaaagcaaaa aacgaaaaac gaaaaaccac agttttgaga acaggaggt    6540 aacgaaggat cgtatatata tatatatata tatacccca cggatcccga gaccggcctt   6600
tgattcttcc ctacaaccaa ccattctcac caccctaatt cacaac                  6646
```

<210> SEQ ID NO 46
<211> LENGTH: 7483
<212> TYPE: DNA
<213> ORGANISM: Artificial Sequence
<220> FEATURE:
<223> OTHER INFORMATION: Plasmid pZP2L7+Ura

<400> SEQUENCE: 46

```
aaacggtagg ttagtgcttg gtatatgagt tgtaggcatg acaatttgga aaggggtgga     60
ctttgggaat attgtgggat ttcaatacct tagtttgtac agggtaattg ttacaaatga    120
```

```
tacaaagaac tgtatttctt ttcatttgtt ttaattggtt gtatatcaag tccgttagac    180
gagctcagtg ccttggcttt tggcactgta tttcatttt agaggtacac tacattcagt    240
gaggtatggt aaggttgagg gcataatgaa ggcaccttgt actgacagtc acagacctct    300
caccgagaat tttatgagat atactcgggt tcattttagg ctcatcgatc aggagagacc    360
gggttggcgg cgtatttgtg tcccaaaaaa cagccccaat tgccccaatt gaccccaaat    420
tgacccagta gcgggcccaa ccccggcgag agccccttc accccacata tcaaacctcc     480
cccggttccc acacttgccg ttaagggcgt agggtactgc agtctggaat ctacgcttgt    540
tcagactttg tactagtttc tttgtctggc catccgggta acccatgccg gacgcaaaat    600
agactactga aaattttttt gctttgtggt tgggacttta gccaagggta taaaagacca    660
ccgtccccga attacctttc ctcttctttt ctctctctcc ttgtcaactc acacccgaaa    720
tcgttaagca tttccttctg agtataagaa tcattcacca tggctgagga taagaccaag    780
gtcgagttcc ctaccctgac tgagctgaag cactctatcc ctaacgcttg ctttgagtcc    840
aacctcggac tctcgctcta ctacactgcc cgagcgatct tcaacgcatc tgcctctgct    900
gctctgctct acgctgcccg atctactccc ttcattgccg ataacgttct gctccacgct    960
ctggtttgcg ccacctacat ctacgtgcag ggtgtcatct tctggggttt ctttaccgtc   1020
ggtcacgact gtggtcactc tgccttctcc cgataccact ccgtcaactt catcattggc   1080
tgcatcatgc actctgccat tctgactccc ttcgagtcct ggcgagtgac ccaccgacac   1140
catcacaaga acactggcaa cattgataag gacgagatct tctaccctca tcggtccgtc   1200
aaggacctcc aggacgtgcg acaatgggtc tacacctcg gaggtgcttg gttgtctac    1260 ctgaaggtcg gatatgctcc tcgaaccatg tcccactttg accctggga ccctctcctg     1320 cttcgacgag cctccgctgt catcgtgtcc ctcggagtct gggctgcctt cttcgctgcc   1380
tacgcctacc tcacatactc gctcggcttt gccgtcatgg gcctctacta ctatgctcct   1440 ctcttgtct ttgcttcgtt cctcgtcatt actaccttct tgcatcacaa cgacgaagct     1500
actccctggt acggtgactc ggagtggacc tacgtcaagg caacctgag ctccgtcgac     1560 cgatcgtacg gagctttcgt ggacaacctg tctcaccaca ttggcaccca ccaggtccat   1620
cacttgttcc ctatcattcc ccactacaag ctcaacgaag ccaccaagca ctttgctgcc   1680
gcttaccctc acctcgtgag acgtaacgac gagcccatca ttactgcctt cttcaagacc   1740
gctcacctct tgtcaacta cggagctgtg cccgagactg ctcagatttt caccctcaaa   1800
gagtctgccg ctgcagccaa ggccaagagc gactaagcgg ccgcaagtgt ggatggggaa   1860
gtgagtgccc ggttctgtgt gcacaattgg caatccaaga tggatggatt caacacaggg   1920
atatagcgag ctacgtggtg gtgcgaggat atagcaacgg atatttatgt ttgacacttg   1980
agaatgtacg atacaagcac tgtccaagta caatactaaa catactgtac atactcatac   2040
tcgtacccgg gcaacggttt cacttgagtg cagtggctag tgctcttact cgtacagtgt   2100
gcaatactgc gtatcatagt ctttgatgta tatcgtattc attcatgtta gttgcgtacg   2160
ggcgtcgttg cttgtgtgat ttttgaggac ccatcccttt ggtatataag tatactctgg   2220
ggttaaggtt gcccgtgtag tctaggttat agttttcatg tgaaataccg agagccgagg   2280
gagaataaac ggggtatt ggacttgttt ttttcgcgga aaagcgtcga atcaaccctg      2340
cgggccttgc accatgtcca cgacgtgttt ctcgccccaa ttcgcccctt gcacgtcaaa   2400
attaggcctc catctagacc cctccataac atgtgactgt ggggaaaagt ataagggaaa   2460
ccatgcaacc atagacgacg tgaaagacgg ggaggaacca atggaggcca aagaaatggg   2520
```

```
gtagcaacag tccaggagac agacaaggag acaaggagag ggcgcccgaa agatcggaaa   2580
aacaaacatg tccaattggg gcagtgacgg aaacgacacg gacacttcag tacaatggac   2640
cgaccatctc caagccaggg ttattccggt atcaccttgg ccgtaacctc ccgctggtac   2700
ctgatattgt acacgttcac attcaatata ctttcagcta caataagaga ggctgtttgt   2760
cgggcatgtg tgtccgtcgt atggggtgat gtccgagggc gaaattcgct acaagcttaa   2820
ctctggcgct tgtccagtat gaatagacaa gtcaagacca gtggtgccat gattgacagg   2880
gaggtacaag acttcgatac tcgagcatta ctccggacttg tggcgattga acagacgggc   2940
gatcgcttct cccccgtatt gccggcgcgc cagctgcatt aatgaatcgg ccaacgcgcg   3000
gggagaggcg gtttgcgtat tgggcgctct tccgcttcct cgctcactga ctcgctgcgc   3060
tcggtcgttc ggctgcggcg agcggtatca gctcactcaa aggcggtaat acggttatcc   3120
acagaatcag gggataacgc aggaaagaac atgtgagcaa aaggccagca aaaggccagg   3180
aaccgtaaaa aggccgcgtt gctggcgttt ttccataggc tccgcccccc tgacgagcat   3240
cacaaaaatc gacgctcaag tcagaggtgg cgaaacccga caggactata aagataccag   3300
gcgtttcccc ctggaagctc cctcgtgcgc tctcctgttc cgaccctgcc gcttaccgga   3360
tacctgtccg cctttctccc ttcgggaagc gtggcgcttt ctcatagctc acgctgtagg   3420
tatctcagtt cggtgtaggt cgttcgctcc aagctgggct gtgtgcacga accccccgtt   3480
cagcccgacc gctgcgcctt atccggtaac tatcgtcttg agtccaaccc ggtaagacac   3540
gacttatcgc cactggcagc agccactggt aacaggatta gcagagcgag gtatgtaggc   3600
ggtgctacag agttcttgaa gtggtggcct aactacggct acactagaag aacagtattt   3660
ggtatctgcg ctctgctgaa gccagttacc ttcggaaaaa gagttggtag ctcttgatcc   3720
ggcaaacaaa ccaccgctgg tagcggtggt ttttttgttt gcaagcagca gattacgcgc   3780
agaaaaaaag gatctcaaga agatcctttg atcttttcta cggggtctga cgctcagtgg   3840
aacgaaaact cacgttaagg gattttggtc atgagattat caaaaaggat cttcacctag   3900
atccttttaa attaaaaatg aagttttaaa tcaatctaaa gtatatatga gtaaacttgg   3960
tctgacagtt accaatgctt aatcagtgag gcacctatct cagcgatctg tctatttcgt   4020
tcatccatag ttgcctgact ccccgtcgtg tagataacta cgatacggga gggcttacca   4080
tctggcccca gtgctgcaat gataccgcga gacccacgct caccggctcc agatttatca   4140
gcaataaacc agccagccgg aagggccgag cgcagaagtg gtcctgcaac tttatccgcc   4200
tccatccagt ctattaattg ttgccgggaa gctagagtaa gtagttcgcc agttaatagt   4260
ttgcgcaacg ttgttgccat tgctacaggc atcgtggtgt cacgctcgtc gtttggtatg   4320
gcttcattca gctccggttc ccaacgatca aggcgagtta catgatcccc catgttgtgc   4380
aaaaaagcgg ttagctcctt cggtcctccg atcgttgtca gaagtaagtt ggccgcagtg   4440
ttatcactca tggttatggc agcactgcat aattctctta ctgtcatgcc atccgtaaga   4500
tgcttttctg tgactggtga gtactcaacc aagtcattct gagaatagtg tatgcggcga   4560
ccgagttgct cttgcccggc gtcaatacgg gataataccg cgccacatag cagaacttta   4620
aaagtgctca tcattggaaa acgttcttcg gggcgaaaac tctcaaggat cttaccgctg   4680
ttgagatcca gttcgatgta acccactcgt gcacccaact gatcttcagc atcttttact   4740
ttcaccagcg tttctgggtg agcaaaaaca ggaaggcaaa atgccgcaaa aaagggaata   4800
agggcgacac ggaaatgttg aatactcata ctcttccttt ttcaatatta ttgaagcatt   4860
tatcagggtt attgtctcat gagcggatac atatttgaat gtatttagaa aaataaacaa   4920
```

```
ataggggttc cgcgcacatt tccccgaaaa gtgccacctg atgcggtgtg aaataccgca    4980
cagatgcgta aggagaaaat accgcatcag gaaattgtaa gcgttaatat tttgttaaaa    5040
ttcgcgttaa attttttgtta aatcagctca ttttttaacc aataggccga aatcggcaaa    5100
atcccttata aatcaaaaga atagaccgag atagggttga gtgttgttcc agtttggaac    5160
aagagtccac tattaaagaa cgtggactcc aacgtcaaag ggcgaaaaac cgtctatcag    5220
ggcgatggcc cactacgtga accatcaccc taatcaagtt ttttgggtgtc gaggtgccgt    5280 aaagcactaa atcggaaccc taaagggagc ccccgattta gagcttgacg gggaaagccg    5340
gcgaacgtgg cgagaaagga agggaagaaa gcgaaaggag cgggcgctag ggcgctggca    5400
agtgtagcgg tcacgctgcg cgtaaccacc acacccgccg cgcttaatgc gccgctacag    5460
ggcgcgtcca ttcgccattc aggctgcgca actgttggga agggcgatcg gtgcgggcct    5520
cttcgctatt acgccagctg gcgaaagggg gatgtgctgc aaggcgatta agttgggtaa    5580
cgccagggtt ttcccagtca cgacgttgta aaacgacggc cagtgaattg taatacgact    5640
cactataggg cgaattgggc ccgacgtcgc atgcgctgat gacactttgg tctgaaagag    5700
atgcattttg aatcccaaac ttgcagtgcc caagtgacat acatctccgc gttttggaaa    5760
atgttcagaa acagttgatt gtgttggaat ggggaatggg gaatggaaaa atgactcaag    5820
tatcaattcc aaaaacttct ctggctggca gtacctactg tccatactac tgcattttct    5880
ccagtcaggc cactctatac tcgacgacac agtagtaaaa cccagataat ttcgacataa    5940
acaagaaaac agacccaata atatttatat atagtcagcc gtttgtccag ttcagactgt    6000
aatagccgaa aaaaaatcca aagtttctat tctaggaaaa tatattccaa tatttttaat    6060
tcttaatctc atttatttta ttctagcgaa atacatttca gctacttgag acatgtgata    6120
cccacaaatc ggattcggac tcggttgttc agaagagcat atggcattcg tgctcgcttg    6180
ttcacgtatt cttcctgttc catctcttgg ccgacaatca cacaaaaatg gggtttttt    6240 tttaattcta atgattcatt acagcaaaat tgagatatag cagaccacgt attccataat    6300
caccaaggaa gttcttgggc gtcttaatta agtcatacac aagtcagctt tcttcgagcc    6360
tcatataagt ataagtagtt caacgtatta gcactgtacc cagcatctcc gtatcgagaa    6420
acacaacaac atgccccatt ggacagatca tgcggataca caggttgtgc agtatcatac    6480
atactcgatc agacaggtcg tctgaccatc atacaagctg aacaagcgct ccatacttgc    6540
acgctctcta tatacacagt taaattacat atccatagtc taacctctaa cagttaatct    6600
tctggtaagc ctcccagcca gccttctggt atcgcttggc ctcctcaata ggatctcggt    6660
tctggccgta cagacctcgg ccgacaatta tgatatccgt tccggtagac atgacatcct    6720
caacagttcg gtactgctgt ccgagagcgt ctcccttgtc gtcaagaccc accccggggg    6780
tcagaataag ccagtcctca gagtcgccct taggtcggtt ctgggcaatg aagccaacca    6840
caaactcggg gtcggatcgg gcaagctcaa tggtctgctt ggagtactcg ccagtggcca    6900
gagagccctt gcaagacagc tcggccagca tgagcagacc tctggccagc ttctcgttgg    6960 gagagggac taggaactcc ttgtactggg agttctcgta gtcagagacg tcctccttct    7020
tctgttcaga gacagtttcc tcggcaccag ctcgcaggcc agcaatgatt ccggttccgg    7080
gtacaccgtg ggcgttggtg atatcggacc actcggcgat tcggtgacac cggtactggt    7140
gcttgacagt gttgccaata tctgcgaact ttctgtcctc gaacaggaag aaaccgtgct    7200
taagagcaag ttccttgagg gggagcacag tgccggcgta ggtgaagtcg tcaatgatgt    7260
cgatatgggt tttgatcatg cacacataag gtccgacctt atcggcaagc tcaatgagct    7320
```

-continued

| | |
|---|---|
| ccttggtggt ggtaacatcc agagaagcac acaggttggt tttcttggct gccacgagct | 7380 |
| tgagcactcg agcggcaaag gcggacttgt ggacgttagc tcgagcttcg taggagggca | 7440 |
| ttttggtggt gaagaggaga ctgaaataaa tttagtctgc aga | 7483 |

<210> SEQ ID NO 47
<211> LENGTH: 8109
<212> TYPE: DNA
<213> ORGANISM: Artificial Sequence
<220> FEATURE:
<223> OTHER INFORMATION: Plasmid pZP2NEg9

<400> SEQUENCE: 47

| | |
|---|---|
| catggcagct gttgcagaga aagacttgga caccgattta aatgtttcaa ccgcgaaaga | 60 |
| agagttgcgc cttccacctt atgccggaaa ggaacccttc cgacctgatg tcttccaacc | 120 |
| acgaagtgaa gtcagggaaa tctttggcac aggcatcaag tacatcaaga agagaaactg | 180 |
| gtggtggcca agaacctaca attcaacaga tattgtcttt atccttgtta ccttttccat | 240 |
| gcatgcggct gcgctcattt tgggccccat gacatacagg cctgattgtt tggctttgtt | 300 |
| tttgggattg tacgtggtca ctggactatt tggtatcacg ctgtcatacc atcgtcagct | 360 |
| gtcgcacagg tccttcacga caccgaaatg gttggaatac atcttcgctt attgtggagt | 420 |
| cttggcattc cagggtgatc tctggaatgg gtgtgctct cacaggtatc atcaccaata | 480 |
| ttgcgagaca gatcgtgatc cccactctgt caatgaagga ttctggtggt ctcatatggg | 540 |
| atggttgctt gaccaccagg caacaaagac acggactgga gaccagacta actccatgga | 600 |
| catcatgaac gacccttcct acagcttcat caggaagacc tatcctttgc atttggcgct | 660 |
| gtttgccctg gccctctatg cctggggtgg cattccgtat ttggtgtggg gcgtggcagt | 720 |
| ccgagtgtgc tgggtctggc acatcacctg gtttgtgaac tctgctgttc acacttgggg | 780 |
| caacaaggtg tacaagacca cccctccaga tgagtctcgc aacaactggt gggtcggcct | 840 |
| ccttgcatgg ggtgagggat ggcacaacaa ccaccacgca ttccagtact ctgctcgcca | 900 |
| cggcttggaa tggtggcaag ttgacatgac gtggggtgtg attcgggttc tgcagttctt | 960 |
| ggggctggcc accaatgtca agctgccttc tgaggaaagg aaggctgcca tgcgccttgc | 1020 |
| ctaagcggcc gcaagtgtgg atggggaagt gagtgcccgg ttctgtgtgc acaattggca | 1080 |
| atccaagatg gatggattca acacagggat atagcgagct acgtggtggt gcgaggatat | 1140 |
| agcaacggat atttatgttt gacacttgag aatgtacgat acaagcactg tccaagtaca | 1200 |
| atactaaaca tactgtacat actcatactc gtacccgggc aacggttca cttgagtgca | 1260 |
| gtggctagtg ctcttactcg tacagtgtgc aatactgcgt atcatagtct ttgatgtata | 1320 |
| tcgtattcat tcatgttagt tgcgtacggg cgtcgttgct tgtgtgattt ttgaggaccc | 1380 |
| atccctttgg tatataagta tactctgggg ttaaggttgc ccgtgtagtc taggttatag | 1440 |
| ttttcatgtg aaataccgag agccgaggga gaataaacgg gggtatttgg acttgttttt | 1500 |
| ttcgcgaaa agcgtcgaat caaccctgcg ggccttgcac catgtccacg acgtgtttct | 1560 |
| cgccccaatt cgcccttgc acgtcaaaat taggcctcca tctagacccc tccataacat | 1620 |
| gtgactgtgg ggaaaagtat aagggaaacc atgcaaccat agacgacgtg aaagacgggg | 1680 |
| aggaaccaat ggaggccaaa gaatggggt agcaacagtc caggagacag acaaggagac | 1740 |
| aaggagaggg cgcccgaaag atcggaaaaa caaacatgtc caattggggc agtgacggaa | 1800 |
| acgacacgga cacttcagta caatggaccg accatctcca agccagggtt attccggtat | 1860 |
| caccttggcc gtaacctccc gctggtacct gatattgtac acgttcacat tcaatatact | 1920 |

```
ttcagctaca ataagagagg ctgtttgtcg ggcatgtgtg tccgtcgtat ggggtgatgt   1980
ccgagggcga aattcgctac aagcttaact ctggcgcttg tccagtatga atagacaagt   2040
caagaccagt ggtgccatga ttgacaggga ggtacaagac ttcgatactc gagcattact   2100
cggacttgtg gcgattgaac agacgggcga tcgcttctcc cccgtattgc cggcgcgcca   2160
gctgcattaa tgaatcggcc aacgcgcggg gagaggcggt ttgcgtattg ggcgctcttc   2220
cgcttcctcg ctcactgact cgctgcgctc ggtcgttcgg ctgcggcgag cggtatcagc   2280
tcactcaaag gcggtaatac ggttatccac agaatcaggg gataacgcag aaagaacat    2340
gtgagcaaaa ggccagcaaa aggccaggaa ccgtaaaaag gccgcgttgc tggcgttttt   2400
ccataggctc cgcccccctg acgagcatca aaaaatcga cgctcaagtc agaggtggcg    2460
aaacccgaca ggactataaa gataccaggc gtttccccct ggaagctccc tcgtgcgctc   2520
tcctgttccg accctgccgc ttaccggata cctgtccgcc tttctccctt cgggaagcgt   2580
ggcgctttct catagctcac gctgtaggta tctcagttcg gtgtaggtcg ttcgctccaa   2640
gctgggctgt gtgcacgaac ccccgttca gcccgaccgc tgcgccttat ccggtaacta   2700
tcgtcttgag tccaacccgg taagacacga cttatcgcca ctggcagcag ccactggtaa   2760
caggattagc agagcgaggt atgtaggcgg tgctacagag ttcttgaagt ggtggcctaa   2820
ctacggctac actagaagaa cagtatttgg tatctgcgct ctgctgaagc cagttacctt   2880
cggaaaaaga gttggtagct cttgatccgg caaacaaacc accgctggta gcggtggttt   2940
ttttgtttgc aagcagcaga ttacgcgcag aaaaaaagga tctcaagaag atcctttgat   3000
cttttctacg gggtctgacg ctcagtggaa cgaaaactca cgttaaggga ttttggtcat   3060
gagattatca aaaaggatct tcacctagat ccttttaaat taaaaatgaa gttttaaatc   3120
aatctaaagt atatatgagt aaacttggtc tgacagttac caatgcttaa tcagtgaggc   3180
acctatctca gcgatctgtc tatttcgttc atccatagtt gcctgactcc ccgtcgtgta   3240
gataactacg atacgggagg gcttaccatc tggccccagt gctgcaatga taccgcgaga   3300
cccacgctca ccggctccag atttatcagc aataaaccag ccagccggaa gggccgagcg   3360
cagaagtggt cctgcaactt tatccgcctc catccagtct attaattgtt gccgggaagc   3420
tagagtaagt agttcgccag ttaatagttt gcgcaacgtt gttgccattg ctacaggcat   3480
cgtggtgtca cgctcgtcgt ttggtatggc ttcattcagc tccggttccc aacgatcaag   3540
gcgagttaca tgatccccca tgttgtgcaa aaaagcggtt agctccttcg gtcctccgat   3600
cgttgtcaga agtaagttgg ccgcagtgtt atcactcatg gttatggcag cactgcataa   3660
ttctcttact gtcatgccat ccgtaagatg cttttctgtg actggtgagt actcaaccaa   3720
gtcattctga gaatagtgta tgcggcgacc gagttgctct tgcccggcgt caatacggga   3780
taataccgcg ccacatagca gaactttaaa agtgctcatc attggaaaac gttcttcggg   3840
gcgaaaactc tcaaggatct taccgctgtt gagatccagt tcgatgtaac ccactcgtgc   3900
acccaactga tcttcagcat cttttacttt caccagcgtt tctgggtgag caaaaacagg   3960
aaggcaaaat gccgcaaaaa agggaataag ggcgacacgg aaatgttgaa tactcatact   4020
cttcctttt caatattatt gaagcattta tcagggttat tgtctcatga gcggatacat   4080
atttgaatgt atttagaaaa ataaacaaat aggggttccg cgcacatttc cccgaaaagt   4140
gccacctgat gcggtgtgaa ataccgcaca gatgcgtaag gagaaaatac cgcatcagga   4200
aattgtaagc gttaatattt tgttaaaatt cgcgttaaat ttttgttaaa tcagctcatt   4260
ttttaaccaa taggccgaaa tcggcaaaat cccttataaa tcaaaagaat agaccgagat   4320
```

```
agggttgagt gttgttccag tttggaacaa gagtccacta ttaaagaacg tggactccaa    4380
cgtcaaaggg cgaaaaaccg tctatcaggg cgatggccca ctacgtgaac catcaccta     4440 atcaagtttt ttggggtcga ggtgccgtaa agcactaaat cggaaccta aagggagccc     4500 ccgatttaga gcttgacggg gaaagccggc gaacgtggcg agaaaggaag ggaagaaagc    4560
gaaaggagcg ggcgctaggg cgctggcaag tgtagcggtc acgctgcgcg taaccaccac    4620
acccgccgcg cttaatgcgc cgctacaggg cgcgtccatt cgccattcag gctgcgcaac    4680
tgttgggaag ggcgatcggt gcgggcctct tcgctattac gccagctggc gaaaggggga    4740
tgtgctgcaa ggcgattaag ttgggtaacg ccagggtttt cccagtcacg acgttgtaaa    4800
acgacggcca gtgaattgta atacgactca ctatagggcg aattgggccc gacgtcgcat    4860
gcgctgatga cactttggtc tgaaagagat gcattttgaa tcccaaactt gcagtgccca    4920
agtgacatac atctccgcgt tttggaaaat gttcagaaac agttgattgt gttggaatgg    4980
ggaatgggga atggaaaaat gactcaagta tcaattccaa aaacttctct ggctggcagt    5040
acctactgtc catactactg cattttctcc agtcaggcca ctctatactc gacgacacag    5100
tagtaaaacc cagataattt cgacataaac aagaaaacag acccaataat atttatatat    5160
agtcagccgt ttgtccagtt cagactgtaa tagccgaaaa aaaatccaaa gtttctattc    5220
taggaaaata tattccaata tttttaattc ttaatctcat ttattttatt ctagcgaaat    5280
acatttcagc tacttgagac atgtgatacc cacaaatcgg attcggactc ggttgttcag    5340
aagagcatat ggcattcgtg ctcgcttgtt cacgtattct tcctgttcca tctcttggcc    5400
gacaatcaca caaaaatggg gttttttttt taattctaat gattcattac agcaaaattg    5460
agatatagca gaccacgtat tccataatca ccaaggaagt tcttgggcgt cttaattaag    5520
tcatacacaa gtcagctttc ttcgagcctc atataagtat aagtagttca acgtattagc    5580
actgtaccca gcatctccgt atcgagaaac acaacaacat gccccattgg acagatcatg    5640
cggatacaca ggttgtgcag tatcatacat actcgatcag acaggtcgtc tgaccatcat    5700
acaagctgaa caagcgctcc atacttgcac gctctctata tacacagtta aattacatat    5760
ccatagtcta acctctaaca gttaatcttc tggtaagcct cccagccagc cttctggtat    5820
cgcttggcct cctcaatagg atctcggttc tggccgtaca gacctcggcc gacaattatg    5880
atatccgttc cggtagacat gacatcctca acagttcggt actgctgtcc gagagcgtct    5940
cccttgtcgt caagacccac cccggggtc agaataagcc agtcctcaga gtcgcccta     6000 ggtcggttct gggcaatgaa gccaaccaca aactcggggt cggatcgggc aagctcaatg    6060
gtctgcttgg agtactcgcc agtggccaga gagcccttgc aagacagctc ggccagcatg    6120
agcagacctc tggccagctt ctcgttggga gagggacta ggaactcctt gtactgggag     6180
ttctcgtagt cagagacgtc ctccttcttc tgttcagaga cagtttcctc ggcaccagct    6240
cgcaggccag caatgattcc ggttccgggt acaccgtggg cgttggtgat atcggaccac    6300
tcggcgattc ggtgacaccg gtactggtgc ttgacagtgt tgccaatatc tgcgaacttt    6360
ctgtcctcga acaggaagaa accgtgctta agagcaagtt ccttgagggg gagcacagtg    6420
ccggcgtagg tgaagtcgtc aatgatgtcg atatgggttt tgatcatgca cacataaggt    6480
ccgaccttat cggcaagctc aatgagctcc ttggtggtgg taacatccag agaagcacac    6540
aggttggttt tcttggctgc cacgagcttg agcactcgag cggcaaaggc ggacttgtgg    6600
acgttagctc gagcttcgta ggagggcatt ttggtggtga agaggagact gaaataaatt    6660
tagtctgcag aacttttat cggaacccta tctggggcag tgaagtatat gttatggtaa     6720
```

-continued

```
tagttacgag ttagttgaac ttatagatag actggactat acggctatcg gtccaaatta    6780
gaaagaacgt caatggctct ctgggcgtcg cctttgccga caaaaatgtg atcatgatga    6840
aagccagcaa tgacgttgca gctgatattg ttgtcggcca accgcgccga aaacgcagct    6900
gtcagaccca cagcctccaa cgaagaatgt atcgtcaaag tgatccaagc acactcatag    6960
ttggagtcgt actccaaagg cggcaatgac gagtcagaca gatactcgtc aaacggtagg    7020
ttagtgcttg gtatatgagt tgtaggcatg acaatttgga aaggggtgga ctttgggaat    7080
attgtgggat ttcaatacct tagttttgtac agggtaattg ttacaaatga tacaaagaac    7140
tgtatttctt ttcatttgtt ttaattggtt gtatatcaag tccgttagac gagctcagtg    7200
ccttggcttt tggcactgta tttcattttt agaggtacac tacattcagt gaggtatggt    7260
aaggttgagg gcataatgaa ggcaccttgt actgacagtc acagacctct caccgagaat    7320
tttatgagat atactcgggt tcattttagg ctcatcgata gttggagcaa gggagaaatg    7380
tagagtgtga aagactcact atggtccggg cttatctcga ccaatagcca aagtctggag    7440
tttctgagag aaaaaggcaa gatacgtatg taacaaagcg acgcatggta caataatacc    7500
ggaggcatgt atcatagaga gttagtggtt cgatgatggc actggtgcct ggtatgactt    7560
tatacggctg actacatatt tgtcctcaga catacaatta cagtcaagca cttacccttg    7620
gacatctgta ggtaccccc ggccaagacg atctcagcgt gtcgtatgtc ggattggcgt    7680
agctccctcg ctcgtcaatt ggctcccatc tactttcttc tgcttggcta cacccagcat    7740
gtctgctatg gctcgttttc gtgccttatc tatcctccca gtattaccaa ctctaaatga    7800
catgatgtga ttgggtctac actttcatat cagagataag gagtagcaca gttgcataaa    7860
aagcccaact ctaatcagct tcttcctttc ttgtaattag tacaaaggtg attagcgaaa    7920
tctggaagct tagttggccc taaaaaaatc aaaaaaagca aaaacgaaa aacgaaaaac    7980 cacagttttg agaacaggga ggtaacgaag gatcgtatat atatatatat atatatatac    8040
ccacggatcc cgagaccggc ctttgattct tccctacaac caaccattct caccacccta    8100
attcacaac                                                            8109
```

<210> SEQ ID NO 48
<211> LENGTH: 19
<212> TYPE: DNA
<213> ORGANISM: Artificial Sequence
<220> FEATURE:
<223> OTHER INFORMATION: Primer T7

<400> SEQUENCE: 48
ggaaacagct atgaccatg                                                   19

<210> SEQ ID NO 49
<211> LENGTH: 459
<212> TYPE: PRT
<213> ORGANISM: Rhizopus stolonifer (GenBank Accession No. AAX22052)

<400> SEQUENCE: 49

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

```
Ser Asp Val Phe His Ala Met His Pro Glu Ser Ala Tyr Glu Val Leu
 65                  70                  75                  80

Asn Asn Tyr Phe Val Gly Asp Val Gln Glu Thr Val Thr Glu Lys
                 85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Leu Leu
130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
                180                 185                 190

Val Phe Leu Gly Asn Phe Cys Gln Gly Phe Ser Leu Ser Trp Trp Lys
            195                 200                 205

Asn Lys His Asn Thr His His Ala Ser Thr Asn Val His Gly Gln Asp
        210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
                260                 265                 270

Ile Leu Ala Phe Ala Arg Leu Ser Trp Ala Leu Gln Ser Leu Ser Tyr
                275                 280                 285

Ser Phe Lys Lys Glu Ser Ile Asn Lys Ser Arg Gln Leu Asn Leu Phe
            290                 295                 300

Glu Arg Val Cys Ile Val Gly His Trp Ala Leu Phe Ala Phe Cys Ile
305                 310                 315                 320

Tyr Ser Trp Cys Ser Asn Val Tyr His Met Val Leu Phe Phe Leu Val
                325                 330                 335

Ser Gln Ala Thr Thr Gly Tyr Thr Leu Ala Leu Val Phe Ala Leu Asn
                340                 345                 350

His Asn Gly Met Pro Val Ile Thr Glu Glu Lys Ala Glu Ser Met Glu
                355                 360                 365

Phe Phe Glu Ile Gln Val Ile Thr Gly Arg Asp Val Thr Leu Ser Pro
370                 375                 380

Leu Gly Asp Trp Phe Met Gly Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
            420                 425                 430

Phe Leu Lys Gly Thr Leu Glu Val Leu Gln Thr Leu Asp Ile Thr Ser
        435                 440                 445

Lys Leu Ser Leu Gln Leu Ser Lys Lys Ser Phe
450                 455

<210> SEQ ID NO 50
<211> LENGTH: 695
<212> TYPE: DNA
```

<213> ORGANISM: Pavlova lutheri

<400> SEQUENCE: 50

| | | | | | |
|---|---|---|---|---|---|
| agggccaagg | gtgccaacca | ccttccacgt | gagactacac | accgtaggcc | gatgggcaag | 60
| ggtggagacg | gcggcgcgca | ggcggtgagc | gggaccgacg | cgtctctcgc | tgaggtgagc | 120
| tccgtcgata | gcaagagcgt | gcacgtcgtg | ctctacggca | agcgcgtgga | tgtcacaaag | 180
| ttccagggct | acgacgtggc | ctggtggcgc | gcgcgccata | acacgcacca | cgtgtgcacc | 240
| aacgaggatg | gttcggaccc | ggacatcaag | acggcgcccc | tgctcatcta | cgtgcgagag | 300
| aacccgtcca | ttgccaagcg | gctcaacttc | ttccagcgct | ggcagcagta | ctactatgtg | 360
| ccgaccatgg | ccatcctcga | cctctactgg | cgcctggagt | ccatcgcgta | cgtggctgtg | 420
| cgcctgccta | agatgtggat | gcaggccgcc | gctcttgccg | ctcactacgc | gctcctgtgc | 480
| tgggtcttcg | cagcgcatct | caacctcatc | cctctcatga | tggttgcacg | cggcttcgcg | 540
| acgggcatct | tgtctttgc | aacccactat | ggtgaggaca | tcctcgaccg | cgagcacgtc | 600
| gagggcatga | cgctcgtcga | gcagaccgcc | aagacctccc | gtaacatcac | gggcggctgg | 660
| ctagtgaacg | tgctcacggg | cttcatctcc | ctgca | | | 695

<210> SEQ ID NO 51
<211> LENGTH: 1106
<212> TYPE: DNA
<213> ORGANISM: Pavlova lutheri

<400> SEQUENCE: 51

| | | | | | |
|---|---|---|---|---|---|
| agggccaagg | gtgccaacca | ccttccacgt | gagactacac | accgtaggcc | gatgggcaag | 60
| ggtggagacg | gcggcgcgca | ggcggtgagc | gggaccgacg | cgtctctcgc | tgaggtgagc | 120
| tccgtcgata | gcaagagcgt | gcacgtcgtg | ctctacggca | agcgcgtgga | tgtcacaaag | 180
| ttccagggct | acgacgtggc | ctggtggcgc | gcgcgccata | acacgcacca | cgtgtgcacc | 240
| aacgaggatg | gttcggaccc | ggacatcaag | acggcgcccc | tgctcatcta | cgtgcgagag | 300
| aacccgtcca | ttgccaagcg | gctcaacttc | ttccagcgct | ggcagcagta | ctactatgtg | 360
| ccgaccatgg | ccatcctcga | cctctactgg | cgcctggagt | ccatcgcgta | cgtggctgtg | 420
| cgcctgccta | agatgtggat | gcaggccgcc | gctcttgccg | ctcactacgc | gctcctgtgc | 480
| tgggtcttcg | cagcgcatct | caacctcatc | cctctcatga | tggttgcacg | cggcttcgcg | 540
| acgggcatcg | ttgtctttgc | aacccactat | ggtgaggaca | tcctcgaccg | cgagcacgtc | 600
| gagggcatga | cgctcgtcga | gcagaccgcc | aagacctccc | gtaacatcac | gggcggctgg | 660
| ctagtgaacg | tgctcacggg | cttcatctcc | ctgcagaccg | agcatcacct | cttccccatg | 720
| atgcccaccg | gcaacctaat | gactatccag | cccgaggtac | gcgacttctt | caagaagcat | 780
| ggcctcgagt | accgcgaggg | caacctcttc | cagtgcgtgc | accagaacat | caaggctctc | 840
| gccttcgagc | acctcctcca | ctgagcgtca | ccactcaagc | gtcctaagtg | cacaggtact | 900
| gtcttctgac | cgatggccgc | gcggctccct | cggctggcag | tggggccaac | gagtggcctc | 960
| gcgggatcgg | gcacgatcgg | gcctccatga | aacttcagtg | ttcagagaca | agccgacaac | 1020
| ctccgcatcg | tgagaaatct | tttaaagcag | tatgttccat | cacgccgctt | ttgcagtcaa | 1080
| taacattacc | caaaaaaaaa | aaaaaa | | | | 1106

<210> SEQ ID NO 52
<211> LENGTH: 287
<212> TYPE: PRT
<213> ORGANISM: Pavlova lutheri

<400> SEQUENCE: 52

| | | | | | | | | | | | | | | |
|---|---|---|---|---|---|---|---|---|---|---|---|---|---|---|
|Arg|Ala|Lys|Gly|Ala|Asn|His|Leu|Pro|Arg|Glu|Thr|Thr|His|Arg|Arg
1| | | |5| | | | |10| | | | |15| |

Pro Met Gly Lys Gly Gly Asp Gly Gly Ala Gln Ala Val Ser Gly Thr
              20              25              30

Asp Ala Ser Leu Ala Glu Val Ser Ser Val Asp Ser Lys Ser Val His
        35              40              45

Val Val Leu Tyr Gly Lys Arg Val Asp Val Thr Lys Phe Gln Gly Tyr
50              55              60

Asp Val Ala Trp Trp Arg Ala Arg His Asn Thr His His Val Cys Thr
65              70              75              80

Asn Glu Asp Gly Ser Asp Pro Asp Ile Lys Thr Ala Pro Leu Leu Ile
              85              90              95

Tyr Val Arg Glu Asn Pro Ser Ile Ala Lys Arg Leu Asn Phe Phe Gln
        100             105            110

Arg Trp Gln Gln Tyr Tyr Tyr Val Pro Thr Met Ala Ile Leu Asp Leu
        115             120            125

Tyr Trp Arg Leu Glu Ser Ile Ala Tyr Val Ala Val Arg Leu Pro Lys
        130             135            140

Met Trp Met Gln Ala Ala Leu Ala Ala His Tyr Ala Leu Leu Cys
145              150              155            160

Trp Val Phe Ala Ala His Leu Asn Leu Ile Pro Leu Met Met Val Ala
              165             170            175

Arg Gly Phe Ala Thr Gly Ile Val Val Phe Ala Thr His Tyr Gly Glu
        180             185            190

Asp Ile Leu Asp Arg Glu His Val Glu Gly Met Thr Leu Val Glu Gln
        195             200            205

Thr Ala Lys Thr Ser Arg Asn Ile Thr Gly Gly Trp Leu Val Asn Val
    210             215            220

Leu Thr Gly Phe Ile Ser Leu Gln Thr Glu His His Leu Phe Pro Met
225              230              235            240

Met Pro Thr Gly Asn Leu Met Thr Ile Gln Pro Glu Val Arg Asp Phe
              245             250            255

Phe Lys Lys His Gly Leu Glu Tyr Arg Glu Gly Asn Leu Phe Gln Cys
        260             265            270

Val His Gln Asn Ile Lys Ala Leu Ala Phe Glu His Leu Leu His
            275             280            285

<210> SEQ ID NO 53
<211> LENGTH: 20
<212> TYPE: DNA
<213> ORGANISM: Artificial Sequence
<220> FEATURE:
<223> OTHER INFORMATION: Primer SeqE

<400> SEQUENCE: 53
cgacacactc caatctttcc                               20

<210> SEQ ID NO 54
<211> LENGTH: 20
<212> TYPE: DNA
<213> ORGANISM: Artificial Sequence
<220> FEATURE:
<223> OTHER INFORMATION: Primer SeqW

<400> SEQUENCE: 54
ggtggctgga gttagacatc                               20

```
<210> SEQ ID NO 55
<211> LENGTH: 22
<212> TYPE: DNA
<213> ORGANISM: Artificial Sequence
<220> FEATURE:
<223> OTHER INFORMATION: Primer AP1

<400> SEQUENCE: 55
gtaatacgac tcactatagg gc                                              22

<210> SEQ ID NO 56
<211> LENGTH: 20
<212> TYPE: DNA
<213> ORGANISM: Artificial Sequence
<220> FEATURE:
<223> OTHER INFORMATION: Primer GSP PvDES

<400> SEQUENCE: 56
ctgcgaagac ccagcacagg                                                 20

<210> SEQ ID NO 57
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 57
gtaatacgac tcactatagg gc                                              22

<210> SEQ ID NO 58
<211> LENGTH: 21
<212> TYPE: DNA
<213> ORGANISM: Artificial Sequence
<220> FEATURE:
<223> OTHER INFORMATION: Primer PavDes seq

<400> SEQUENCE: 58
ttgtggcgct caatcatctc c                                               21

<210> SEQ ID NO 59
<211> LENGTH: 1294
<212> TYPE: DNA
<213> ORGANISM: Pavlova lutheri

<400> SEQUENCE: 59
ctttgcgagc gcggcgcaga cgattgcggc ccgtagtgat cgcggtgcgc attgctgtgt     60
ttctagtttt gctgacgccc ggcccgataa tgacaccttc tcccgtttga aatactaata    120
agtaactata ttataatatt caaaggtggc gactatggat ctccttttct aaagttcagc    180
ggaattggga atcggagaaa tttcgagata tgtcataatc acgtgctcta tctcgaatga    240
accgcggccg gtgagcgatt actcgggaag ccaattccta ttaacgagtc agggggatc     300 tttgaggtga gtcggccacg cagagagagc aaggaatcat cctcatccgc cgttctcgag    360
aaagagccaa gggtgccaac caccttccac gtgagactac acaccgtagg ccgatgggca    420
agggtggaga cggcggcgcg caggcggcga gcgggaccga cgcatctctc gctgaggtga    480
gctccgtcga tagcaagagc gtgcgcgtcg tgctctacgg caagcgcgtg gatgtcacaa    540
agttccagag ggcacacccg gcgggagca aggtgttccg catcttccag gagcgcgacg    600
cgacggagca gttcgagtct taccactcgc ccaaggccat caagatgatg gagggcatgc    660
tcaagaagtc ggaggatgcg cccgcttccg tgcccctgcc ctcgcggtcc accatgggca    720
```

```
cggagttcaa ggagatgatt gagcgccaca agagggctgg tctctacgac ccttgcccgt      780
tggacgagct gttcaagctc accatcgtcc ttgcgcccat cttcgtgggc gcctatctcg      840
tgcggagcgg cgtctcgccc ctcgcgggcg cgctctccat gggctttggc ttctacctcg      900
acggctggct tgctcacrac tacctgcatc acgcagtctt caagggctcg gtcaacacgc      960
tcgtcaaggc gaacaacgcc atgggatacg ccctcggctt cctccagggc tacgacgtgg     1020
cctggtggcg cgcgcgccat aacacgcacc acgtgtgcac caacgaggat ggttcggacc     1080
cggacatcaa gacggcgccc ctgctcatct acgtgcgaga gaacccgtcc attgccaagc     1140
ggctcaactt cttccagcgc tggcagcagt actactatgt gccgaccatg gccatcctcg     1200
acctctactg gcgcctggag tccatcgcgt acgtggctgt gcgcctgcct aagatgtgga     1260
tgcaggccgc cgctcttgcc gctcactacg cgct                                 1294

<210> SEQ ID NO 60
<211> LENGTH: 1927
<212> TYPE: DNA
<213> ORGANISM: Pavlova lutheri

<400> SEQUENCE: 60
ctttgcgagc gcggcgcaga cgattgcggc ccgtagtgat cgcggtgcgc attgctgtgt       60
ttctagtttt gctgacgccc ggcccgataa tgacaccttc tcccgtttga aatactaata      120
agtaactata ttataatatt caaaggtggc gactatggat ctccttttct aaagttcagc      180
ggaattggga atcggagaaa tttcgagata tgtcataatc acgtgctcta tctcgaatga      240
accgcggccg gtgagcgatt actcgggaag ccaattccta ttaacgagtc aggggggatc      300
tttgaggtga gtcggccacg cagagagagc aaggaatcat cctcatccgc cgttctcgag      360
aaagagccaa gggtgccaac caccttccac gtgagactac acaccgtagg ccgatgggca      420
agggtggaga cggcggcgcg caggcggtga gcgggaccga cgcgtctctc gctgaggtga      480
gctccgtcga tagcaagagc gtgcacgtcg tgctctacgg caagcgcgtg gatgtcacaa      540
agttccagaa ggcacacccg ggcgggagca aggtgttccg catcttccag gagcgcgacg      600
cgacggagca gttcgagtct taccactcgc ccaaggccat caagatgatg gagggcatgc      660
tcaagaagtc ggaggatgcg cccgcttccg tgcccctgcc ctcgcggtcc accatgggca      720
cggagttcaa ggagatgatt gagcgccaca agagggctgg tctctacgac ccttgcccgt      780
tggacgagct gttcaagctc accatcgtcc ttgcgcccat cttcgtgggc gcctatctcg      840
tgcggagcgg cgtctcgccc ctcgcgggcg cgctctccat gggctttggc ttctacctcg      900
acggctggct tgctcacgac tacctgcatc acgcagtctt caagggctcg gtcaacacgc      960
tcgtcaaggc gaacaacgcc atgggatacg ccctcggctt cctccagggc tacgacgtgg     1020
cctggtggcg cgcgcgccat aacacgcacc acgtgtgcac caacgaggat ggttcggacc     1080
cggacatcaa gacggcgccc ctgctcatct acgtgcgaga gaacccgtcc attgccaagc     1140
ggctcaactt cttccagcgc tggcagcagt actactatgt gccgaccatg gccatcctcg     1200
acctctactg gcgcctggag tccatcgcgt acgtggctgt gcgcctgcct aagatgtgga     1260
tgcaggccgc cgctcttgcc gctcactacg cgctcctgtg ctgggtcttc gcagcgcatc     1320
tcaacctcat ccctctcatg atggttgcac gcggcttcgc gacgggcatc gttgtctttg     1380
caacccacta tggtgaggac atcctcgacc gcgagcacgt cgagggcatg acgctcgtcg     1440
agcagaccgc caagacctcc cgtaacatca cgggcggctg gctagtgaac gtgctcacgg     1500
gcttcatctc cctgcagacc gagcatcacc tcttccccat gatgcccacc ggcaacctaa     1560
```

-continued

```
tgactatcca gcccgaggta cgcgacttct tcaagaagca tggcctcgag taccgcgagg   1620
gcaacctctt ccagtgcgtg caccagaaca tcaaggctct cgccttcgag cacctcctcc   1680
actgagcgtc accactcaag cgtcctaagt gcacaggtac tgtcttctga ccgatggccg   1740
cgcggctccc tcggctggca gtggggccaa cgagtggcct cgcgggatcg ggcacgatcg   1800
ggcctccatg aaacttcagt gttcagagac aagccgacaa cctccgcatc gtgagaaatc   1860
ttttaaagca gtatgttcca tcacgccgct tttgcagtca ataacattac ccaaaaaaaa   1920
aaaaaaa                                                             1927

<210> SEQ ID NO 61
<211> LENGTH: 459
<212> TYPE: PRT
<213> ORGANISM: Rhizopus stolonifer (GenBank Accession No. ABB96724)

<400> SEQUENCE: 61

Met Ser Thr Leu Asp Arg Gln Ser Ile Phe Thr Ile Lys Glu Leu Glu
1               5                   10                  15

Ser Ile Ser Gln Arg Ile His Asp Gly Asp Glu Glu Ala Met Lys Phe
            20                  25                  30

Ile Ile Ile Asp Lys Lys Val Tyr Asp Val Thr Glu Phe Ile Glu Asp
        35                  40                  45

His Pro Gly Gly Ala Gln Val Leu Leu Thr His Val Gly Lys Asp Ala
    50                  55                  60

Ser Asp Val Phe His Ala Met His Pro Glu Ser Ala Tyr Glu Val Leu
65                  70                  75                  80

Asn Asn Tyr Phe Val Gly Asp Val Gln Glu Thr Val Val Thr Glu Lys
                85                  90                  95

Ser Ser Ser Ala Gln Phe Ala Val Glu Met Arg Gln Leu Arg Asp Gln
            100                 105                 110

Leu Lys Lys Glu Gly Tyr Phe His Ser Ser Lys Leu Phe Tyr Ala Tyr
        115                 120                 125

Lys Val Leu Ser Thr Leu Ala Ile Cys Ile Ala Gly Leu Ser Pro Leu
    130                 135                 140

Tyr Ala Tyr Gly Arg Thr Ser Thr Leu Ala Val Val Ala Ser Ala Ile
145                 150                 155                 160

Thr Val Gly Ile Phe Trp Gln Gln Cys Gly Trp Leu Ala His Asp Phe
                165                 170                 175

Gly His His Gln Cys Phe Glu Asp Arg Thr Trp Asn Asp Val Leu Val
            180                 185                 190

Val Phe Leu Gly Asn Phe Cys Gln Gly Phe Ser Leu Ser Trp Trp Lys
        195                 200                 205

Asn Lys His Asn Thr His His Ala Ser Thr Asn Val His Gly Gln Asp
    210                 215                 220

Pro Asp Ile Asp Thr Ala Pro Val Leu Leu Trp Asp Glu Tyr Ala Ser
225                 230                 235                 240

Ala Ala Tyr Tyr Ala Ser Leu Asp Gln Glu Pro Thr Met Val Ser Arg
                245                 250                 255

Phe Leu Ala Glu Gln Val Leu Pro His Gln Thr Arg Tyr Phe Phe Phe
            260                 265                 270

Ile Leu Ala Phe Ala Arg Leu Ser Trp Ala Leu Gln Ser Leu Ser Tyr
        275                 280                 285

Ser Phe Lys Lys Glu Ser Ile Asn Lys Ser Arg Gln Leu Asn Leu Phe
    290                 295                 300

Glu Arg Val Cys Ile Val Gly His Trp Ala Leu Ser Ala Phe Cys Ile
```

```
              305                 310                 315                 320
Tyr Ser Trp Cys Ser Asn Val Tyr His Met Val Leu Phe Phe Leu Val
                    325                 330                 335

Ser Gln Ala Thr Thr Gly Tyr Thr Leu Ala Leu Val Phe Ala Leu Asn
                340                 345                 350

His Asn Gly Met Pro Val Ile Thr Glu Glu Lys Ala Glu Ser Met Glu
                355                 360                 365

Phe Phe Glu Ile Gln Val Ile Thr Gly Arg Asp Val Thr Leu Ser Pro
370                 375                 380

Leu Gly Asp Trp Phe Met Gly Leu Asn Tyr Gln Ile Glu His His
385                 390                 395                 400

Val Phe Pro Asn Met Pro Arg His Asn Leu Pro Thr Val Lys Pro Met
                405                 410                 415

Val Lys Ser Leu Cys Gln Lys Tyr Asp Ile Asn Tyr His Asp Thr Gly
                420                 425                 430

Phe Leu Lys Gly Thr Leu Glu Val Leu Gln Thr Leu Asp Ile Thr Ser
                435                 440                 445

Lys Leu Ser Leu Gln Leu Ser Lys Lys Ser Phe
450                 455

<210> SEQ ID NO 62
<211> LENGTH: 427
<212> TYPE: PRT
<213> ORGANISM: Pavlova salina
<300> PUBLICATION INFORMATION:
<302> TITLE: SYNTHESIS OF LONG-CHAIN POLYUNSATURATED FATTY ACIDS BY
      RECOMBINANT CELLS
<310> PATENT DOCUMENT NUMBER: WO 2005/103253
<311> PATENT FILING DATE: 2005-04-22
<312> PUBLICATION DATE: 2005-11-03
<313> RELEVANT RESIDUES: (1)..(427)

<400> SEQUENCE: 62

Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
                20                  25                  30

Ala Leu His Ile Val Leu Tyr Gly Lys Arg Val Asp Val Thr Lys Phe
            35                  40                  45

Gln Arg Thr His Pro Gly Gly Ser Lys Val Phe Arg Ile Phe Gln Asp
        50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190
```

```
Asn Ala Ala Gly Tyr Phe Leu Gly Phe Val Gln Gly Tyr Ala Val Glu
            195                 200                 205

Trp Trp Arg Ala Arg His Asn Thr His His Val Cys Thr Asn Glu Asp
210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
    290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gly Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380

Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
                405                 410                 415

Asn Ile Arg Ala Leu Ala Phe Glu His Leu Leu
            420                 425

<210> SEQ ID NO 63
<211> LENGTH: 1382
<212> TYPE: DNA
<213> ORGANISM: Euglena gracilis

<400> SEQUENCE: 63
ggcggtcaga gcggcggcgg gcagggggg ggcaacacgg aaggaatgag gggcgaggag      60
gtctgcagag gggggtttgc cgggtcacag ggcggtcgga accaaagcct tggtccatgg    120
cagctgttgc agagaaagac ttggacaccg atttaaatgt tcaaccgcg aaagaagagt    180 tgcgccttcc accttatgcc ggaaaggaac ccttccgacc tgatgtcttc caaccacgaa    240
gtgaagtcag ggaaatcttt ggcacaggca tcaagtacat caagaagaga aactggtggt    300
ggccaagaac ctacaattca acagatattg tctttatcct tgttaccttt tccatgcatg    360
cggctgcgct cattttgggc cccatgacat acaggcctga ttgttggct ttgttttgg    420 gattgtacgt ggtcactgga ctatttggta tcacgctgtc ataccatcgt cagctgtcgc    480
acaggtcctt cacgacaccg aaatggttgg aatacatctt cgcttattgt ggagtcttgg    540
cattccaggg tgatcctctg aatgggtgt gctctcacag gtatcatcac caatattgcg    600
agacagatcg tgatccccac tctgtcaatg aaggattctg tggtctcat atgggatggt    660 tgcttgacca ccaggcaaca aagacacgga ctggagacca gactaactcc atggacatca    720
tgaacgaccc tttctacagc ttcatcagga agacctatcc tttgcatttg gcgctgtttg    780
ccctggccct ctatgcctgg ggtggcattc gtatttggt gtgggcgtg gcagtccgag    840
```

```
tgtgctgggt ctggcacatc acctggtttg tgaactctgc tgttcacact tggggcaaca    900
aggtgtacaa gaccaaccct ccagatgagt ctcgcaacaa ctggtgggtc ggcctccttg    960 catgggtga gggatggcac aacaaccacc acgcattcca gtactctgct cgccacggct   1020
tggaatggtg gcaagttgac atgacgtggg gtgtgattcg ggttctgcag ttcttggggc   1080
tggccaccaa tgtcaagctg ccttctgagg aaaggaaggc tgccatgcgc cttgcctaaa   1140
acgcagcgga ggagccttgc tgtgtttgaa agcaatgcca ctgccggtgt attgtacagg   1200
aacgcttcta attttcggat ttcttttgct ttattgtgcc agtcttccac agtaccattt   1260
cttatgcatc attattaccc tctgatgggt acagtgccaa agacgtcgca cttgttatag   1320
ccatcgattg ctatgggtgc agttgacacc gtccgcaggt ttgccgccag ttgtcatttg   1380
ca                                                                 1382
```